US010424746B2

(12) United States Patent
Metz et al.

(10) Patent No.: US 10,424,746 B2
(45) Date of Patent: Sep. 24, 2019

(54) PT- OR PD-CARBENE COMPLEXES FOR USE IN ORGANIC LIGHT EMITTING DIODES

(71) Applicant: BASF SE, Ludwigshafen (DE)

(72) Inventors: Stefan Metz, Dublin (IE); Thomas Strassner, Dublin (IE); Alexander Tronnier, Dublin (IE); Mario Tenne, Dublin (IE)

(73) Assignee: UDC IRELAND LIMITED, Dublin (IE)

( * ) Notice: Subject to any disclaimer, the term of this patent is extended or adjusted under 35 U.S.C. 154(b) by 0 days.

(21) Appl. No.: 15/526,787

(22) PCT Filed: Nov. 18, 2015

(86) PCT No.: PCT/EP2015/076940
§ 371 (c)(1),
(2) Date: May 15, 2017

(87) PCT Pub. No.: WO2016/079169
PCT Pub. Date: May 26, 2016

(65) Prior Publication Data
US 2017/0365803 A1 Dec. 21, 2017

(30) Foreign Application Priority Data
Nov. 18, 2014 (EP) .................................... 14193650

(51) Int. Cl.
*H01L 51/50* (2006.01)
*H01L 51/00* (2006.01)
(Continued)

(52) U.S. Cl.
CPC ...... *H01L 51/0087* (2013.01); *C07F 15/0086* (2013.01); *C09K 11/06* (2013.01);
(Continued)

(58) Field of Classification Search
None
See application file for complete search history.

(56) References Cited

U.S. PATENT DOCUMENTS

2005/0260445 A1* 11/2005 Walters ................ C07D 487/22
428/690
2010/0213824 A1* 8/2010 Adler .................. C07F 15/0033
313/504

(Continued)

FOREIGN PATENT DOCUMENTS

CN 101065389 A 10/2007
CN 102227438 A 10/2011
(Continued)

OTHER PUBLICATIONS

Baldo et al., "Very high-efficiency green organic light-emitting devices based on electrophosphorescence," Appl. Phys. Lett., vol. 75, No. 1, 4-6 (1999).

(Continued)

Primary Examiner — Gregory D Clark
(74) Attorney, Agent, or Firm — Riverside Law LLP

(57) ABSTRACT

The present invention relates to Pt- or Pd-amidine-carbene complexes, to organic light-emitting diodes (OLEDs) comprising at least one such Pt- or Pd-amidine-carbene complex, to light-emitting layers comprising at least one such Pt- or Pd-amidine-carbene complex, a device, for example stationary or mobile visual display units or illumination means, comprising a corresponding OLED, and to the use of the inventive Pt- or Pd-amidine-carbene complexes in OLEDs, for example as emitters, matrix materials, charge transport materials and/or charge blockers.

16 Claims, 2 Drawing Sheets

Figure 1A:
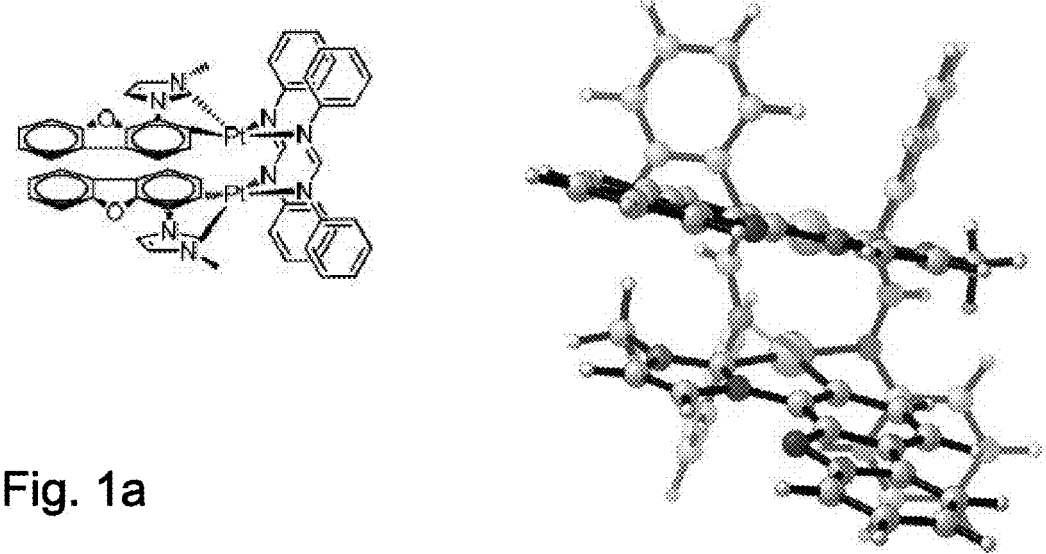

(51) Int. Cl.
*C07F 15/00* (2006.01)
*C09K 11/06* (2006.01)

(52) U.S. Cl.
CPC ...... *H01L 51/0071* (2013.01); *H01L 51/0072* (2013.01); *H01L 51/0084* (2013.01); *C09K 2211/1007* (2013.01); *C09K 2211/1037* (2013.01); *C09K 2211/1044* (2013.01); *C09K 2211/1088* (2013.01); *C09K 2211/185* (2013.01); *H01L 51/0073* (2013.01); *H01L 51/5016* (2013.01)

(56) References Cited

U.S. PATENT DOCUMENTS

| 2010/0320449 | A1* | 12/2010 | Schmid | C07D 487/04 257/40 |
|---|---|---|---|---|
| 2011/0234089 | A1 | 9/2011 | Hou | |
| 2013/0341609 | A1 | 12/2013 | Ma | |
| 2014/0203268 | A1 | 7/2014 | Xia | |

FOREIGN PATENT DOCUMENTS

| WO | 2006056418 | 6/2006 |
|---|---|---|
| WO | 2006067074 | 6/2006 |
| WO | 2012053627 | 4/2012 |
| WO | 2014012972 | 1/2014 |
| WO | 2014024131 | 2/2014 |

OTHER PUBLICATIONS

Japanese Office Action dated Oct. 31, 2018 in JP Application No. 201580056202, 8 pages.

A. Tronnier, "Phosphorescent C∧C* Cyclometalated PtII Dibenzofurangl-NHC Complexes-AN Auxiliary Ligand Study," Eur. J. Inorg. Chem., 2014, 256-264.

Y. Unger, "Green-Blue Emitters: NHC-Based Cyclometalated [Pt(C∧C*)(acac)] Complexes," Angew. Chem. Int. Ed., 2010-11-29, 10214-10216.

* cited by examiner

PT- OR PD-CARBENE COMPLEXES FOR USE IN ORGANIC LIGHT EMITTING DIODES

CROSS-REFERENCE TO RELATED APPLICATIONS

This application is the U.S. National Stage Application filed under 35 U.S.C. § 371 of International Patent Application No. PCT/EP2015/076940, filed Nov. 18, 2015, which is entitled to priority under 35 U.S.C. § 119(a)-(d) to European Patent Application 14193650.0, filed Nov. 18, 2014, all of which applications are hereby incorporated by reference in their entireties.

The present invention relates to Pt- or Pd-carbene complexes, to organic light-emitting diodes (OLEDs) comprising at least one such Pt- or Pd-carbene complex, to light-emitting layers comprising at least one such Pt- or Pd-carbene complex, a device, for example stationary or mobile visual display units or illumination means, comprising a corresponding OLED, and to the use of the inventive Pt- or Pd-carbene complexes in OLEDs, for example as emitters, matrix materials, charge transport materials and/or charge blockers.

Organic light-emitting diodes (OLEDs) exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cellphones, smartphones, digital cameras, mp3 players, laptops, etc. In addition, white OLEDs give great advantages over the illumination technologies known to date, especially a particularly high efficiency.

The prior art proposes numerous materials which emit light on excitation by electrical current.

WO 2006/056418 A2 discloses the use of "unsymmetrical" transition metal-carbene complexes comprising one aromatic ligand and one aliphatic ligand connected with an imidazole ring in organic light-emitting diodes. The imidazole ring may comprise further aromatic or non-aromatic rings fused to the imidazole ring. All complexes shown in the examples in WO2006/056418A2 emit light in the purple to blue region of the electromagnetic spectrum.

WO 2006/67074 A1 discloses electroluminescent metal complexes with nucleophilic carbene ligands.

In both applications, a high number of different Ir-carbene complexes and only one Pt-carbene complex are mentioned in the examples.

WO 2014/012972 relates to dinuclear metal-carbene complexes comprising a central atom selected from platinum and palladium, where both metal atoms are cyclometallated to the same aromatic group, to OLEDs (Organic Light-Emitting Diodes) which comprise such complexes, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker.

One important application for phosphorescent emissive molecules is a full color display. Industry standards for such a display call for pixels adapted to emit the particular colors: saturated red, green and blue pixels. The color may be measured using CIE coordinates, which are well-known to a person skilled in the art.

There is therefore a need to provide phosphorescent emissive molecules emitting with high quantum efficiency and good color purity in the red, green and blue area of the electromagnetic spectrum.

Since highly emissive phosphorescent molecules emitting light in the blue region of the electromagnetic spectrum, based on carbene ligands, are known in the art (see for example the prior art mentioned above), it is an object of the present invention to provide phosphorescent emissive molecules based on transition metal carbene complexes, emitting in the green to red region of the visible electromagnetic spectrum, i.e. having a $\lambda_{max}$ of 520 to 630 nm. Further, it is desirable that the emission lifetime (emission decay time) of said complexes is short.

It is a further object of the present invention to provide organic electronic devices, preferably OLEDs, having—compared with the organic electronic devices known in the art—a high color purity in the green to yellow region of the visible electromagnetic spectrum, a high efficiency, low voltage and/or improved lifetime/stability.

The objects are achieved by providing a complex of the general formula (I) or (II)

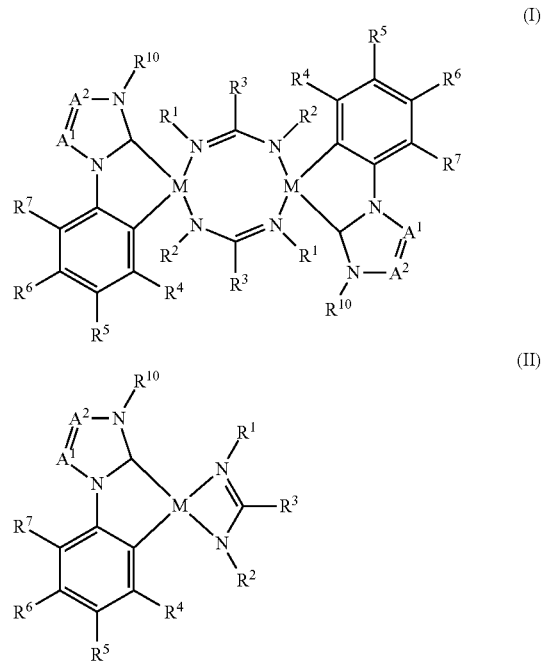

wherein M, $A^1$, $A^2$, $R^1$, $R^2$, $R^3$, $R^4$, $R^5$, $R^6$, $R^7$ and $R^{10}$ are each defined as follows:

M is Pt or Pd, preferably Pt, $A^1$ is N or $CR^8$, preferably $CR^8$, $A^2$ is N or $CR^9$, preferably $CR^9$, $R^1$ and $R^2$ are independently of each other a $C_1$-$C_{18}$alkyl group, which can optionally be substituted by at least one substituent E; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a $C_1$-$C_{18}$haloalkyl group such as $CF_3$; or CN;

preferably, $R^1$ and $R^2$ are independently of each other a $C_1$-$C_{12}$alkyl group, which can optionally be substituted by at least one substituent E; a $C_3$-$C_6$cycloalkyl group, which can optionally be substituted by at least one substituent E; a $C_6$-$C_{14}$aryl group, which can optionally be substituted by one or two substituents G; a heteroaryl group comprising 5 to 11 ring atoms, which can optionally be substituted by one or two substituents G, interrupted by at least one of O, S, N and $NR^{65}$; a $C_1$-$C_{18}$haloalkyl group such as $CF_3$; or CN;

more preferably, $R^1$ and $R^2$ are independently of each other a $C_1$-$C_8$alkyl group, which can optionally be substituted by at least one substituent E; a phenyl group, which can optionally be substituted by one or two substituents G; a heteroaryl group comprising 5 to 11 ring atoms, which can optionally be substituted by one or two substituents G, interrupted by at least one of O, S, N and $NR^{65}$; or CN;

most preferably, $R^1$ and $R^2$ are independently of each other a $C_1$-$C_6$alkyl group; a phenyl group, which can optionally be substituted by one or two substituents G; a heteroaryl group comprising 5 to 6 ring atoms, which can optionally be substituted by one or two substituents G, interrupted by at least one of O, S, N and $NR^{65}$; or CN;

$R^3$ is hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —O—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom, especially F or Cl; a $C_1$-$C_{18}$haloalkyl group such as $CF_3$; or CN;

or $R^1$ and $R^3$ or $R^2$ and $R^3$ together form a group of formula

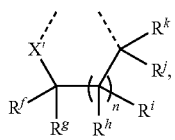

(III)

wherein X' is present in the position of $R^3$ and is selected from O, S, $NR^{75}$ and $CR^{73}R^{74}$;

$R^f$, $R^g$, $R^h$, $R^i$, $R^j$ and $R^k$ are independently of each other H, a $C_1$-$C_5$alkyl group, a fluoro$C_1$-$C_4$alkyl group, or a $C_3$-$C_6$cycloalkyl group; preferably H, a $C_1$-$C_5$alkyl group, $C_3$-$C_6$cycloalkyl group; more preferably H, or a $C_1$-$C_5$alkyl group;

n is 0 or 1;

wherein the group of formula (III) comprises 0, 1 or 2 double bonds, preferably 0-1; in the case that 1 or 2 double bonds are present in the group of formula (III), the carbon atoms connected with the double bonds are each substituted by only one residue $R^f$, $R^j$ and/or—in the case that n is 1—$R^h$;

preferably, $R^3$ is hydrogen; a $C_1$-$C_{12}$alkyl group, which can optionally be substituted by at least one substituent E and/or interrupted by D; a $C_3$-$C_6$cycloalkyl group, which can optionally be substituted by at least one substituent E; a $C_6$-$C_{14}$aryl group, which can optionally be substituted by one or two substituents G; a —O—$C_6$-$C_{14}$aryl group, which can optionally be substituted by one or two substituents G; a heteroaryl group comprising 5 to 11 ring atoms, which can optionally be substituted by one or two substituents G, interrupted by at least one of O, S, N and $NR^{65}$; a halogen atom, especially F or Cl; a $C_1$-$C_{18}$haloalkyl group such as $CF_3$; or CN;

or $R^1$ and $R^3$ or $R^2$ and $R^3$ together form a group of formula

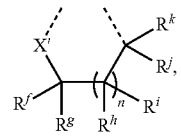

(III)

wherein X' is present in the position of $R^3$ and is selected from O and S;

n is 0 or 1;

$R^f$, $R^g$, $R^h$, $R^i$, $R^j$ and $R^k$ are independently of each other H, a $C_1$-$C_5$alkyl group, $C_3$-$C_6$cycloalkyl group; more preferably H, or a $C_1$-$C_5$alkyl group;

wherein the group of formula (III) comprises 0 double bonds;

more preferably, $R^3$ is hydrogen; a $C_1$-$C_8$alkyl group, which can optionally be substituted by at least one substituent E; a —S—$C_1$-$C_8$alkyl group, which can optionally be substituted by at least one substituent E; a —O—$C_1$-$C_8$alkyl group, which can optionally be substituted by at least one substituent E; a phenyl group, which can optionally be substituted by one or two substituents G; a —O-phenyl group, which can optionally be substituted by one or two substituents G; a heteroaryl group comprising 5 to 11 ring atoms, which can optionally be substituted by one or two substituents G, interrupted by at least one of O, S, N and $NR^{65}$; or CN;

or $R^1$ and $R^3$ or $R^2$ and $R^3$ together form a group of formula

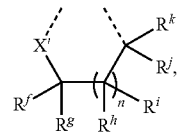

(III)

wherein X' is present in the position of $R^3$ and is S;

n is 0 or 1;

$R^f$, $R^g$, $R^h$, $R^i$, $R^j$ and $R^k$ are independently of each other H, or a $C_1$-$C_5$alkyl group;

wherein the group of formula (III) comprises 0 double bonds;

most preferably, $R^3$ is hydrogen; a $C_1$-$C_5$alkyl group; a —S—$C_1$-$C_5$alkyl group; a —O—$C_1$-$C_5$alkyl group; a phenyl group, which can optionally be substituted by one or two substituents G; a —O-phenyl group, which can optionally be substituted by one or two substituents G; a heteroaryl group comprising 5 to 6 ring atoms, which can optionally be substituted by one or two substituents G, interrupted by at least one of O, S, N and $NR^{65}$; or CN;

$R^5$ and $R^6$ are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —$NR^{65}$—$C_6$-$C_{14}$aryl group, preferably a —$N(C_6$-$C_{14}aryl)_2$ group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom, especially F or Cl; a $C_1$-$C_{18}$haloalkyl group such as $CF_3$; CN; or $SiR^{80}R^{81}R^{82}$; or $R^5$ and $R^6$ together form a group of formula

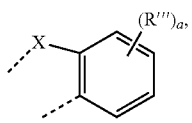

wherein X is O, S, $NR^{75}$ or $CR^{73}R^{74}$; R''' is $C_1$-$C_8$alkyl and a is 0, 1 or 2;

preferably, $R^5$ and $R^6$ are independently of each other hydrogen; a $C_1$-$C_{12}$alkyl group, which can optionally be substituted by E and/or interrupted by D; a $C_3$-$C_{12}$cycloalkyl group, which can optionally be substituted by E; a $C_6$-$C_{10}$aryl group, which can optionally be substituted by at least one substituent G; or $R^5$ and $R^6$ together form a group of formula

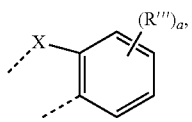

wherein X is O or S; R''' is $C_1$-$C_8$alkyl and a is 0, 1 or 2;

more preferably, $R^5$ and $R^6$ are independently of each other hydrogen; a $C_1$-$C_8$alkyl group, which can optionally be substituted by at least one substituent E and/or interrupted by D; or one of $R^5$ and $R^6$ is a $C_3$-$C_6$cycloalkyl group, which can optionally be substituted by at least one substituent E; or one of $R^5$ and $R^6$ is a phenyl group, which can optionally be substituted by one or two groups G; or $R^5$ and $R^6$ together form a group of formula

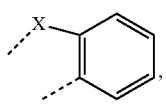

wherein X is O or S;

most preferably, $R^5$ and $R^6$ are independently of each other hydrogen; a $C_1$-$C_8$alkyl group, which can optionally be substituted by at least one substituent E; or a $C_3$-$C_6$cycloalkyl group, which can optionally be substituted by at least one substituent E; or a phenyl group, which can optionally be substituted by one or two groups G;

$R^4$ and $R^7$ are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$ a halogen atom, especially F or Cl; a $C_1$-$C_{18}$haloalkyl group such as $CF_3$; CN; or $SiR^{80}R^{81}R^{82}$;

preferably, $R^4$, $R^7$ are independently of each other hydrogen; or a $C_1$-$C_{12}$alkyl group, which can optionally be substituted by E and/or interrupted by D, preferably a $CH_2$—$C_1$-$C_7$alkyl group, which can optionally be substituted by E and/or interrupted by D;

more preferably, $R^4$, $R^7$ are hydrogen;

or $R^6$ and $R^7$ together form a group of formula

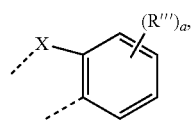

wherein X is O, S, $NR^{75}$ or $CR^{73}R^{74}$; R''' is $C_1$-$C_8$alkyl and a is 0, 1 or 2;

preferably, $R^6$ and $R^7$ together form a group of formula

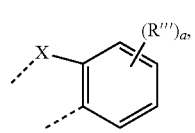

wherein X is O or S; R''' is $C_1$-$C_8$alkyl and a is 0, 1 or 2;

more preferably, $R^6$ and $R^7$ together form a group of formula

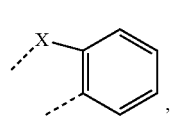

wherein X is O or S;

$R^8$ and $R^9$ are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —O—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom, especially F or Cl; a $C_1$-$C_{18}$haloalkyl group such as $CF_3$; or CN;

or $R^8$ and $R^9$ together form a group of formula

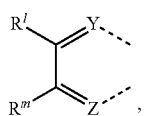     (V)

wherein Y is N or CR$^n$; Z is N or CR$^o$;

$R^l$, $R^m$, $R^n$ and $R^o$ are independently of each other H, a $C_1$-$C_5$alkyl group, a fluoro$C_1$-$C_4$alkyl group, or a $C_3$-$C_6$cycloalkyl group; preferably H, a $C_1$-$C_5$alkyl group, $C_3$-$C_6$cycloalkyl group; more preferably H, or a $C_1$-$C_5$alkyl group;

preferably, $R^8$, $R^9$ are independently of each other hydrogen; a $C_1$-$C_{12}$alkyl group, which can optionally be substituted by E and/or interrupted by D; or a phenyl group, which can optionally be substituted by at least one substituent G; or $R^8$ and $R^9$ together form a group of formula

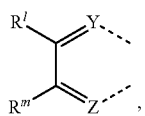     (V)

wherein Y is N or CR$^n$; Z is N or CR$^o$;

$R^l$, $R^m$, $R^n$ and $R^o$ are independently of each other H, a $C_1$-$C_5$alkyl group, $C_3$-$C_6$cycloalkyl group; more preferably H, a $C_1$-$C_5$alkyl group; or an unsubstituted phenyl group; or $R^8$ and $R^9$ together form a group of formula

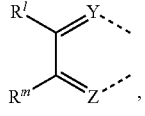

wherein Y is N or CR$^n$; Z is N or CR$^o$;

$R^l$, $R^m$, $R^n$ and $R^o$ are independently of each other H, a $C_1$-$C_5$alkyl group, $C_3$-$C_6$cycloalkyl group; most preferably, $R^8$, $R^9$ are hydrogen; methyl; ethyl; an unsubstituted phenyl group; or a phenyl group, which is substituted by one or two substituents G; or $R^8$ and $R^9$ together form a group of formula

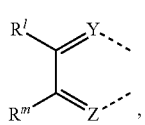     (V)

wherein Y is N or CR$^n$; Z is N or CR$^o$;

$R^l$, $R^m$, $R^n$ and $R^o$ are independently of each other H, or a $C_1$-$C_5$alkyl group;

$R^{10}$ is a $C_1$-$C_{18}$alkyl group, which can optionally be substituted by at least one substituent E; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$;

preferably $R^{10}$ is a $C_1$-$C_{12}$alkyl group, which can optionally be substituted by E; a $C_3$-$C_{12}$cycloalkyl group, which can optionally be substituted by E;

or a group of formula

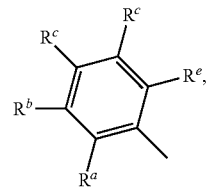     (VI)

wherein $R^a$ and $R^e$ are independently of each other hydrogen H, a $C_1$-$C_5$alkyl group, a fluoro$C_1$-$C_4$alkyl group, or a $C_3$-$C_6$cycloalkyl group; preferably H, a $C_1$-$C_5$alkyl group, $C_3$-$C_6$cycloalkyl group; more preferably H, or a $C_1$-$C_5$alkyl group;

$R^c$, $R^b$ and $R^d$ are independently of each other hydrogen; a $C_1$-$C_{18}$alkyl group, which can optionally be substituted by E and/or interrupted by D; a $C_3$-$C_{12}$cycloalkyl group, which can optionally be substituted by G; a $C_6$-$C_{14}$aryl group, which can optionally be substituted by G; or a heteroaryl group comprising 3 to 30 ring atoms, which is interrupted by at least one of O, S, N or $NR^{65}$ and which can optionally be substituted by G; $C_1$-$C_5$haloalkyl such as $CF_3$; or $SiR^{80}R^{81}R^{82}$; preferably $R^c$, $R^b$ and $R^d$ are independently of each other H, a $C_1$-$C_5$alkyl group, $C_3$-$C_6$cycloalkyl group; more preferably H, or a $C_1$-$C_5$alkyl group;

or $R^c$ and $R^b$, or $R^a$ and $R^b$ together form a group of formula

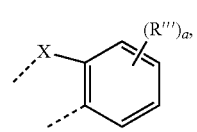     (IV)

wherein X is O, S, $NR^{75}$ or $CR^{73}R^{74}$; R''' is $C_1$-$C_8$alkyl and a is 0, 1 or 2, preferably 0 or 1, more preferably 0;

more preferably $R^{10}$ is a $C_1$-$C_8$alkyl group, which can optionally be substituted by E; a $C_3$-$C_6$cycloalkyl group, which can optionally be substituted by E;

or a group of formula

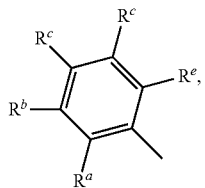

(VI)

wherein $R^a$ and $R^e$ are independently of each other H, a $C_1$-$C_5$alkyl group, $C_3$-$C_6$cycloalkyl group; preferably H, or a $C_1$-$C_5$alkyl group, more preferably H;

$R^c$, $R^b$ and $R^d$ are independently of each other H, a $C_1$-$C_5$alkyl group, $C_3$-$C_6$cycloalkyl group; preferably H, or a $C_1$-$C_5$alkyl group;

or $R^c$ and $R^b$, or $R^a$ and $R^b$ together form a group of formula

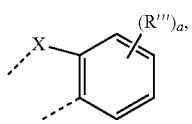

(IV)

wherein X is O or S; R''' is $C_1$-$C_8$alkyl and a is 0, 1 or 2, preferably 0 or 1, more preferably 0;

D is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—; preferably —O—, —S— or —NR$^{65}$—; more preferably —S—, or —O—;

E is —OR$^{69}$, —SR$^{69}$, —NR$^{65}$R$^{66}$, —COR$^{68}$, —COOR$^{67}$, —CONR$^{65}$R$^{66}$, —CN, halogen, or a $C_1$-$C_{18}$alkyl group, which can optionally be substituted by at least one substituent E and/or interrupted by D; preferably, E is $C_1$-$C_8$alkyl, $C_1$-$C_8$alkoxy, CN, halogen, preferably F, or $C_1$-$C_8$haloalkyl, such as CF$_3$; more preferably E is $C_1$-$C_8$alkyl, $C_1$-$C_8$alkoxy, or $C_1$-$C_8$haloalkyl, such as CF$_3$; more preferably, E is —OR$^{69}$, CF$_3$, $C_1$-$C_8$alkyl or F; most preferably CF$_3$, $C_1$-$C_8$alkyl or F;

G is E; or an unsubstituted $C_6$-$C_{14}$aryl group; a $C_6$-$C_{14}$aryl group, which is substituted by F, $C_{18}$alkyl, or $C_1$-$C_{18}$alkyl, which is substituted by F and/or interrupted by O; an unsubstituted heteroaryl group comprising 5 to 11 ring atoms, interrupted by at least one of O, S, N and NR$^{65}$; or a heteroaryl group comprising 5 to 11 ring atoms, interrupted by at least one of O, S, N and NR$^{65}$, which is substituted by F, unsubstituted $C_1$-$C_{18}$alkyl, SiR$^{80}$R$^{81}$R$^{82}$, or $C_1$-$C_{18}$alkyl which is substituted by F and/or interrupted by O; preferably, G is a $C_1$-$C_8$alkyl group, or a group of formula

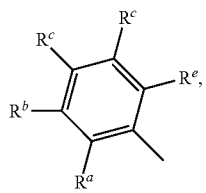

(VI)

$R^a$ and $R^e$ are independently of each other H, a $C_1$-$C_5$alkyl group, a fluoro$C_1$-$C_4$alkyl group, or a $C_3$-$C_6$cycloalkyl group, preferably $R^a$ and $R^e$ are independently of each other H, a $C_1$-$C_5$alkyl group, $C_3$-$C_6$cycloalkyl group; more preferably, $R^a$ and $R^e$ are independently of each other H, or a $C_1$-$C_5$alkyl group;

$R^c$, $R^b$ and $R^d$ are independently of each other hydrogen; a $C_1$-$C_{18}$alkyl group, which can optionally be substituted by E and/or interrupted by D; a $C_3$-$C_{12}$cycloalkyl group, which can optionally be substituted by G; a heterocycloalkyl radical comprising 3 to 10 ring atoms which is interrupted by at least one of O, S and NR$^{65}$ and/or substituted by E; a $C_6$-$C_{24}$aryl group, which can optionally be substituted by G; or a heteroaryl group, comprising 3 to 30 ring atoms, which is interrupted by at least one of O, S, N or NR$^{65}$ and which can optionally be substituted by G; a halogen atom, especially F or Cl; $C_1$-$C_8$haloalkyl such as CF$_3$; CN; or SiR$^{80}$R$^{81}$R$^{82}$, preferably $R^c$, $R^b$ and $R^d$ are independently of each other H, a $C_1$-$C_6$alkyl group, $C_3$-$C_6$cycloalkyl group; more preferably, $R^c$, $R^b$ and $R^d$ are independently of each other H, or a $C_1$-$C_6$alkyl group;

or $R^c$ and $R^b$, or $R^a$ and $R^b$ together form a group of formula

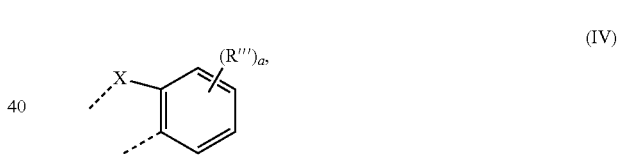

(IV)

wherein X is O, S, NR$^{75}$ or CR$^{73}$R$^{74}$; R''' is $C_1$-$C_8$alkyl and a is 0, 1 or 2, preferably 0 or 1, more preferably 0; more preferably, G is —OR$^{69}$, CF$_3$ or $C_1$-$C_8$alkyl; most preferably, G is CF$_3$ or $C_1$-$C_8$alkyl; even more preferably, G is $C_1$-$C_8$alkyl;

$R^{63}$ and $R^{64}$ are independently of each other H; unsubstituted $C_6$-$C_{14}$aryl; $C_6$-$C_{18}$aryl which is substituted by $C_1$-$C_{18}$alkyl, or $C_1$-$C_{18}$alkoxy; unsubstituted $C_1$-$C_{18}$alkyl; or $C_1$-$C_{18}$alkyl which is interrupted by —O—; preferably unsubstituted $C_6$-$C_{18}$aryl; $C_6$-$C_1$aryl which is substituted by $C_1$-$C_{18}$alkyl, or $C_1$-$C_{18}$alkoxy; unsubstituted $C_1$-$C_{18}$alkyl; or $C_1$-$C_{18}$alkyl which is interrupted by —O—; preferably, $R^{63}$ and $R^{64}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{65}$ and $R^{66}$ are independently of each other H, an unsubstituted $C_6$-$C_{18}$aryl group; a $C_6$-$C_{18}$aryl group which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; or $R^{65}$ and $R^{66}$ together form a five or six membered ring; preferably, $R^{65}$ and $R^{66}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{67}$ is H, an unsubstituted $C_6$-$C_{18}$aryl group; a $C_6$-$C_{18}$aryl group, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; preferably an unsubstituted $C_6$-$C_{18}$aryl group; a $C_6$-$C_{18}$aryl group, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; preferably, $R^{67}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{68}$ is H; an unsubstituted $C_6$-$C_{18}$ aryl group; a $C_6$-$C_{18}$aryl group, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; preferably, $R^{68}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{69}$ is H, an unsubstituted $C_6$-$C_{18}$aryl; a $C_6$-$C_{18}$aryl, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; preferably, $R^{69}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{70}$ and $R^{71}$ are independently of each other an unsubstituted $C_1$-$C_{18}$alkyl group; an unsubstituted $C_6$-$C_{18}$aryl group; or a $C_6$-$C_{18}$aryl group, which is substituted by $C_1$-$C_{18}$alkyl; preferably, $R^{70}$ and $R^{71}$ are independently of each other a phenyl group, which can optionally be substituted by one or two $C_1$-$C_8$alkyl groups; or an unsubstituted $C_1$-$C_{18}$alkyl group;

$R^{72}$ is an unsubstituted $C_1$-$C_{18}$alkyl group; an unsubstituted $C_6$-$C_{18}$aryl group, or a $C_6$-$C_{18}$aryl group, which is substituted by $C_1$-$C_{18}$alkyl; preferably, $R^{72}$ is a phenyl group, which can optionally be substituted by one or two $C_1$-$C_8$alkyl groups; or an unsubstituted $C_1$-$C_{18}$alkyl group;

$R^{73}$ and $R^{74}$ are independently of each other H; unsubstituted $C_6$-$C_{18}$aryl; $C_6$-$C_{18}$aryl which is substituted by $C_1$-$C_{18}$alkyl, or $C_1$-$C_{18}$alkoxy; unsubstituted $C_1$-$C_{18}$alkyl; or $C_1$-$C_{18}$alkyl which is interrupted by —O—; preferably, $R^{73}$ and $R^{74}$ are independently of each other a phenyl group, which can optionally be substituted by one or two $C_1$-$C_8$alkyl groups; an unsubstituted $C_{18}$alkyl group; or a $C_1$-$C_{18}$alkyl group, which is interrupted by —O—;

$R^{75}$ is a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; preferably, $R^{75}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{80}$, $R^{81}$ and $R^{82}$ are independently of each other a $C_1$-$C_{25}$alkyl group, which can optionally be interrupted by O; a $C_6$-$C_{14}$aryl group, which can optionally be substituted by $C_1$-$C_{18}$alkyl; or a heteroaryl group comprising 5 to 11 ring atoms, which can optionally be substituted by $C_1$-$C_{18}$alkyl; preferably, $R^{80}$, $R^{81}$ and $R^{82}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

It has been found by the inventors of the present invention that the inventive Pt- and Pd-carbene complexes mentioned above emit light in the green to red area, especially in the green to orange region of the visible electromagnetic spectrum ($\lambda_{max}$ of 520 to 630 nm). It has been further found by the inventors of the present application that the Pt- and Pd-carbene complexes according to the present invention show a short lifetime of the luminescence (to) of the respective Pt- and Pd-carbene complexes, especially Pt-carbene complexes, of the present invention.

$\tau_0$ is the lifetime of luminescence $\tau_v$ measured divided by the quantum yield (QY):

$$\tau_0 = \tau_v / QY$$

The lifetime of luminescence is defined as the time required for the luminescence intensity to decay from some initial value to e−1 of that value (e=2.718 . . . ). Lifetimes can be measured as known by a person skilled in the art.

These Pt- and Pd-carbene complexes may spend less time in the excited state, thereby de-creasing the possibility for photochemical reactions, or quenching to occur. Therefore, these compounds may provide devices with improved stability and/or also improved device efficiency. In addition, the inventive Pt- and Pd-carbene complexes may provide reduced color-shift of the emission with increasing doping concentration of the compounds in a host material.

Organic electronic devices comprising the Pt- and Pd-carbene complex according to the present invention further show a high efficiency, low voltage and/or improved lifetime/stability.

The inventive Pt- and Pd-carbene complexes are particularly suitable as emitter materials with an emission in the green to red region of the visible electromagnetic spectrum with a $\lambda_{max}$ of 520 to 630 nm. This enables for example the production of white OLEDs, or full-color displays.

Any colour can be expressed by the chromaticity coordinates x and y on the CIE chromaticity diagram. The boundaries of this horseshoe-shaped diagram are the plots of monochromatic light, called spectrum loci, and all the colours in the visible spectrum fall within or on the boundary of this diagram. The arc near the centre of the diagram is called the Planckian locus, which is the plot of the coordinates of black body radiation at the temperatures from 1000 K to 20000 K, described as CCT.

The correlated colour temperature (CCT) is the temperature of a blackbody radiator that has a colour that most closely matches the emission from a nonblackbody radiator.

The Pt- and Pd-carbene complexes of the present invention preferably emit red to green light ($\lambda_{max}$ of 520 to 630 nm) with a FWHM (full width at half maximum) of 30 nm to 100 nm, more preferably of 40 nm to 75 nm.

The triplet decay time (to) of the Pt- and Pd-carbene complexes of the present invention (as emitter) is 0.5 to 10 micro seconds, preferably 0.5 to 5 micro seconds.

The Pt- and Pd-carbene complex according to the present invention is—at room temperature (i.e. at 25° C.)—a phosphorescent emitter.

The phosphosphorescent emitters according to the present invention emit preferably from triplet excited states. Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

The absolute photoluminescence quantum yield of the Pt- and Pd-carbene complexes of the present invention (measured at room temperature (in the context of the present invention "room temperature" is 25° C.)) is in general at least 50%, preferably at least 70%, e.g. 50 to 100%, preferably 70 to 100%.

The determination of the photoluminescence spectra of the inventive Pt- and Pd-carbene complexes as well as the determination of the lifetime of luminescence $\tau_0$ are described below. The further data mentioned below can be determined based on said information by methods known to a person skilled in the art.

A variety of representations are used to depict the bonding in metal-carbenes, including those in which a curved line is used to indicate partial multiple bonding between the carbene carbon and the adjacent heteroatom(s):

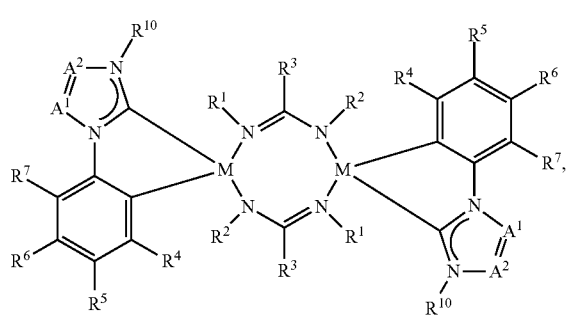

(I)

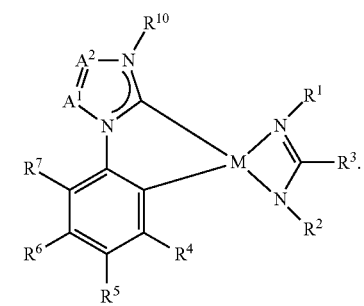

(II)

In the figures and structures herein, a metal-carbene bond is depicted as C-M, as, for example,

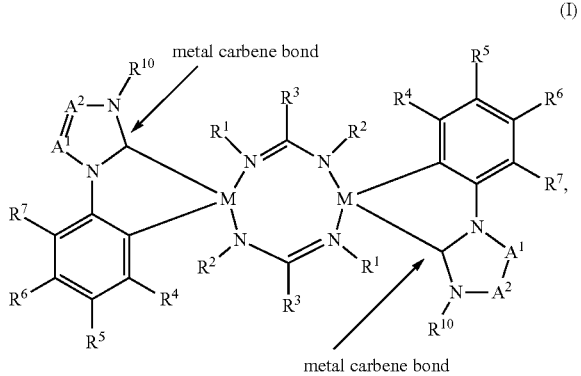

(I)

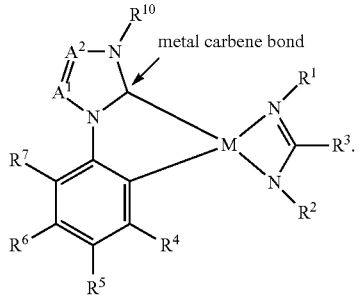

(II)

The complexes of formula (I) and (II) are cyclometallated complexes:

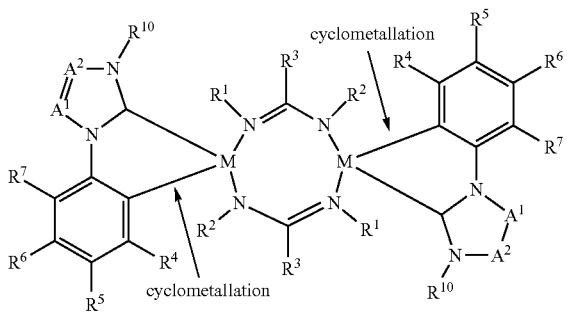

(I)

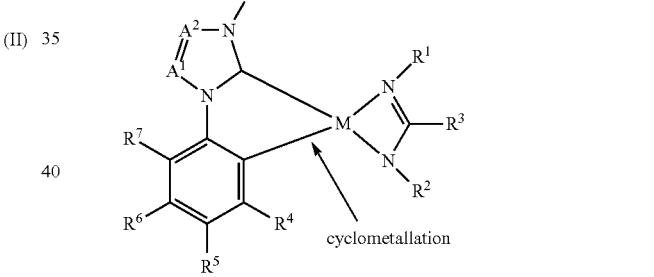

(II)

In the case that $R^{10}$ is a $C_6$-$C_{14}$aryl group, or a heteroaryl group comprising 5 to 11 ring atoms, which groups are suitable for cyclometallation with M, the cyclometallation in the complexes of formula (I) and (II) may occur at $R^{10}$ instead of the cyclometallation position as shown above. Such cyclometallation isomers of the complexes of formula (I) and (II) of the present invention are covered by the complexes shown in formula (I) and (II) of the present invention, i.e. the expression "Complex of the general formula (I) or (II)" mentioned in the claims and specification of the present invention means "Complex of the general formula (I) or (II) and cyclometallation isomers thereof".

It has been found by the inventors that the Pt- and Pd complexes of the present invention are in a solid state usually present in dimeric form as depicted in formula (I).

Even though one isomer of the inventive complexes is shown in formulae (I) and (II), the present invention is not restricted to one isomer, but covers all possible isomers of the complexes shown in formulae (I) and (II).

The residues mentioned in the specification of the present application generally have the following preferred meanings, if not defined differently in a specific residue:

A C$_1$-C$_{18}$alkyl group, which can optionally be substituted by at least one substituent E and/or interrupted by D; preferably a C$_1$-C$_{12}$alkyl group, which can optionally be substituted by at least one substituent E and/or interrupted by D; more preferably a C$_1$-C$_8$alkyl group, which can optionally be substituted by at least one substituent E and/or interrupted by D; most preferably a C$_1$-C$_8$alkyl group, which can optionally be substituted by at least one substituent E; even more preferably an unsubstituted C$_1$-C$_8$alkyl group; further even more preferably an unsubstituted C$_1$-C$_5$alkyl group, e.g. methyl, ethyl, propyl, iso-propyl, sec-butyl, iso-butyl, or neopentyl. The alkyl groups may be linear or branched.

A C$_3$-C$_{12}$cycloalkyl group, which can optionally be substituted by at least one substituent E: preferably a C$_3$-C$_{12}$cycloalkyl group, which can optionally be substituted by at least one substituent E; more preferably a C$_3$-C$_6$cycloalkyl group, which can optionally be substituted by at least one substituent E; most preferably an unsubstituted C$_3$-C$_6$cycloalkyl group, e.g. cyclohexyl or cyclopentyl.

A heterocycloalkyl group comprising 3 to 6 ring atoms, interrupted by at least one of O, S and NR$^{65}$ and/or substituted by at least one substituent E: preferably an unsubstituted heterocycloalkyl group comprising 3 to 6 ring atoms, interrupted by at least one of O, S and NR$^{65}$, e.g. heterocycloalkyl groups based on pyrrolidine, tetrahydrothiophene, tetrahydrofurane, tetrahydropyrane, tetrahydrothiopyrane, piperidine, dioxane, e.g. 1,4-dioxane or morpholine and derivatives thereof substituted by at least one substituent E.

A C$_6$-C$_{14}$aryl group, which can optionally be substituted by at least one substituent G: preferably a C$_6$-C$_{14}$aryl group, which can optionally be substituted by one or two groups G; more preferably a phenyl group, which can optionally be substituted by one or two groups G.

A —NR$^{65}$—C$_6$-C$_{14}$aryl group, which can optionally be substituted by at least one substituent G: preferably a —N(C$_6$-C$_{14}$aryl)$_2$ group, which can optionally be substituted by at least one substituent G; more preferably a —N(phenyl)$_2$ group, which can optionally be substituted by one or two groups G; most preferably an unsubstituted —N(phenyl)$_2$ group.

A heteroaryl group comprising 5 to 11 ring atoms, which can optionally be substituted by at least one substituent G, interrupted by at least one of O, S, N and NR$^{65}$: preferably a heteroaryl group comprising 5 to 11 ring atoms, which can optionally be substituted by one or two groups G, interrupted by at least one of O, S, N and NR$^{65}$; more preferably pyridyl, methylpyridyl, pyrimidyl, pyrazinyl, carbazolyl, dibenzofuranyl, dibenzothiophenyl, indolyl, methylindolyl, benzofuranyl and benzothiophenyl, which can optionally be substituted by one, or more groups selected from a C$_1$-C$_5$alkyl group, a C$_3$-C$_6$cycloalkyl group and a C$_1$-C$_4$fluoroalkyl group; especially carbazolyl, dibenzofuranyl, dibenzothiophenyl, which can optionally be substituted by one, or more groups selected from a C$_1$-C$_5$alkyl group, a C$_3$-C$_6$cycloalkyl group and a C$_1$-C$_4$fluoroalkyl group; more especially dibenzofuranyl, dibenzothiophenyl, which can optionally be substituted by one, or more groups selected from a C$_1$-C$_4$alkyl group, and a C$_3$-C$_6$cycloalkyl group.

A a —NR$^{65}$-heteroaryl group, comprising 5 to 11 ring atoms, which can optionally be substituted by at least one substituent G, interrupted by at least one of O, S, N and NR$^{65}$: preferably a —N(heteroaryl)$_2$ group, comprising 5 to 11 ring atoms, which can optionally be substituted by at least one substituent G, interrupted by at least one of O, S, N and NR$^{65}$, preferred heteroaryl residues are mentioned before.

A halogen atom: preferably F or Cl, more preferably F.

A C$_1$-C$_{18}$haloalkyl group: preferably a fluoroC$_1$-C$_4$alkyl group, more preferably CF$_3$. The alkyl groups may be linear or branched.

In the alkyl groups and aryl groups mentioned in the present application one or more hydrogen atoms may be substituted by deuterium atoms.

Pt- and Pd-Carbene Complexes According to the Present Invention

The residues R$^1$ and R$^2$ in the Pt- and Pd-carbene complexes according to the present invention are independently of each other a C$_1$-C$_{18}$alkyl group, which can optionally be substituted by at least one substituent E; a C$_3$-C$_{12}$cycloalkyl group, which can optionally be substituted by at least one substituent E; a heterocycloalkyl group comprising 3 to 6 ring atoms, interrupted by at least one of O, S and NR$^{65}$ and/or substituted by at least one substituent E; a C$_6$-C$_{14}$aryl group, which can optionally be substituted by at least one substituent G; a heteroaryl group comprising 5 to 11 ring atoms, which can optionally be substituted by at least one substituent G, interrupted by at least one of O, S, N and NR$^{65}$; a C$_1$-C$_{18}$haloalkyl group such as CF$_3$; or CN;

preferably, R$^1$ and R$^2$ are independently of each other a C$_1$-C$_{12}$alkyl group, which can optionally be substituted by at least one substituent E; a C$_3$-C$_6$cycloalkyl group, which can optionally be substituted by at least one substituent E; a C$_6$-C$_{14}$aryl group, which can optionally be substituted by one or two substituents G; a heteroaryl group comprising 5 to 11 ring atoms, which can optionally be substituted by one or two substituents G, interrupted by at least one of O, S, N and NR$^{65}$; a C$_1$-C$_{18}$haloalkyl group such as CF$_3$; or CN;

more preferably, R$^1$ and R$^2$ are independently of each other a C$_1$-C$_8$alkyl group, which can optionally be substituted by at least one substituent E; a phenyl group, which can optionally be substituted by one or two substituents G; a heteroaryl group comprising 5 to 11 ring atoms, which can optionally be substituted by one or two substituents G, interrupted by at least one of O, S, N and NR$^{65}$; or CN;

most preferably, R$^1$ and R$^2$ are independently of each other a C$_1$-C$_5$alkyl group; a phenyl group, which can optionally be substituted by one or two substituents G; a heteroaryl group comprising 5 to 6 ring atoms, which can optionally be substituted by one or two substituents G, interrupted by at least one of O, S, N and NR$^{65}$; or CN.

Especially preferably, R$^1$ and R$^2$ are independently of each other are independently of each other a C$_1$-C$_5$alkyl group; a phenyl group, which can optionally be substituted by one or two substituents selected from CH$_3$, C$_2$H$_5$, C$_3$H$_7$, CF$_3$, OCH$_3$, OC$_2$H$_5$, F, Cl and CN; a heteroaryl group comprising 5 to 6 ring atoms, which can optionally be substituted by one or two substituents selected from CH$_3$, C$_2$H$_5$, C$_3$H$_7$, CF$_3$, OCH$_3$, OC$_2$H$_5$, F, Cl and CN, interrupted by at least one of S, N and NR$^{65}$; or CN; even more preferably CH$_3$,

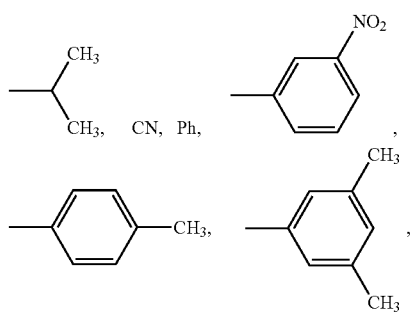

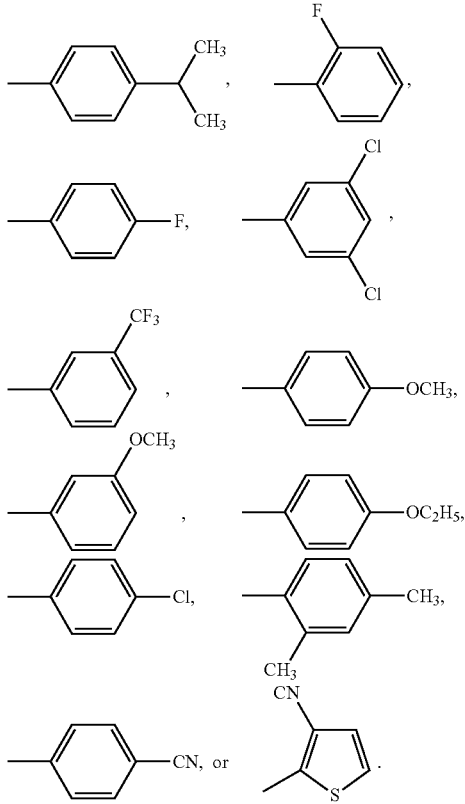

The residue $R^3$ in the Pt- and Pd-carbene complexes according to the present invention is hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —O—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom, especially F or Cl; a $C_1$-$C_{18}$haloalkyl group such as $CF_3$; or CN;

or $R^1$ and $R^3$ or $R^2$ and $R^3$ together form a group of formula

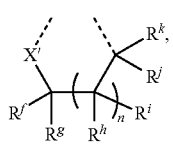
(III)

wherein X' is present in the position of $R^3$ and is selected from O, S, $NR^{75}$ and $CR^{73}R^{74}$;

$R^f$, $R^g$, $R^h$, $R^i$, $R^j$ and $R^k$ are independently of each other H, a $C_1$-$C_5$alkyl group, a fluoro$C_1$-$C_4$alkyl group, or a $C_3$-$C_6$cycloalkyl group; preferably H, a $C_1$-$C_5$alkyl group, $C_3$-$C_6$cycloalkyl group; more preferably H, or a $C_1$-$C_5$alkyl group;

n is 0 or 1;

wherein the group of formula (III) comprises 0, 1 or 2 double bonds, preferably 0 or 1; in the case that 1 or 2 double bonds are present in the group of formula (III), the carbon atoms connected with the double bonds are each substituted by only one residue $R^f$, $R^j$ and/or—in the case that n is 1—$R^h$;

preferably, $R^3$ is hydrogen; a $C_1$-$C_{12}$alkyl group, which can optionally be substituted by at least one substituent E and/or interrupted by D; a $C_3$-$C_6$cycloalkyl group, which can optionally be substituted by at least one substituent E; a $C_6$-$C_{14}$aryl group, which can optionally be substituted by one or two substituents G; a —O—$C_6$-$C_{14}$aryl group, which can optionally be substituted by one or two substituents G; a heteroaryl group comprising 5 to 11 ring atoms, which can optionally be substituted by one or two substituents G, interrupted by at least one of O, S, N and $NR^{65}$; a halogen atom, especially F or Cl; a $C_1$-$C_{18}$haloalkyl group such as $CF_3$; or CN;

or $R^1$ and $R^3$ or $R^2$ and $R^3$ together form a group of formula

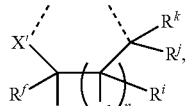
(III)

wherein X' is present in the position of $R^3$ and is selected from O and S;

n is 0 or 1;

$R^f$, $R^g$, $R^h$, $R^i$, $R^j$ and $R^k$ are independently of each other H, a $C_1$-$C_5$alkyl group, $C_3$-$C_6$cycloalkyl group; more preferably H, or a $C_1$-$C_5$alkyl group;

wherein the group of formula (III) comprises 0 double bonds;

more preferably, $R^3$ is hydrogen; a $C_1$-$C_8$alkyl group, which can optionally be substituted by at least one substituent E; a —S—$C_1$-$C_8$alkyl group, which can optionally be substituted by at least one substituent E; a —O—$C_1$-$C_8$alkyl group, which can optionally be substituted by at least one substituent E; a phenyl group, which can optionally be substituted by one or two substituents G; a —O-phenyl group, which can optionally be substituted by one or two substituents G; a heteroaryl group comprising 5 to 11 ring atoms, which can optionally be substituted by one or two substituents G, interrupted by at least one of O, S, N and $NR^{65}$; or CN;

or $R^1$ and $R^3$ or $R^2$ and $R^3$ together form a group of formula

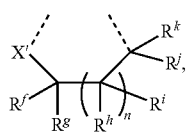
(III)

wherein X' is present in the position of $R^3$ and is S;

n is 0 or 1;

$R^f$, $R^g$, $R^h$, $R^i$, $R^j$ and $R^k$ are independently of each other H, or a $C_1$-$C_5$alkyl group;

wherein the group of formula (III) comprises 0 double bonds;

most preferably, R³ is hydrogen; a $C_1$-$C_5$alkyl group; a —S—$C_1$-$C_5$alkyl group; a —O—$C_1$-$C_5$alkyl group; a phenyl group, which can optionally be substituted by one or two substituents G; a —O-phenyl group, which can optionally be substituted by one or two substituents G; a heteroaryl group comprising 5 to 6 ring atoms, which can optionally be substituted by one or two substituents G, interrupted by at least one of O, S, N and $NR^{65}$; or CN.

Especially preferably, R³ is hydrogen, —$CH_3$, —$C_2H_5$, CN, —S—$CH_3$, Ph,

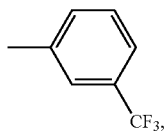

—O-Ph,

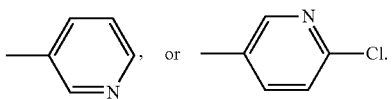

Examples for suitable ligands

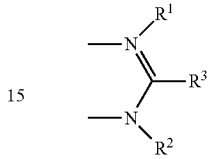

are shown in the following table:

| | R¹ | R² | R³ |
|---|---|---|---|
| 1 | Ph | Ph | H |
| 2 | Ph | Ph | —Ph |
| 3 | Ph | Ph | —CN |
| 4 | 3-$NO_2$-C₆H₄— | 3-$NO_2$-C₆H₄— | —Ph |
| 5 | 3,5-di-$CH_3$-C₆H₃— | —S—(CH₂)₄— (tetrahydrothiopyran) | |
| 6 | —$CH_3$ | 4-F-C₆H₄— | 3-$CF_3$-C₆H₄— |
| 7 | —CN | —Ph | —O—Ph |
| 8 | —CN | 3,5-di-Cl-C₆H₃— | —S—$CH_3$ |
| 9 | —CN | 4-CH(CH₃)₂-C₆H₄— | —S—$CH_3$ |
| 10 | —CH(CH₃)₂ | —Ph | 3-pyridyl |

-continued

| | R¹ | R² | R³ |
|---|---|---|---|
| 11 | 2-fluorophenyl | 2-fluorophenyl | —S—CH₃ |
| 12 | 3-(trifluoromethyl)phenyl | 3-(trifluoromethyl)phenyl | —H |
| 13 | 4-methoxyphenyl | 4-methoxyphenyl | —H |
| 14 | 4-methylphenyl | 4-methylphenyl | —H |
| 15 | 4-ethoxyphenyl | 4-ethoxyphenyl | —CH₃ |
| 16 | —CH₃ | 4-chlorophenyl | 2-chloropyridin-5-yl |
| 17 | 2,4-dimethylphenyl | 2,4-dimethylphenyl | —H |
| 18 | 3-cyano-2-methylthiophen-? | 4-chlorophenyl | —H |
| 19 | 3-methoxyphenyl | 3-methoxyphenyl | —H |
| 20 | 4-cyanophenyl | 4-cyanophenyl | —H |
| 21 | —Ph | —Ph | —CH₃ |
| 22 | —CH₃ | —Ph | —C₂H₅ |
| 23 | —CH₃ | —Ph | —H |
| 24 | isopropyl | —Ph | —H |
| 25 | isopropyl | isopropyl | —H |

-continued

| | R¹ | R² | R³ |
|---|---|---|---|
| 26 |  |  | —Ph |
| 27 | —Ph |  | |
| 28 | —Ph |  | |
| 29 | —Ph |  | |

The residues $R^5$ and $R^6$ in the Pt- and Pd-carbene complexes according to the present invention are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —$NR^{65}$—$C_6$-$C_{14}$aryl group, preferably a —$N(C_6$-$C_{14}$aryl$)_2$ group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom, especially F or Cl; a $C_1$-$C_{18}$haloalkyl group such as $CF_3$; CN; or $SiR^{80}R^{81}R^{82}$; or $R^5$ and $R^6$ together form a group of formula

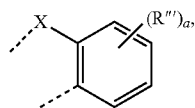

(IV)

wherein X is O, S, $NR^{75}$ or $CR^{73}R^{74}$; R''' is $C_1$-$C_8$alkyl and a is 0, 1 or 2;

preferably, $R^5$ and $R^6$ are independently of each other hydrogen; a $C_1$-$C_{12}$alkyl group, which can optionally be substituted by E and/or interrupted by D; a $C_3$-$C_{12}$cycloalkyl group, which can optionally be substituted by E; a $C_6$-$C_{10}$aryl group, which can optionally be substituted by at least one substituent G; or $R^5$ and $R^6$ together form a group of formula

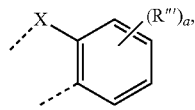

(IV)

wherein X is O or S; R''' is $C_1$-$C_8$alkyl and a is 0, 1 or 2;

more preferably, $R^5$ and $R^6$ are independently of each other hydrogen; a $C_1$-$C_8$alkyl group, which can optionally be substituted by at least one substituent E and/or interrupted by D; or one of $R^5$ and $R^6$ is a $C_3$-$C_6$cycloalkyl group, which can optionally be substituted by at least one substituent E; or one of $R^5$ and $R^6$ is a phenyl group, which can optionally be substituted by one or two groups G; or $R^5$ and $R^6$ together form a group of formula

(IV')

wherein X is O or S;

most preferably, $R^5$ and $R^6$ are independently of each other hydrogen; a $C_1$-$C_8$alkyl group, which can optionally be substituted by at least one substituent E; or a $C_3$-$C_6$cycloalkyl group, which can optionally be substituted by at least one substituent E; or a phenyl group, which can optionally be substituted by one or two groups G.

The residues $R^4$ and $R^7$ in the Pt- and Pd-carbene complexes according to the present invention are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$ a halogen atom, especially F or Cl; a $C_1$-$C_{18}$haloalkyl group such as $CF_3$; CN; or $SiR^{80}R^{81}R^{82}$;

preferably, $R^4$, $R^7$ are independently of each other hydrogen; or a $C_1$-$C_{12}$alkyl group, which can optionally be substituted by E and/or interrupted by D, preferably a $CH_2$—$C_1$-$C_7$alkyl group, which can optionally be substituted by E and/or interrupted by D;

more preferably, $R^4$, $R^7$ are hydrogen;

or $R^6$ and $R^7$ together form a group of formula

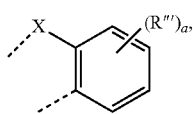

(IV)

wherein X is O, S, $NR^{75}$ or $CR^{73}R^{74}$; R''' is $C_1$-$C_8$alkyl and a is 0, 1 or 2;

preferably, $R^6$ and $R^7$ together form a group of formula

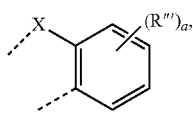

(IV)

wherein X is O or S; R''' is $C_1$-$C_8$alkyl and a is 0, 1 or 2;

more preferably, $R^6$ and $R^7$ together form a group of formula

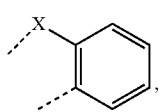

(IV')

wherein X is O or S.

The residues $R^8$ and $R^9$ in the Pt- and Pd-carbene complexes according to the present invention are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —O—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom, especially F or $C_1$; a $C_1$-$C_{18}$haloalkyl group such as $CF_3$; or CN;

or $R^8$ and $R^9$ together form a group of formula

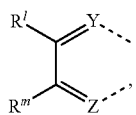

(V)

wherein Y is N or CR''; Z is N or CR°;

$R^l$, $R^m$, $R^n$ and $R^o$ are independently of each other H, a $C_1$-$C_5$alkyl group, a fluoro$C_1$-$C_4$alkyl group, or a $C_3$-$C_6$cycloalkyl group; preferably H, a $C_1$-$C_5$alkyl group, $C_3$-$C_6$cycloalkyl group; more preferably H, or a $C_1$-$C_5$alkyl group;

preferably, $R^8$, $R^9$ are independently of each other hydrogen; a $C_1$-$C_{12}$alkyl group, which can optionally be substituted by E and/or interrupted by D; or a phenyl group, which can optionally be substituted by at least one substituent G;

or $R^8$ and $R^9$ together form a group of formula

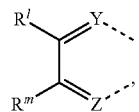

(V)

wherein Y is N or CR''; Z is N or CR°;

$R^l$, $R^m$, $R^n$ and $R^o$ are independently of each other H, a $C_1$-$C_5$alkyl group, $C_3$-$C_6$cycloalkyl group; more preferably H, a $C_1$-$C_5$alkyl group; or an unsubstituted phenyl group; or a phenyl group, which is substituted by one or two substituents G; or $R^8$ and $R^9$ together form a group of formula

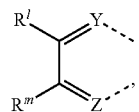

(V)

wherein Y is N or CR''; Z is N or CR°;

$R^l$, $R^m$, $R^n$ and $R^o$ are independently of each other H, a $C_1$-$C_5$alkyl group, $C_3$-$C_6$cycloalkyl group; most preferably, $R^8$, $R^9$ are hydrogen; methyl; ethyl; an unsubstituted phenyl group; or a phenyl group, which is substituted by one or two substituents G; or $R^8$ and $R^9$ together form a group of formula

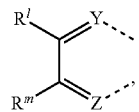

(V)

wherein Y is N or CR''; Z is N or CR°;

$R^l$, $R^m$, $R^n$ and $R^o$ are independently of each other H, or a $C_1$-$C_5$alkyl group.

The residue $R^{10}$ in the Pt- and Pd-carbene complexes according to the present invention is a $C_1$-$C_{18}$alkyl group, which can optionally be substituted by at least one substituent E; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$;

preferably $R^{10}$ is a $C_1$-$C_{12}$alkyl group, which can optionally be substituted by E; a $C_3$-$C_{12}$cycloalkyl group, which can optionally be substituted by E;

or a group of formula

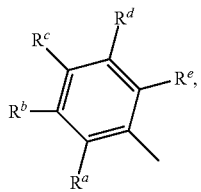

(VI)

wherein $R^a$ and $R^e$ are independently of each other hydrogen H, a $C_1$-$C_5$alkyl group, a fluoro$C_1$-$C_4$alkyl group, or a $C_3$-$C_6$cycloalkyl group; preferably H, a $C_1$-$C_5$alkyl group, $C_3$-$C_6$cycloalkyl group; more preferably H, or a $C_1$-$C_5$alkyl group;

$R^c$, $R^b$ and $R^d$ are independently of each other hydrogen; a $C_1$-$C_{18}$alkyl group, which can optionally be substituted by E and/or interrupted by D; a $C_3$-$C_{12}$cycloalkyl group, which can optionally be substituted by G; a $C_6$-$C_{14}$aryl group, which can optionally be substituted by G; or a heteroaryl group, comprising 3 to 30 ring atoms, which is interrupted by at least one of O, S and $NR^{65}$ and which can optionally be substituted by G; $C_1$-$C_8$haloalkyl such as $CF_3$; or $SiR^{89}R^{81}R^{82}$, preferably $R^c$, $R^b$ and $R^d$ are independently of each other H, a $C_1$-$C_5$alkyl group, $C_3$-$C_6$cycloalkyl group; more preferably H, or a $C_1$-$C_5$alkyl group;

or $R^c$ and $R^b$, or $R^a$ and $R^b$ together form a group of formula

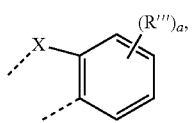

(IV)

wherein X is O, S, $NR^{75}$ or $CR^{73}R^{74}$; R''' is $C_1$-$C_8$alkyl and a is 0, 1 or 2, preferably 0 or 1, more preferably 0;

more preferably $R^{10}$ is a $C_1$-$C_8$alkyl group, which can optionally be substituted by E; a $C_3$-$C_6$cycloalkyl group, which can optionally be substituted by E;

or a group of formula

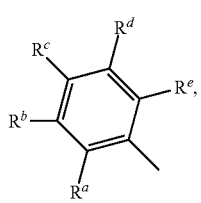

(VI)

wherein $R^a$ and $R^e$ are independently of each other H, a $C_1$-$C_5$alkyl group, $C_3$-$C_6$cycloalkyl group; preferably H, or a $C_1$-$C_5$alkyl group, more preferably H;

$R^c$, $R^b$ and $R^d$ are independently of each other H, a $C_1$-$C_5$alkyl group, $C_3$-$C_6$cycloalkyl group; preferably H, or a $C_1$-$C_5$alkyl group;

or $R^c$ and $R^b$, or $R^a$ and $R^b$ together form a group of formula

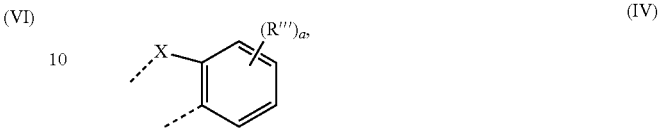

(IV)

wherein X is O or S; R''' is $C_1$-$C_8$alkyl and a is 0, 1 or 2, preferably 0 or 1, more preferably 0.

D is —CO—, —COO—, —S—, —SO—, —$SO_2$—, —O—, —$NR^{65}$—, —$SiR^{79}R^{71}$—, —$POR^{72}$—, —$CR^{63}$=$CR^{64}$—, or —C≡C—; preferably —O—, —S— or —$NR^{65}$—; more preferably —S—, or —O—.

E is —$OR^{69}$, —$SR^{69}$, —$NR^{65}R^{66}$, —$COR^{68}$, —$COOR^{67}$, —$CONR^{65}R^{66}$, —CN, halogen, or a $C_1$-$C_{18}$alkyl group, which can optionally be substituted by at least one substituent E and/or interrupted by D; preferably, E is $C_1$-$C_8$alkyl, $C_1$-$C_8$alkoxy, CN, halogen, preferably F, or $C_1$-$C_8$haloalkyl, such as $CF_3$; more preferably E is $C_1$-$C_8$alkyl, $C_1$-$C_8$alkoxy, or $C_1$-$C_8$haloalkyl, such as $CF_3$; more preferably, E is —$OR^{69}$, $CF_3$, $C_1$-$C_8$alkyl or F; most preferably $CF_3$, $C_1$-$C_8$alkyl or F.

G is E; or an unsubstituted $C_6$-$C_{14}$aryl group; a $C_6$-$C_{14}$aryl group, which is substituted by F, $C_1$-$C_{18}$alkyl, or $C_1$-$C_{18}$alkyl, which is substituted by F and/or interrupted by O; an unsubstituted heteroaryl group comprising 5 to 11 ring atoms, interrupted by at least one of O, S, N and $NR^{65}$; or a heteroaryl group comprising 5 to 11 ring atoms, interrupted by at least one of O, S, N and $NR^{65}$, which is substituted by F, unsubstituted $C_1$-$C_{18}$alkyl, $SiR^{80}R^{81}R^{82}$, or $C_1$-$C_{18}$alkyl which is substituted by F and/or interrupted by O; preferably, G is a $C_1$-$C_8$alkyl group, or a group of formula

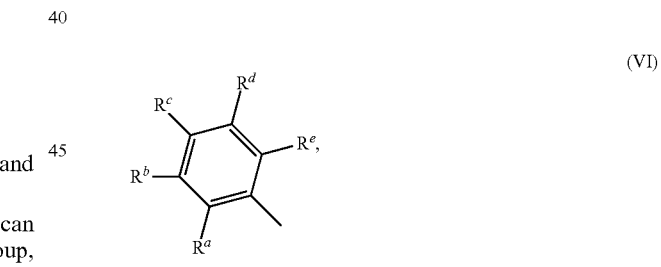

(VI)

$R^a$ and $R^e$ are independently of each other H, a $C_1$-$C_5$alkyl group, a fluoro$C_1$-$C_4$alkyl group, or a $C_3$-$C_6$cycloalkyl group, preferably $R^a$ and $R^e$ are independently of each other H, a $C_1$-$C_5$alkyl group, $C_3$-$C_6$cycloalkyl group; more preferably, $R^a$ and $R^e$ are independently of each other H, or a $C_1$-$C_5$alkyl group;

$R^c$, $R^b$ and $R^d$ are independently of each other hydrogen; a $C_1$-$C_{18}$alkyl group, which can optionally be substituted by E and/or interrupted by D; a $C_3$-$C_{12}$cycloalkyl group, which can optionally be substituted by G; a heterocycloalkyl radical comprising 3 to 10 ring atoms which is interrupted by at least one of O, S and $NR^{65}$ and/or substituted by E; a $C_6$-$C_{24}$aryl group, which can optionally be substituted by G; or a heteroaryl group, comprising 3 to 30 ring atoms, which is interrupted by at least one of O, S, N and $NR^{65}$ and which can optionally be substituted by G; a halogen atom, especially F or Cl; $C_1$-$C_8$haloalkyl such as $CF_3$; CN; or SiR⁸⁰R⁸¹R⁸²; preferably R$^c$, R$^b$ and R$^d$ are independently of each other H, a $C_1$-$C_5$alkyl group, $C_3$-$C_6$cycloalkyl group; more preferably, R$^c$, R$^b$ and R$^d$ are independently of each other H, or a $C_1$-$C_5$alkyl group;

or

R$^c$ and R$^b$, or R$^a$ and R$^b$ together form a group of formula

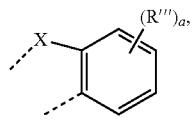

wherein X is O, S, NR$^{75}$ or CR$^{73}$R$^{74}$; R''' is $C_1$-$C_8$alkyl and a is 0, 1 or 2, preferably 0 or 1, more preferably 0; more preferably, G is —OR$^{69}$, CF$_3$ or $C_1$-$C_8$alkyl; most preferably, G is CF$_3$ or $C_1$-$C_8$alkyl; even more preferably, G is $C_1$-$C_8$alkyl.

R$^{63}$ and R$^{64}$ are independently of each other H; unsubstituted $C_6$-$C_{18}$aryl; $C_6$-$C_{18}$aryl which is substituted by $C_1$-$C_{18}$alkyl, or $C_1$-$C_{18}$alkoxy; unsubstituted $C_1$-$C_{18}$alkyl; or $C_1$-$C_{18}$alkyl which is interrupted by —O—; preferably unsubstituted $C_6$-$C_{18}$aryl; $C_6$-$C_{18}$aryl which is substituted by $C_1$-$C_{18}$alkyl, or $C_1$-$C_{18}$alkoxy; unsubstituted $C_1$-$C_{18}$alkyl; or $C_1$-$C_{18}$alkyl which is interrupted by —O—; preferably, R$^{63}$ and R$^{64}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

R$^{65}$ and R$^{66}$ are independently of each other H, an unsubstituted $C_6$-$C_{18}$aryl group; a $C_6$-$C_{18}$aryl group which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; or R$^{65}$ and R$^{66}$ together form a five or six membered ring; preferably, R$^{65}$ and R$^{66}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

R$^{67}$ is H, an unsubstituted $C_6$-$C_{18}$aryl group; a $C_6$-$C_{18}$aryl group, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; preferably an unsubstituted $C_6$-$C_{18}$aryl group; a $C_6$-$C_{18}$aryl group, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; preferably, R$^{67}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

R$^{68}$ is H; an unsubstituted $C_6$-$C_{18}$aryl group; a $C_6$-$C_{18}$aryl group, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; preferably, R$^{68}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

R$^{69}$ is H, an unsubstituted $C_6$-$C_{18}$aryl; a $C_6$-$C_{18}$aryl, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; preferably, R$^{69}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

R$^{70}$ and R$^{71}$ are independently of each other an unsubstituted $C_1$-$C_{18}$alkyl group; an unsubstituted $C_6$-$C_{18}$aryl group; or a $C_6$-$C_{18}$aryl group, which is substituted by $C_1$-$C_{18}$alkyl; preferably, R$^{70}$ and R$^{71}$ are independently of each other a phenyl group, which can optionally be substituted by one or two $C_1$-$C_8$alkyl groups; or an unsubstituted $C_1$-$C_{18}$alkyl group.

R$^{72}$ is an unsubstituted $C_1$-$C_{18}$alkyl group; an unsubstituted $C_6$-$C_{18}$aryl group, or a $C_6$-$C_{18}$aryl group, which is substituted by $C_1$-$C_{18}$alkyl; preferably, R$^{72}$ is a phenyl group, which can optionally be substituted by one or two $C_1$-$C_8$alkyl groups; or an unsubstituted $C_1$-$C_{18}$alkyl group;

R$^{73}$ and R$^{74}$ are independently of each other H; unsubstituted $C_6$-$C_{18}$aryl; $C_6$-$C_{18}$aryl which is substituted by $C_1$-$C_{18}$alkyl, or $C_1$-$C_{18}$alkoxy; unsubstituted $C_1$-$C_{18}$alkyl; or $C_1$-$C_{18}$alkyl which is interrupted by —O—; preferably, R$^{73}$ and R$^{74}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

R$^{75}$ is a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; preferably, R$^{75}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

R$^{80}$, R$^{81}$ and R$^{82}$ are independently of each other a $C_1$-$C_{25}$alkyl group, which can optionally be interrupted by O; a $C_6$-$C_{14}$aryl group, which can optionally be substituted by $C_1$-$C_{18}$alkyl; or a heteroaryl group comprising 5 to 11 ring atoms, which can optionally be substituted by $C_1$-$C_{18}$alkyl; preferably, R$^{80}$, R$^{81}$ and R$^{82}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

In preferred Pt- or Pd-carbene complexes of formula (I) or (II) according to the present invention M, A$^1$ and A$^2$ are each defined as follows:

M is Pt;

A$^1$ is CR$^8$;

A$^2$ is CR$^9$.

In a further preferred embodiment, the Pt- or Pd-carbene complexes according to the present invention are selected from structures (Ia) and (IIa):

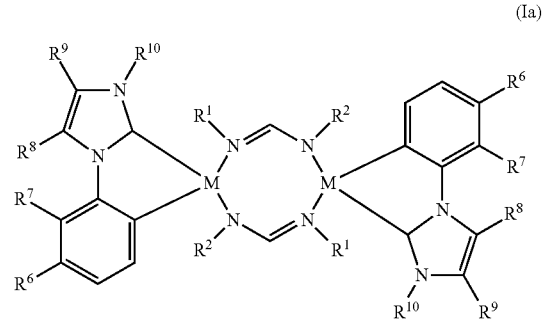

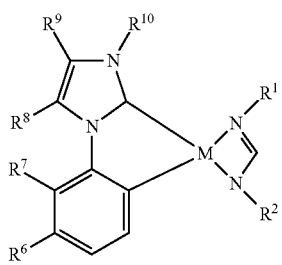

(IIa)

wherein

M is Pt or Pd, preferably Pt, $R^1$ and $R^2$ are independently of each other a $C_1$-$C_5$alkyl group; a phenyl group, which can optionally be substituted by one or two substituents G; a heteroaryl group comprising 5 to 6 ring atoms, which can optionally be substituted by one or two substituents G, interrupted by at least one of O, S, N and $NR^{65}$; or CN;

$R^6$ is hydrogen; a $C_1$-$C_5$alkyl group, which can optionally be substituted by at least one substituent E; a $C_3$-$C_6$cycloalkyl group, which can optionally be substituted by at least one substituent E; or either $R^5$ or $R^6$, preferably $R^5$, is a phenyl group, which can optionally be substituted by one or two groups G;

preferably, $R^6$ is hydrogen; a $C_1$-$C_5$alkyl group; or a $C_3$-$C_6$cycloalkyl group;

more preferably, $R^6$ is hydrogen; a $C_1$-$C_5$alkyl group;

$R^7$ is hydrogen; or a $C_1$-$C_5$alkyl group, which can optionally be substituted by E and/or interrupted by D, preferably a $CH_2$—$C_1$-$C_7$alkyl group, which can optionally be substituted by E and/or interrupted by D;

preferably, $R^7$ is hydrogen;

or $R^6$ and $R^7$ together form a group of formula

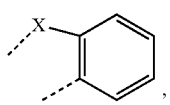

(IV')

wherein X is O or S.

$R^8$ and $R^9$ are hydrogen; methyl; ethyl; an unsubstituted phenyl group; or a phenyl group, which is substituted by one or two $C_1$-$C_8$alkyl groups; or $R^8$ and $R^9$ together form a group of formula

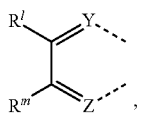

(V)

wherein Y is N or CR''; Z is N or CR°;

$R^l$, $R^m$, R'' and R° are independently of each other H, or a $C_1$-$C_5$alkyl group;

$R^{10}$ is a $C_1$-$C_5$alkyl group, which can optionally be substituted by E; a $C_3$-$C_6$cycloalkyl group, which can optionally be substituted by E;

or a group of formula

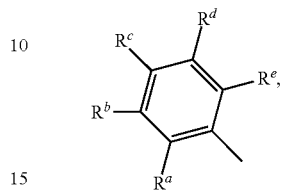

wherein $R^a$ and $R^e$ are independently of each other H, a $C_1$-$C_5$alkyl group, $C_3$-$C_6$cycloalkyl group; preferably H, or a $C_1$-$C_5$alkyl group;

$R^c$, $R^b$ and $R^d$ are independently of each other H, a $C_1$-$C_5$alkyl group, $C_3$-$C_6$cycloalkyl group; preferably H, or a $C_1$-$C_5$alkyl group;

or $R^c$ and $R^b$, or $R^a$ and $R^b$ together form a group of formula

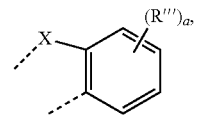

wherein X is O or S; R''' is $C_1$-$C_8$alkyl and a is 0, 1 or 2, preferably 0 or 1, more preferably 0;

D is —S— or —O—;

E is —$OR^{69}$, $CF_3$, $C_1$-$C_8$alkyl or F; most preferably $CF_3$, $C_1$-$C_8$alkyl or F;

G is —$OR^{69}$, $CF_3$ or $C_1$-$C_8$alkyl; preferably, G is $CF_3$ or $C_1$-$C_8$alkyl; more preferably, G is $C_1$-$C_8$alkyl;

$R^{65}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{69}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

Further preferred residues $R^1$, $R^2$, $R^6$, $R^7$, $R^8$, $R^9$ and $R^{10}$ are mentioned above.

Specific examples for Pt- or Pd-carbene complexes according to the present invention are the following complexes (Iaa), (Iab), (Iac), (Iad), (Iae), (Iaf), (Iag), (Iah), (Iai), (Iaj), (IIaa), (IIab), (IIac), (IIad), (IIae), (IIaf), (IIag), (IIah), (IIai) and (IIaj); wherein M is Pt or Pd, preferably Pt:

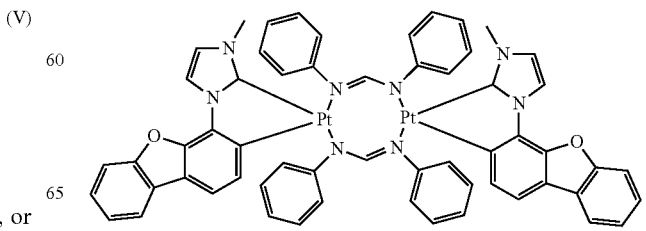

(Iaa)

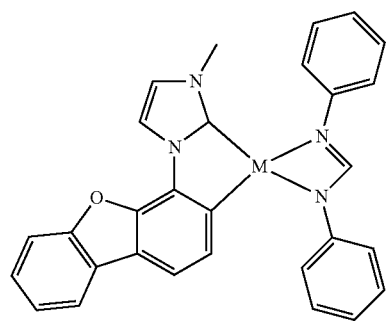
(IIaa)
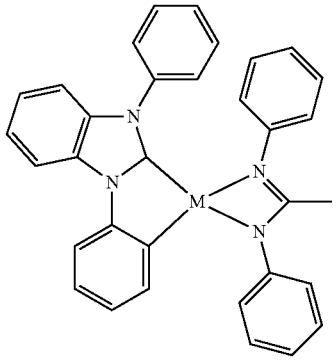
(IIac)
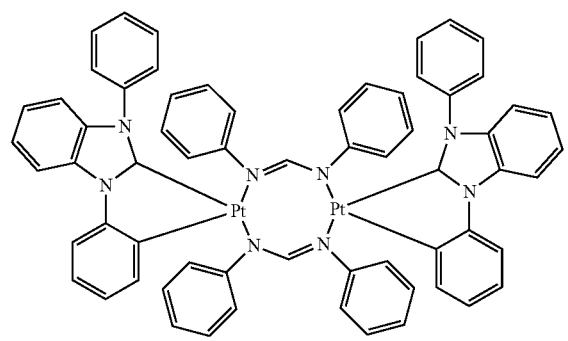
(Iab)
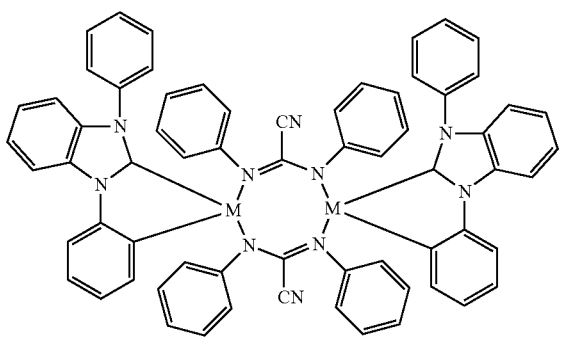
(Iad)
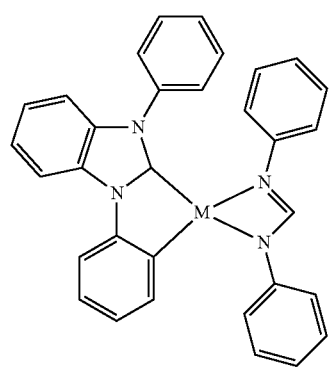
(IIab)
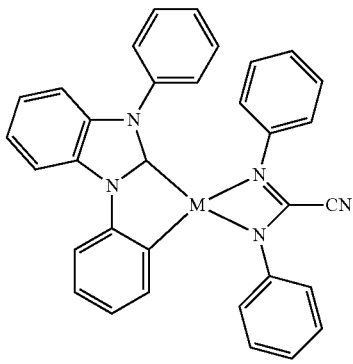
(IIad)
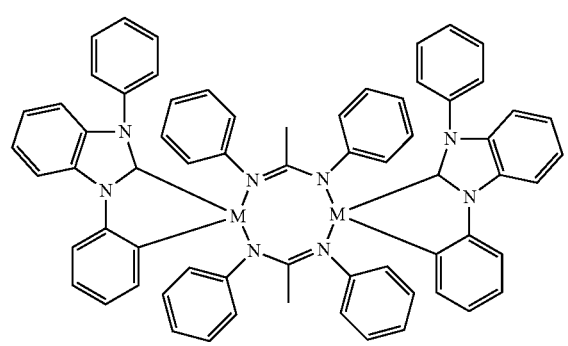
(Iac)
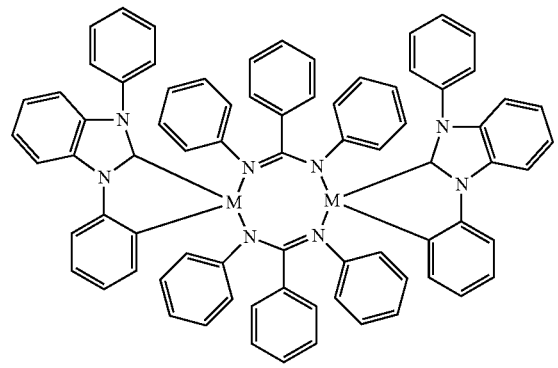
(Iae)

(IIae)
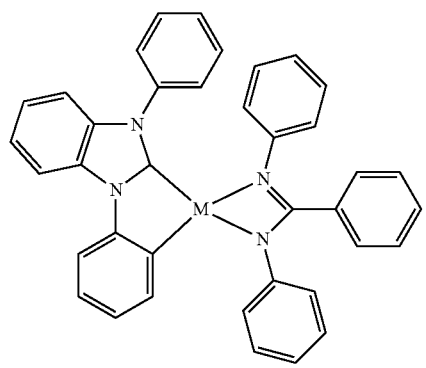
(IIag)
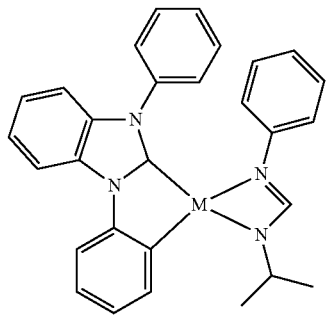
(Iaf)
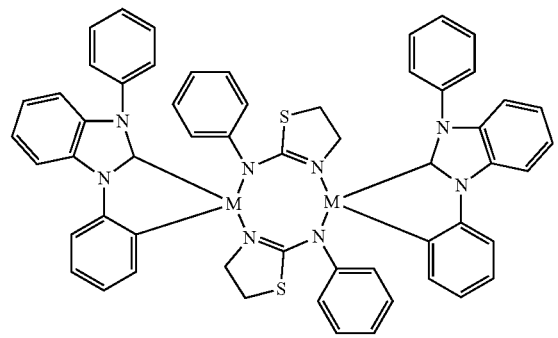
(Iah)
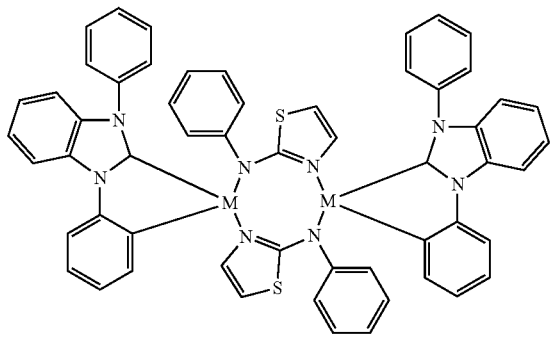
(IIaf)
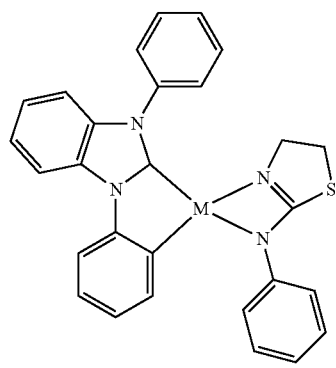
(IIah)
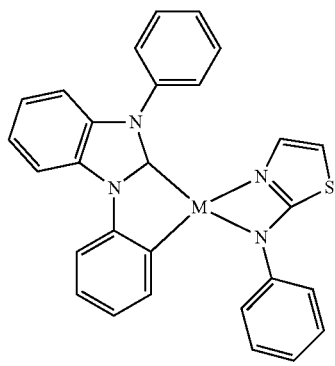
(Iag)
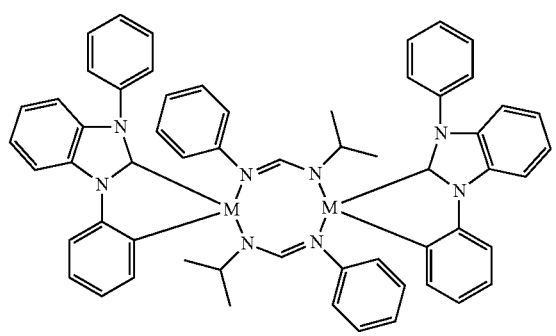
(Iai)
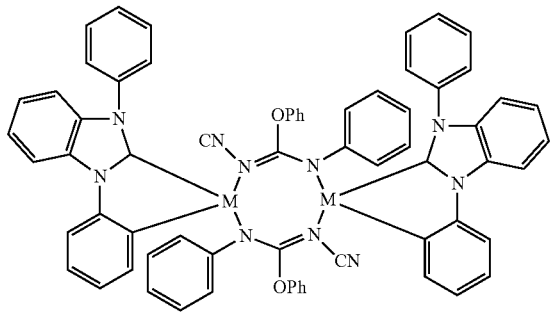

-continued

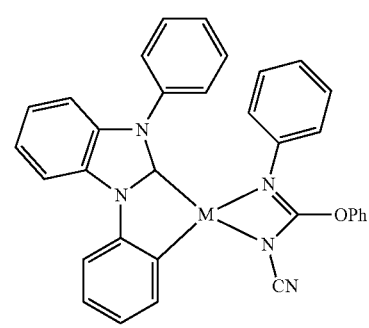
(IIai)

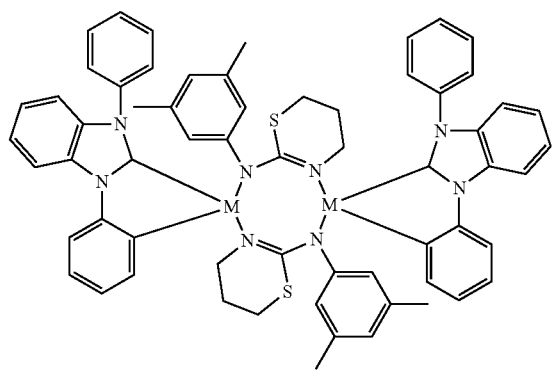
(Iaj)

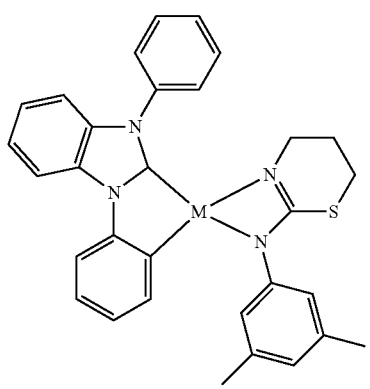
(IIaj)

The inventive Pt- or Pd-carbene complexes of formula (I) or (II) are preferably used in an OLED, preferably as an emitter, matrix material, charge transport material, especially hole transport material, and/or charge blocker, more preferably as an emitter.

The Pt- and Pd-complexes of formula (I) and formula (II) of the present invention are preferably phosphorescence emitter showing emission of light by phosphorescence. However, this does not exclude that the phosphorescence emitter additionally shows emission of light by fluorescence.

The phosphorescence emitter show phosphorescence emission from triplet excited states, preferably at the operating temperatures of the OLED. Generally, the operating temperatures of the OLED are −40 to +90° C. Phosphorescence may be preceded by a transition from a triplet excited state to an intermediate non-triplet state from which the emissive decay occurs.

The emission decay time (intensity reduced to $1/e=0.367879441$ times its initial value) $\tau_0$ of the luminescence emission of the Pt- and Pd-complexes of formula (I) and formula (II) of the present invention is preferably of from 0.1 to 10 micro seconds, more preferably of from 0.5 to 5 micro seconds.

Preparation of the Pt- and Pd-Carbene Complexes According to the Present Invention The present invention further relates to a process for preparing Pt- or Pd-carbene complexes of formula (I) and (II) according to the present invention comprising the steps
(i) contacting an imidazolium salt of formula (IV)

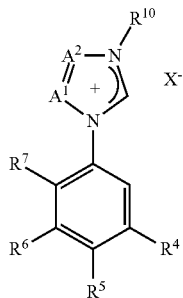
(IV)

wherein
$A^1$ is N or $CR^8$, preferably $CR^8$,
$A^2$ is N or $CR^9$, preferably $CR^9$,
$R^5$ and $R^6$
are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —$NR^{65}$—$C_6$-$C_{14}$aryl group, preferably a —$N(C_6$-$C_{14}aryl)_2$ group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom, especially F or Cl; a $C_1$-$C_{18}$haloalkyl group such as $CF_3$; CN; or $SiR^{89}R^{81}R^{82}$; or
$R^5$ and $R^6$ together form a group of formula

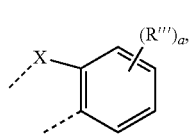
(IV)

wherein X is O, S, $NR^{75}$ or $CR^{73}R^{74}$; R''' is $C_1$-$C_8$alkyl and a is 0, 1 or 2;
$R^4$ and $R^7$
are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and NR$^{65}$ a halogen atom, especially F or Cl; a C$_1$-C$_{18}$haloalkyl group such as CF$_3$; CN; or SiR$^{80}$R$^{81}$R$^{82}$;
or
R$^6$ and R$^7$ together form a group of formula

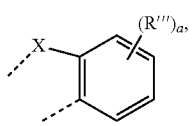

(IV)

wherein X is O, S, NR$^{75}$ or CR$^{73}$R$^{74}$; R''' is C$_1$-C$_8$alkyl and a is 0, 1 or 2;

R$^8$ and R$^9$
are independently of each other hydrogen; a C$_1$-C$_{18}$alkyl group, which can optionally be substituted by at least one substituent E and/or interrupted by D; a C$_3$-C$_{12}$cycloalkyl group, which can optionally be substituted by at least one substituent E; a heterocycloalkyl group comprising 3 to 6 ring atoms, interrupted by at least one of O, S and NR$^{65}$ and/or substituted by at least one substituent E; a C$_6$-C$_{14}$aryl group, which can optionally be substituted by at least one substituent G; a —O—C$_6$-C$_{14}$aryl group, which can optionally be substituted by at least one substituent G; a heteroaryl group comprising 5 to 11 ring atoms, which can optionally be substituted by at least one substituent G, interrupted by at least one of O, S, N and NR$^{65}$; a halogen atom, especially F or Cl; a C$_1$-C$_{18}$haloalkyl group such as CF$_3$; or CN;
or
R$^8$ and R$^9$ together form a group of formula

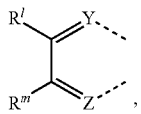

(V)

wherein Y is N or CR$^n$; Z is N or CR$^o$;

R$^l$, R$^m$, R$^n$ and R$^o$ are independently of each other H, a C$_1$-C$_5$alkyl group, a fluoroC$_1$-C$_4$alkyl group, or a C$_3$-C$_6$cycloalkyl group; preferably H, a C$_1$-C$_5$alkyl group, C$_3$-C$_6$cycloalkyl group; more preferably H, or a C$_1$-C$_5$alkyl group;

R$^{10}$
is a C$_1$-C$_{18}$alkyl group, which can optionally be substituted by at least one substituent E; a C$_3$-C$_{12}$cycloalkyl group, which can optionally be substituted by at least one substituent E; a heterocycloalkyl group comprising 3 to 6 ring atoms, interrupted by at least one of O, S and NR$^{65}$ and/or substituted by at least one substituent E; a C$_6$-C$_{14}$aryl group, which can optionally be substituted by at least one substituent G; a heteroaryl group comprising 5 to 11 ring atoms, which can optionally be substituted by at least one substituent G, interrupted by at least one of O, S, N and NR$^{65}$;

D is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—;

E is —OR$^{69}$, —SR$^{69}$, —NR$^{65}$R$^{66}$, —COR$^{68}$, —COOR$^{67}$, —CONR$^{65}$R$^{66}$, —CN, halogen, or a C$_1$-C$_{18}$alkyl group, which can optionally be substituted by at least one substituent E and/or interrupted by D; G is E; or an unsubstituted C$_6$-C$_{14}$aryl group; a C$_6$-C$_{14}$aryl group, which is substituted by F, C$_1$-C$_{18}$alkyl, or C$_1$-C$_{18}$alkyl, which is substituted by F and/or interrupted by O; an unsubstituted heteroaryl group comprising 5 to 11 ring atoms, interrupted by at least one of O, S, N and NR$^{65}$; or a heteroaryl group comprising 5 to 11 ring atoms, interrupted by at least one of O, S, N and NR$^{65}$, which is substituted by F, unsubstituted C$_1$-C$_{18}$alkyl, SiR$^{80}$R$^{81}$R$^{82}$, or C$_1$-C$_{18}$alkyl which is substituted by F and/or interrupted by O;

R$^{63}$ and R$^{64}$ are independently of each other H; unsubstituted C$_6$-C$_{18}$aryl; C$_6$-C$_{18}$aryl which is substituted by C$_1$-C$_{18}$alkyl, or C$_1$-C$_{18}$alkoxy; unsubstituted C$_1$-C$_{18}$alkyl; or C$_1$-C$_{18}$alkyl which is interrupted by —O—; preferably unsubstituted C$_6$-C$_{18}$aryl; C$_6$-C$_{18}$aryl which is substituted by C$_1$-C$_{18}$alkyl, or C$_1$-C$_{18}$alkoxy; unsubstituted C$_1$-C$_{18}$alkyl; or C$_1$-C$_{18}$alkyl which is interrupted by —O—;

R$^{65}$ and R$^{66}$ are independently of each other H, an unsubstituted C$_6$-C$_{18}$aryl group; a C$_6$-C$_{18}$aryl group which is substituted by C$_1$-C$_{18}$alkyl, or C$_1$-C$_{18}$alkoxy; an unsubstituted C$_1$-C$_{18}$alkyl group; or a C$_1$-C$_{18}$alkyl group, which is interrupted by —O—; or R$^{65}$ and R$^{66}$ together form a five or six membered ring;

R$^{67}$ is H, an unsubstituted C$_6$-C$_{18}$aryl group; a C$_6$-C$_{18}$aryl group, which is substituted by C$_1$-C$_{18}$alkyl, or C$_1$-C$_{18}$alkoxy; an unsubstituted C$_1$-C$_{18}$alkyl group; or a C$_1$-C$_{18}$alkyl group, which is interrupted by —O—; preferably an unsubstituted C$_6$-C$_{18}$aryl group; a C$_6$-C$_{18}$aryl group, which is substituted by C$_1$-C$_{18}$alkyl, or C$_1$-C$_{18}$alkoxy; an unsubstituted C$_1$-C$_{18}$alkyl group; or a C$_1$-C$_{18}$alkyl group, which is interrupted by —O—;

R$^{68}$ is H; an unsubstituted C$_6$-C$_{18}$aryl group; a C$_6$-C$_{18}$aryl group, which is substituted by C$_1$-C$_{18}$alkyl, or C$_1$-C$_{18}$alkoxy; an unsubstituted C$_1$-C$_{18}$alkyl group; or a C$_1$-C$_{18}$alkyl group, which is interrupted by —O—;

R$^{69}$ is H, an unsubstituted C$_6$-C$_{18}$aryl; a C$_6$-C$_{18}$aryl, which is substituted by C$_1$-C$_{18}$alkyl, or C$_1$-C$_{18}$alkoxy; an unsubstituted C$_1$-C$_{18}$alkyl group; or a C$_1$-C$_{18}$alkyl group, which is interrupted by —O—;

R$^{70}$ and R$^{71}$ are independently of each other an unsubstituted C$_1$-C$_{18}$alkyl group; an unsubstituted C$_6$-C$_{18}$aryl group; or a C$_6$-C$_{18}$aryl group, which is substituted by C$_1$-C$_{18}$alkyl;

R$^{72}$ is an unsubstituted C$_1$-C$_{18}$alkyl group; an unsubstituted C$_6$-C$_{18}$aryl group, or a C$_6$-C$_{18}$aryl group, which is substituted by C$_1$-C$_{18}$alkyl;

R$^{73}$ and R$^{74}$ are independently of each other H; unsubstituted C$_6$-C$_{18}$aryl; C$_6$-C$_{18}$aryl which is substituted by C$_1$-C$_{18}$alkyl, or C$_1$-C$_{18}$alkoxy; unsubstituted C$_1$-C$_{18}$alkyl; or C$_1$-C$_{18}$alkyl which is interrupted by —O—;

R$^{75}$ is a C$_6$-C$_{18}$aryl group; a C$_6$-C$_{18}$aryl which is substituted by C$_1$-C$_{18}$alkyl, or C$_1$-C$_{18}$alkoxy; a C$_1$-C$_{18}$alkyl group; or a C$_1$-C$_{18}$alkyl group, which is interrupted by —O—; preferably, R$^{75}$ is a phenyl group, which can optionally be substituted by one or two C$_1$-C$_8$alkyl groups; an unsubstituted C$_1$-C$_{18}$alkyl group; or a C$_1$-C$_{18}$alkyl group, which is interrupted by —O—;

R$^{80}$, R$^{81}$ and R$^{82}$ are independently of each other a C$_1$-C$_{25}$alkyl group, which can optionally be interrupted by O; a C$_6$-C$_{14}$aryl group, which can optionally be substituted by C$_1$-C$_{18}$alkyl; or a heteroaryl group comprising 5 to 11 ring atoms, which can optionally be substituted by C$_1$-C$_{18}$alkyl; and X$^-$ is halide, preferably chloride, bromide or iodide, more preferably chloride or iodide, BF$_4^-$, PF$_6^-$, SbF$_6^-$, ClO$_4^-$, with a Pt salt or a Pd salt, preferably selected from Pt(COD)Cl$_2$ (COD=cyclooctadiene), Pt(PPh$_3$)Cl$_2$, Pt(pyridine)$_2$Cl$_2$, [PtMe$_2$(SMe$_2$)]$_2$, Pt(SMe$_2$)Cl$_2$, Pt(SEt$_2$)Cl$_2$, Pt(phenanthroline)Cl$_2$, Pt(NH$_3$)$_2$Cl$_2$, Pt(acac)$_2$, PtCl$_2$, $K_2PtCl_4$, $Pd(allyl)Cl_2$, $Pd(COD)Cl_2$ (COD=cyclooctadiene), $Pd(PPh_3)_2Cl_2$, $Pd(CH_3CN)_2Cl_2$, $Pd(acac)_2$, $PdCl_2$, $K_2PdCl_4$ and mixtures thereof, more preferably $Pt(COD)Cl_2$, $Pt(PPh_3)_2Cl_2$, $Pt(pyridine)_2Cl_2$, $[PtMe_2(SMe_2)]_2$, $Pt(SMe_2)Cl_2$, $Pt(SEt_2)Cl_2$, $Pt(phenanthroline)Cl_2$, $Pt(NH_3)_2Cl_2$, $PtCl_2$, $K_2PtCl_4$, and mixtures thereof, most preferably $Pt(COD)Cl_2$, in the presence of a Ag or Cu(I) salt, preferably $Ag_2O$;

(ii) contacting the product obtained in step (i) with a compound of formula (VII)

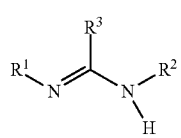

(VII)

wherein $R^1$ and $R^2$ are independently of each other a $C_1$-$C_{18}$alkyl group, which can optionally be substituted by at least one substituent E; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a $C_1$-$C_{18}$haloalkyl group such as $CF_3$; or CN;

$R^3$ is hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —O—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom, especially F or Cl; a $C_1$-$C_{18}$haloalkyl group such as $CF_3$; or CN;

or $R^1$ and $R^3$ or $R^2$ and $R^3$ together form a group of formula

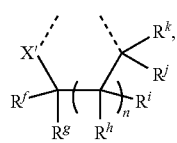

(III)

wherein X' is present in the position of $R^3$ and is selected from O, S, $NR^{75}$ and $CR^{73}R^{74}$;

$R^f$, $R^g$, $R^h$, $R^i$, $R^j$ and $R^k$ are independently of each other H, a $C_1$-$C_5$alkyl group, a fluoro$C_1$-$C_4$alkyl group, or a $C_3$-$C_6$cycloalkyl group; preferably H, a $C_1$-$C_5$alkyl group, $C_3$-$C_6$cycloalkyl group; more preferably H, or a $C_1$-$C_5$alkyl group;

n is 0 or 1;

wherein the group of formula (III) comprises 0, 1 or 2 double bonds, preferably 0 or 1; in the case that 1 or 2 double bonds are present in the group of formula (III), the carbon atoms connected with the double bonds are each substituted by only one residue $R^f$, $R^j$ and/or—in the case that n is 1—$R^h$;

in the presence of a base, preferably selected from M' tert.-butoxide and M'hexamethyldisilazide (M'HMDS), wherein M' is selected from K, Na, and Li, or mixtures thereof.

Suitable imidazolium salts of formula (IV) are obtained by processes known in the art, for example starting from commercially available imidazolines.

Suitable compounds of formula (VII) are commercially available or are obtained by processes known in the art.

Preferred residues and groups $R^1$, $R^2$, $R^3$, $R^4$, $R^5$, $R^6$, $R^7$, $A^1$ and $A^2$ of the imidazolimium salts (IV) and the compounds of formula (VII) are the residues $R^1$, $R^2$, $R^3$, $R^4$, $R^5$, $R^6$, $R^7$, $A^1$ and $A^2$ mentioned above.

Step (i)

The molar ratio of the compounds of formula (IV) to the Pt salt or Pd salt is for example 1 to 2 to 2 to 1, preferably 1 to 1.5 to 1.5 to 1, more preferably 1 to 1.2 to 1.2 to 1.

The molar ratio of the compounds of formula (IV) to the Ag salt is for example 1 to 2 to 2 to 1.

The reaction in step (i) is effected generally at a temperature of 0 to 150° C., preferably 10 to 120° C., more preferably 20° C. to 120° C.

Preference is given to performing the process in step (i) according to the invention in a solvent.

Suitable solvents are known to those skilled in the art, for example ethers, cyclic ethers, ketones, polar solvents, preferably dioxane, butanone, ethoxyethanol, dimethylformamide (DMF) or mixtures thereof.

The reaction time in step (i) depends on the desired Pt- or Pd-carbene complex and is generally 1 to 80 hours, preferably 2 to 70 hours, more preferably 10 to 60 hours.

In a preferred embodiment, step (ii) is carried out subsequently to step (i) after removal of the solvent at the end of the reaction in step (i). No further work-up of the product obtained in step (i) is necessary.

Step (ii)

The molar ratio of the compound of formula (IV) to the compound of formula (VII) is for example 1 to 0.75 to 1 to 10, preferably 1 to 1 to 1 to 8, more preferably 1 to 1 to 1 to 6.

The molar ratio of the compound of formula (IV) to the base is for example 1 to 1 to 1 to 10, preferably 1 to 1 to 1 to 8, more preferably 1 to 1 to 1 to 6.

The reaction in step (ii) is effected generally at a temperature of 0 to 150° C., preferably 10 to 120° C., more preferably 20° C. to 120° C.

Preference is given to performing the process in step (ii) according to the invention in a solvent. Suitable solvents are known to those skilled in the art, for example ethers, cyclic ethers, ketones, polar solvents, preferably dimethylformamide (DMF), dioxane, butanone, ethoxyethanol or mixtures thereof.

The reaction time in step (ii) depends on the desired Pt- or Pd-carbene complex and is generally 1 to 60 hours, preferably 2 to 50 hours, more preferably 5 to 40 hours.

The resulting Pt- or Pd-carbene complex can be worked up by methods known to those skilled in the art. For example, the reaction solvent is removed, preferably in vacuo, the resulting residues are optionally washed, for example with water, and then purified by column chromatography with dichloromethane, isohexane or a mixture of dichloromethane and isohexane, and dried.

Organic Electronic Device

According to the present invention, the Pt- or Pd-carbene complexes of formula (I) or (II) according to the present invention are preferably employed in an organic electronic device, preferably in an organic light emitting diode (OLED). The inventive Pt- or Pd-carbene complexes of formula (I) or (II) are used in the OLED preferably as an emitter, matrix material, charge transport material, especially hole transport material, and/or charge blocker, more preferably as an emitter and/or hole transport material, most preferably as emitter. Most preferably, the Pt- or Pd-carbene complexes of formula (I) or (II) are employed as emitter material, preferably as emitter material in the light-emitting layer of an OLED. Suitable OLEDs are known in the art and the preferred structures of suitable OLEDs are described below.

The present invention therefore further relates to an organic light emitting diode comprising a Pt- or Pd-carbene complexes of formula (I) or (II) according to the present invention.

Further, the present invention relates to a light-emitting layer comprising a Pt- or Pd-carbene complexes of formula (I) or (II) according to the present invention, preferably as emitter material.

More preferably, the light-emitting layer comprises the complex of formula (I) or (II) as emitter material together with at least one host material. The present invention further relates to an OLED comprising the inventive light-emitting layer.

Organic light-emitting diodes are in principle formed from a plurality of layers, e.g.:

(a) an anode,
(b) optionally a hole injection layer,
(c) optionally a hole transport layer,
(d) optionally an electron/exciton blocking layer
(e) a light-emitting layer,
(f) optionally a hole/exciton blocking layer,
(g) optionally an electron transport layer,
(h) optionally an electron injection layer, and
(i) a cathode.

It is, however, also possible that the OLED does not comprise all of the layers mentioned; for example, an OLED comprising layers (a) (anode), (e) (light-emitting layer) and (i) (cathode) is likewise suitable, in which case the functions of layers (c) (hole-transport layer) and (g) (electron-transport layer) are assumed by the adjoining layers. OLEDs comprising layers (a), (c), (e), (g) and (i) or (a), (c), (e) and (i) or layers (a), (e), (g) and (i) are likewise suitable.

The individual layers among the aforementioned layers of the OLED may in turn be formed from two or more layers. For example, the hole-transport layer may be formed from one layer, into which holes are injected from the electrode, and a layer which transports the holes away from the hole-injecting layer into the light-emitting layer. The electron-transport layer may likewise consist of a plurality of layers, for example of a layer in which electrons are injected through the electrode and a layer which receives electrons from the electron-injecting layer and transports them into the light-emitting layer. These layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is matched optimally to the inventive Pt- or Pd-carbene complexes, preferably used as emitter substances in accordance with the invention.

In order to obtain particularly efficient OLEDs, the HOMO (highest occupied molecular orbital) of the hole-transport layer should be aligned to the work function of the anode, and the LUMO (lowest unoccupied molecular orbital) of the electron-transport layer should be aligned to the work function of the cathode.

Suitable materials for the aforementioned layers (anode, cathode, hole and electron injection materials, hole and electron transport materials and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices in Organic Light-Emitting Materials and Devices*, eds: Z. Li, H. Meng, Taylor & Francis, 2007, Chapter 3, pages 295 to 411.

In addition, it is possible that some or all of the layers (b) to (h) have been surface-treated in order to increase the efficiency of charge carrier transport. The selection of the materials for each of the layers mentioned is preferably determined by obtaining an OLED having a high efficiency.

The inventive Pt- or Pd-carbene complexes are preferably used as emitter molecules in the light-emitting layer (e). The inventive Pt- or Pd-carbene complexes may in addition to use as emitter molecules in the light-emitting layer (e) or instead of use in the light-emitting layer also be used as a matrix material in the light-emitting layer (e), charge transport material in the hole-transport layer (c) or in the electron-transport layer (g) and/or as a charge blocker, preference being given to use as a charge transport material in the hole-transport layer (c) (hole transport material).

Light-Emitting Layer (e)

Emitter

Suitable emitter materials for OLEDs are known by a person skilled in the art. The light-emitting layer preferably comprises at least one phosphorescent emitter. Phosphorescent emitter are preferred because of the higher luminescent efficiencies associated with such materials. The light-emitting layer preferably also comprises at least one host material. Preferably, the host material is capable of transporting electrons and/or holes, doped with an emitting material that may trap electrons, holes, and/or excitons, such that excitons relax from the emissive material via a photoemissive mechanism.

It is an object of the present invention to provide organic electronic devices, preferably OLEDs, having—compared with the organic electronic devices known in the art—a high color purity in the green to red region of the visible electromagnetic spectrum, a high efficiency, low voltage and/or improved lifetime/stability. to provide organic electronic devices, preferably OLEDs, having—compared with the organic electronic devices known in the art—a high color purity in the green to red region of the visible electromagnetic spectrum, a high efficiency, low voltage and/or improved lifetime/stability.

The emitter in the OLED of the present invention is therefore preferably a phosphorescent emitter emitting light in the green to red region of the visible electromagnetic spectrum ("phosphorescent emitter").

The term "phosphorescent emitter" as used herein refers to a green to red phosphorescent emitter usually having an emission maximum ($\lambda_{max}$), which is located at 520 nm to 630 nm.

Suitable phosphorescent green emitters are known in the prior art, for example in Baldo et al., Applied Physics Letters, vol. 75, No. 1, 5 Jul. 1999, 4-6, US 2011/0227049 A1, US 2014/0203268 A1, US 2013/0341609, US 2013/0181190, US 2013/0119354, WO 2012/053627 A1, and WO 2013/112557.

Preferably, the inventive Pt- and Pd-carbene complexes of formula (I) or (II) are used as emitter. The light-emitting layer (e) preferably comprises at least one Pt- and Pd-carbene complex of formula (I) or (II) as emitter material. Suitable and preferred inventive Pt- and Pd-carbene complexes of formula (I) or (II) are mentioned above. It is also possible that the light-emitting layer comprises in addition to at least one inventive Pt- and Pd-carbene complex of formula (I) or (II) one or more further emitters.

The light-emitting layer preferably comprises beside at least one emitter material (suitable emitter materials are mentioned above), preferably at least one Pt- and Pd-carbene complex of formula (I) or (II) according to the present invention, at least one host material.

Suitable host materials are known by a person skilled in the art. Preferred host materials are mentioned below.

Host

For efficient light emission the triplet energy of the host material has to be (about 0.2 eV) larger than the triplet energy of the phosphorescent emitter (preferably the Pt- and Pd-carbene complex of formula (I) or (II) according to the present invention) used. Hence, all host materials fulfilling this requirement are, in principle, suitable as host compound.

Suitable host materials for phosphorescent green to red emitters are, for example, described in EP2363398A1, WO2008031743, WO2008065975, WO2010145991, WO2010047707, US20090283757, US20090322217, US20100001638, WO2010002850, US20100060154, US20100060155, US20100076201, US20100096981, US20100156957, US2011186825, US2011198574, US20110210316, US2011215714, US2011284835, and WO2012045710. The host material may be a compound having hole-transporting property and/or an organic compound having electron-transporting property. Preferably, the host material is an organic compound or organometallic compound having hole-transporting property. Alternatively the host compound may be a mixture of an organic compound or organometallic compound having hole-transporting property and an organic compound or organometallic compound having electron-transporting property. In principle, any organic compound or organometallic compound having hole-transporting property or having electron-transporting property and sufficient triplet energy can be used as host in the light-emitting layer.

Examples of organic compounds which can be used for the host material include a carbazole derivative such as 4,4'-di(carbazolyl)biphenyl (abbreviation: CBP), 1,3-bis(carbazolyl)benzene (abbreviation: mCP) or 1,3,5-tris(N-carbazolyl)benzene (abbreviation: TCzB), =DNTPD.

Examples of organometallic compounds which can be used for the host material include iridium carbene complexes. Suitable iridium carbene complexes are, for example, iridium carbene complexes as described in WO2005/019373A2, WO2006/056418 A2, WO2007/115970, WO2007/115981, WO2008/000727, WO2012/121936A2, US2012/0305894A1, and WO2012/172482A1. Examples of suitable iridium carbene complexes are Ir(D-PBIC)$_3$ with the formula:

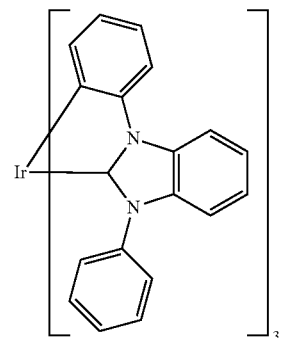

(HTM-1)

and Ir(ABIC)$_3$ with the formula:

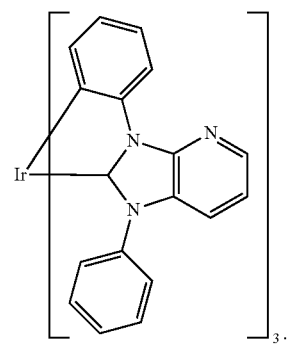

(HTM-2)

Further suitable host materials are compounds of formula (X) as described below. The compounds of formula (X) are described in WO2010079051 (in particular pages on 19 to 26 and in tables on pages 27 to 34, pages 35 to 37 and pages 42 to 43).

Also preferred as host compounds in the OLED and in the light-emitting layer of the present invention are the compounds mentioned in WO2012/130709; WO2013/050401; WO2014/009317; WO2014/044722; and the non-published European Patent Application EP13191100.0.

Further preferred host materials are binary host systems as described in WO 2011/136755; the hosts described in WO 2013/022419 and WO 2013/112557; triphenylene derivatives for example as described in WO 2010/028151, WO 2010/002850, WO 2010/0056669, US 20100244004, US 20110177641, US 2011022749, WO 2011/109042, and WO 2011137157; azaborinine compounds for example as described in WO 2011/143563; bicarbazole compounds for example as described in WO 2012/023947; carbazolephenyl-pyridine, -pyrimidine and triazine compounds for example as described in WO 2012/108879; biscarbazole-phenyl-pyridine, -pyrimidine and triazine compounds for example as described in WO 2012/108881; dibenzoquinoxaline compounds for example as described in US 20110210316; triazole derivatives for example as described in US 20110285276 and US 20120025697; benimidazole derivatives for example as described in US 20110147792; heterocyclic compounds for example as described in US 20120061651; phenanthrene derivatives for example as described in US 20120104369; benzoxazole derivatives for example as described in US 20120132896; oxazole derivatives for example as described in US 20120130081; and carbazole-benzimidazole derivatives for example as described in US 20120133274.

Especially suitable host materials are for example host materials described in WO 2013/112557 having the following general formula:

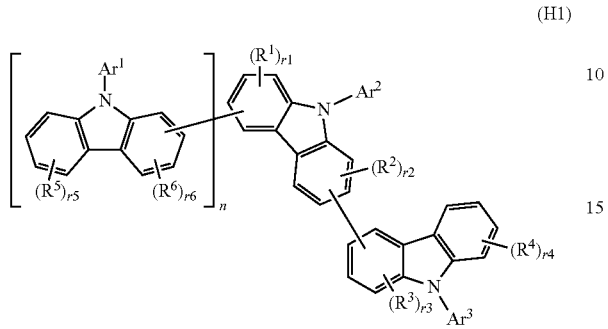

(H1)

wherein $R^1$, $R^2$, $R^3$, $R^4$, $R^5$, and $R^6$ may be the same or different fluorine atom, chlorine atom, a deuterium atom, a cyano group, a trifluoromethyl group, a nitro group, linear or branched $C_1$-$C_6$alkyl group, $C_5$-$C_{10}$cyclo-alkyl group, linear or branched $C_1$-$C_6$alkoxy group, $C_5$-$C_{10}$cyclo-alkoxy group, substituted or unsubstituted aromatic hydrocarbon group, substituted or unsubstituted aromatic heterocyclic group, substituted or unsubstituted condensed polycyclic aromatic group, r1, r4, r5 is 0, 1, 2, 3, or 4, r2, r3, r6 is 0, 1, 2 or 3, n is 0 or 1, and $Ar^1$, $Ar^2$, and $Ar^3$ may be the same or different, substituted or unsubstituted aromatic hydrocarbon group, substituted or unsubstituted aromatic heterocyclic group, substituted or unsubstituted condensed polycyclic aromatic group, deuterium substituted aromatic hydrocarbon group, deuterium substituted aromatic heterocyclic group, or deuterium substituted condensed polycyclic aromatic group.

When $Ar^1$, $Ar^2$, or $Ar^3$ is a substituted aromatic hydrocarbon group, a substituted aromatic heterocyclic group, or a substituted polycyclic aromatic group, the substitution groups can be any non-carbon or carbon-containing functional group, such as, an aromatic hydrocarbon group, an aromatic heterocyclic group or a polycyclic aromatic group. For example, the substitution group on the aromatic ring structure of $Ar^1$, $A^2$, or $Ar^3$ can be

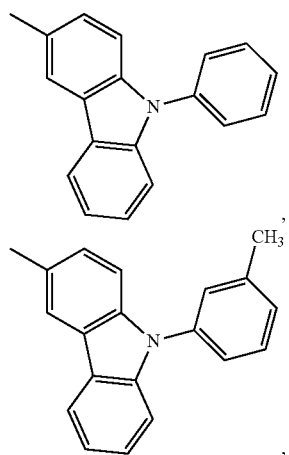

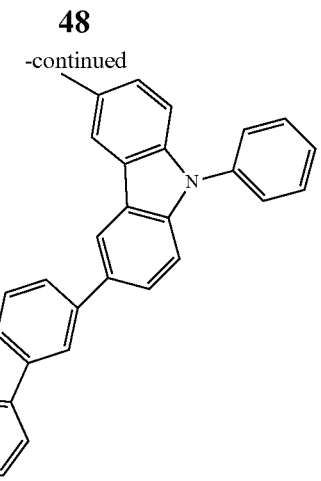

or the like.

Especially suitable are the compounds (H1-1), (H1-2), (H1-7) as mentioned below and the compounds (H1-3), (H1-4), (H1-5), (H1-6), (H1-8), (H1-9), (H1-10), (H1-11), (H1-12), (H1-13), (H1-14), (H1-14), (H-16) and (H1-17) as described in WO 2013/112557.

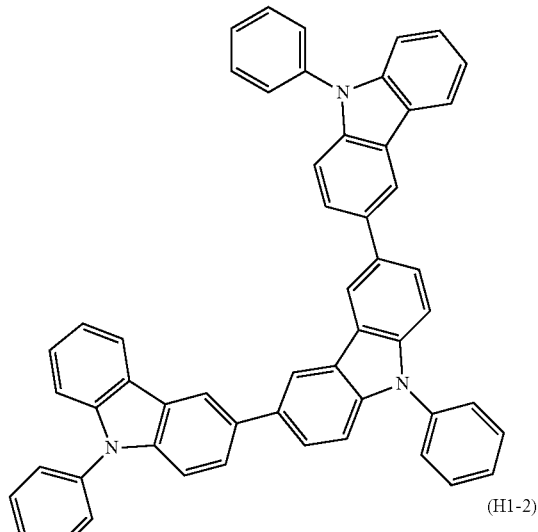

(H1-1)

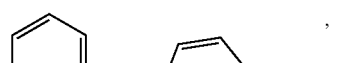

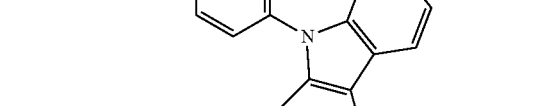

(H1-2)

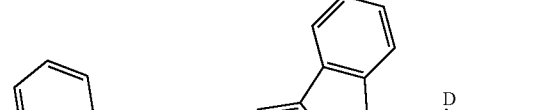

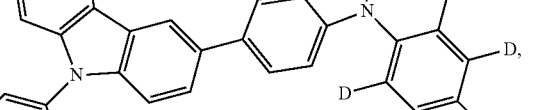

(H1-7)

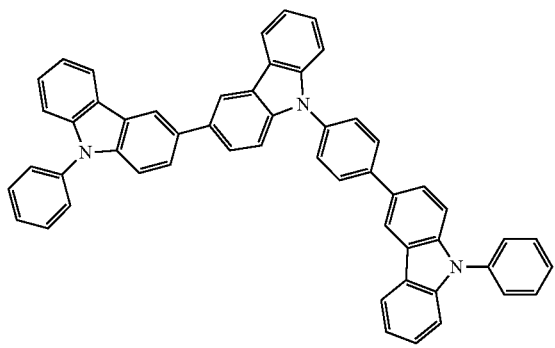

Further suitable host materials which may be employed together with the host material mentioned before are host materials containing at least one of the following groups in the molecule:

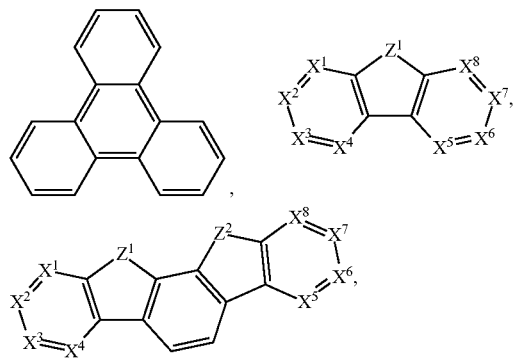

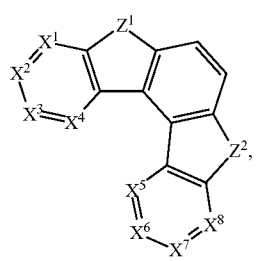

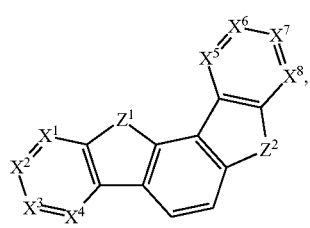

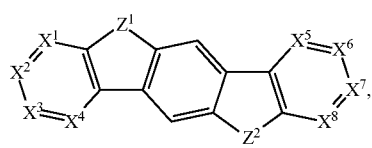

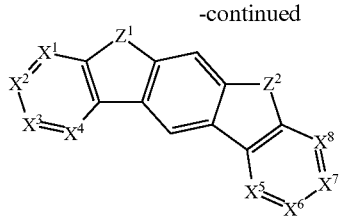

wherein $X^1$ to $X^8$ is selected from C or N; and wherein $Z^1$ and $Z^2$ is S or O.

The groups mentioned above may be unsubstituted or substituted by an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C=CHC_nH_{2n+1}$, A1, $Ar_1-Ar_2$, $C_nH_{2n-Ar1}$, wherein n is 1, 2, 3, 4, 5, 6, 7, 8, 9, or 10, and wherein $Ar_1$ and $Ar_2$ are independently selected from the group consisting of benzene, biphenyl, naphthalene, triphenylene, carbazole, and heteroaromatic analogs thereof.

Further suitable host compounds are compounds comprising a triphenylene containing benzo-fused thiophene. A combination of benzo-fused thiophenes and triphenylene as hosts in OLEDs may be beneficial. Therefore combining these two moieties in one molecule may offer improved charge balance which may improve device performance in terms of lifetime, efficiency and low voltage. Different chemical linkage of the two moieties can be used to tune the properties of the resulting compound to make it the most appropriate for a particular phosphorescent emitter, device architecture, and/or fabrication process. For example, m-phenylene linkage is expected to result in higher triplet energy and higher solubility whereas -phenylene linkage is expected to result in lower triplet energy and lower solubility.

Similar to the characterization of benzo-fused thiophenes, benzo-fused furans are also suitable host materials. Examples of benzo-fused furans include benzofuran and dibenzofuran. Therefore, a material containing both triphenylene and benzofuran may be advantageously used as host material in OLEDs. A compound containing both of these two groups may offer improved electron stabilization which may improve device stability and efficiency with low voltage. The properties of the triphenylene containing benzofuran compounds may be tuned as necessary by using different chemical linkages to link the triphenylene and the benzofuran.

Benzo-fused furans are benzofurans and dibenzofurans. Benzo-fused thiophenes are benzothiophenes and dibenzothiophenes.

The benzo-fused thiophene and benzo-fused furans mentioned above may be unsubstituted or substituted for example by one or more unfused substituents independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C=CHC_nH_{2n+1}$, $A_1$, $Ar_1$-$Ar_2$, $C_nH_{2n-Ar1}$, wherein n is 1, 2, 3, 4, 5, 6, 7, 8, 9, or 10, and wherein $Ar_1$ and $Ar_2$ are independently selected from the group consisting of benzene, biphenyl, naphthalene, triphenylene, carbazole, and heteroaromatic analogs thereof.

The substituents of the compounds described above are unfused such that the substituents are not fused to the triphenylene, benzo-fused furan or benzo-fused thiophene moieties of the compound. The substituents may optionally be inter-fused (i.e. fused to each other).

The benzo-fused thiophene and benzo-fused furans mentioned above are for example described in WO 2013/112557 and in WO 2009/021126.

Further suitable host materials for phosphorescent green to red emitters are mentioned in US 20130181190, especially in table 3, and US 20130119354, especially in table 4.

Specific examples of organic compounds which can be used for the host material include compounds such as

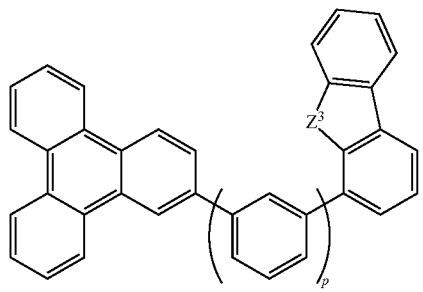

wherein $Z^3$ is O or S and p is 0 or 1, such as

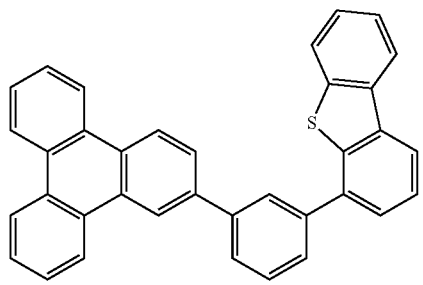

or

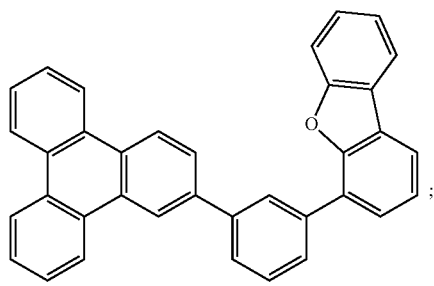

;

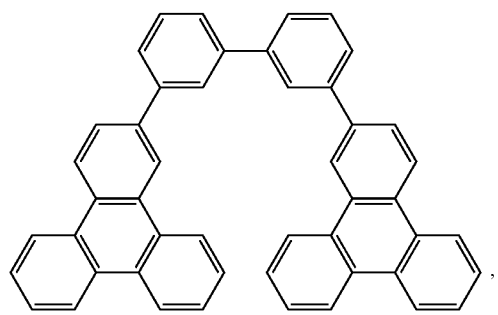

,

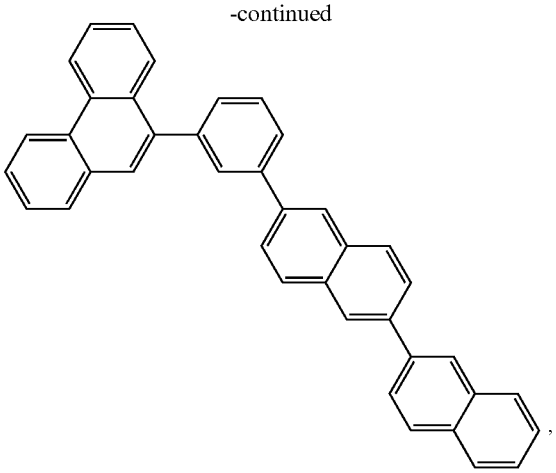

,

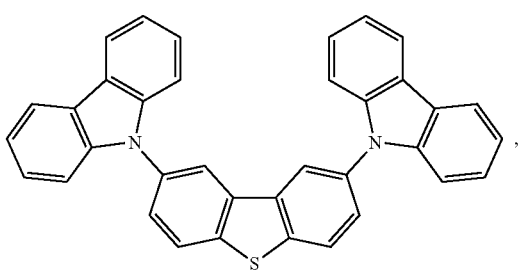

,

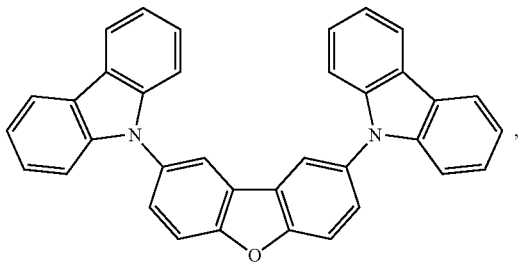

,

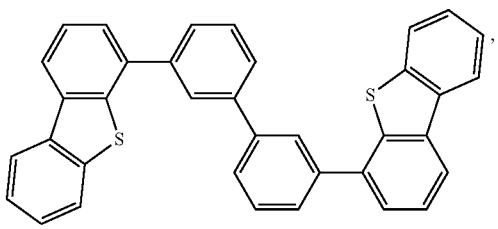

,

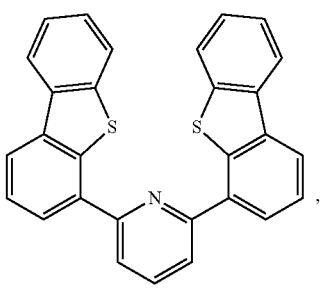

,

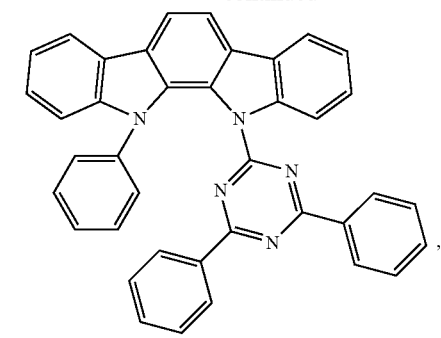

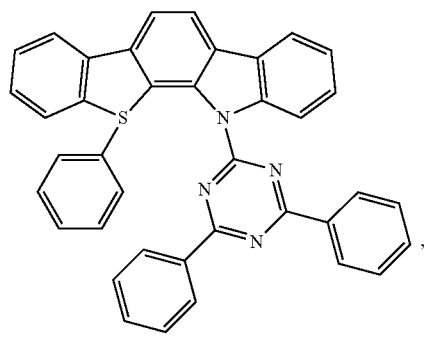

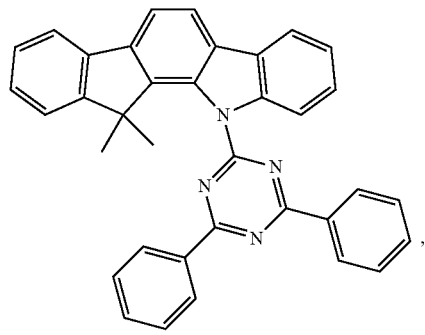

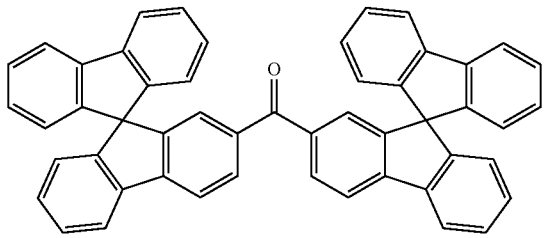

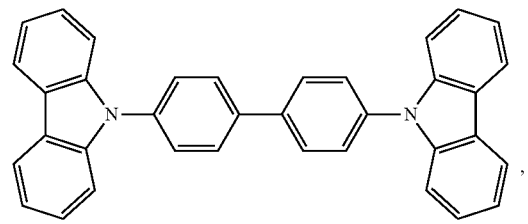

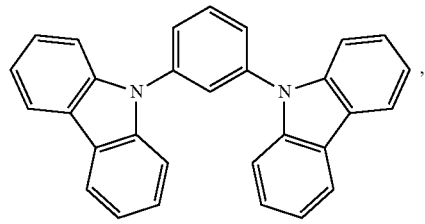

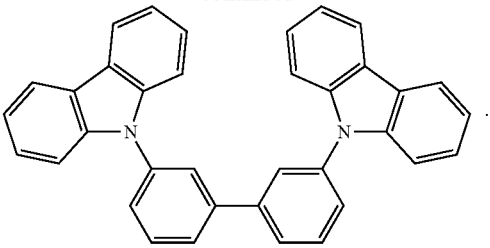 [SMILES: c1cc(-c2cccc(-n3c4ccccc4c4ccccc43)c2)cc(-n2c3ccccc3c3ccccc32)c1]

The host compound can be one compound or it can be a mixture of two or more compounds. Suitable mixtures are for example the binary hosts systems as described in WO 2011/136755 And WO 2013/112557.

Further suitable as host material are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and the host materials specified in the following applications: WO2008/034758, WO2009/003919.

Further suitable host materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co)polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709 and European patent applications EP12175635.7 and EP12185230.5 and EP12191408.9 (in particular page 25 to 29 of EP12191408.9).

In a particularly preferred embodiment, one or more compounds of the general formula (A) specified hereinafter are used as host material.

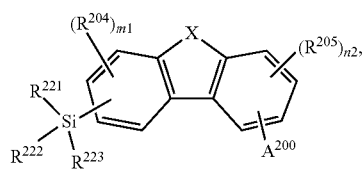
(A)

wherein
X is NR, S, O or PR;
R is aryl, heteroaryl, alkyl, cycloalkyl, or heterocycloalkyl;
$A^{200}$ is $-NR^{206}R^{207}$, $-P(O)R^{208}R^{209}$, $-PR^{210}R^{211}$, $-S(O)_2R^{212}$, $-S(O)R^{213}$, $-SR^{214}$, or $-OR^{215}$;
$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl;
$R^{224}$ and $R^{225}$ are independently of each other alkyl, cycloalkyl, heterocycloalkyl, aryl, heteroaryl, a group $A^1$, or a group having donor, or acceptor characteristics;
n2 and m1 are independently of each other 0, 1, 2, or 3;
$R^{206}$, $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocycloalkyl.

Compounds of formula (A) and their preparation processes, such as, for example,

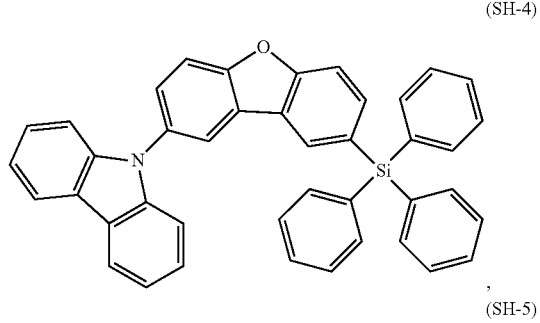
(SH-4)

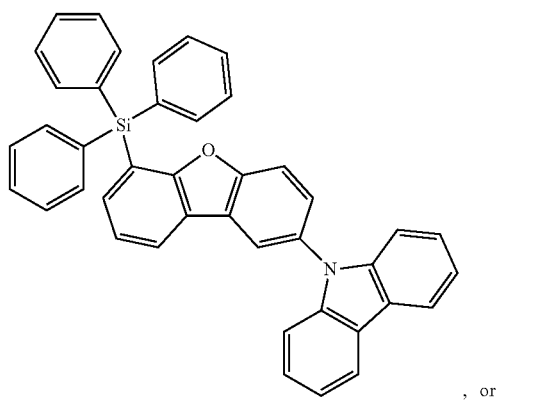
(SH-5)

, or

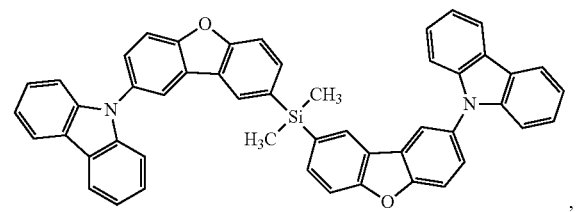
(SH-6)

are described in WO 2010/079051 A1 (in particular pages on 19 to 26 and in tables on pages 27 to 34, pages 35 to 37 and pages 42 to 43).

Additional host materials on basis of dibenzofurane are, for example, described in US 2009066226, EP1 885 818 B1, EP 1 970 976, EP 1 998 388 and EP 2 034 538. Examples of particularly preferred host materials are shown below:

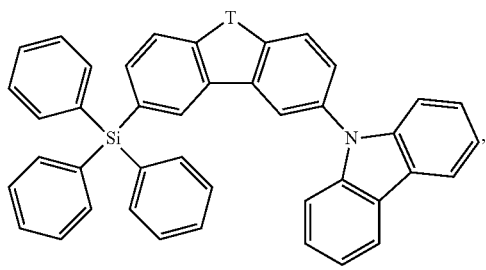

-continued
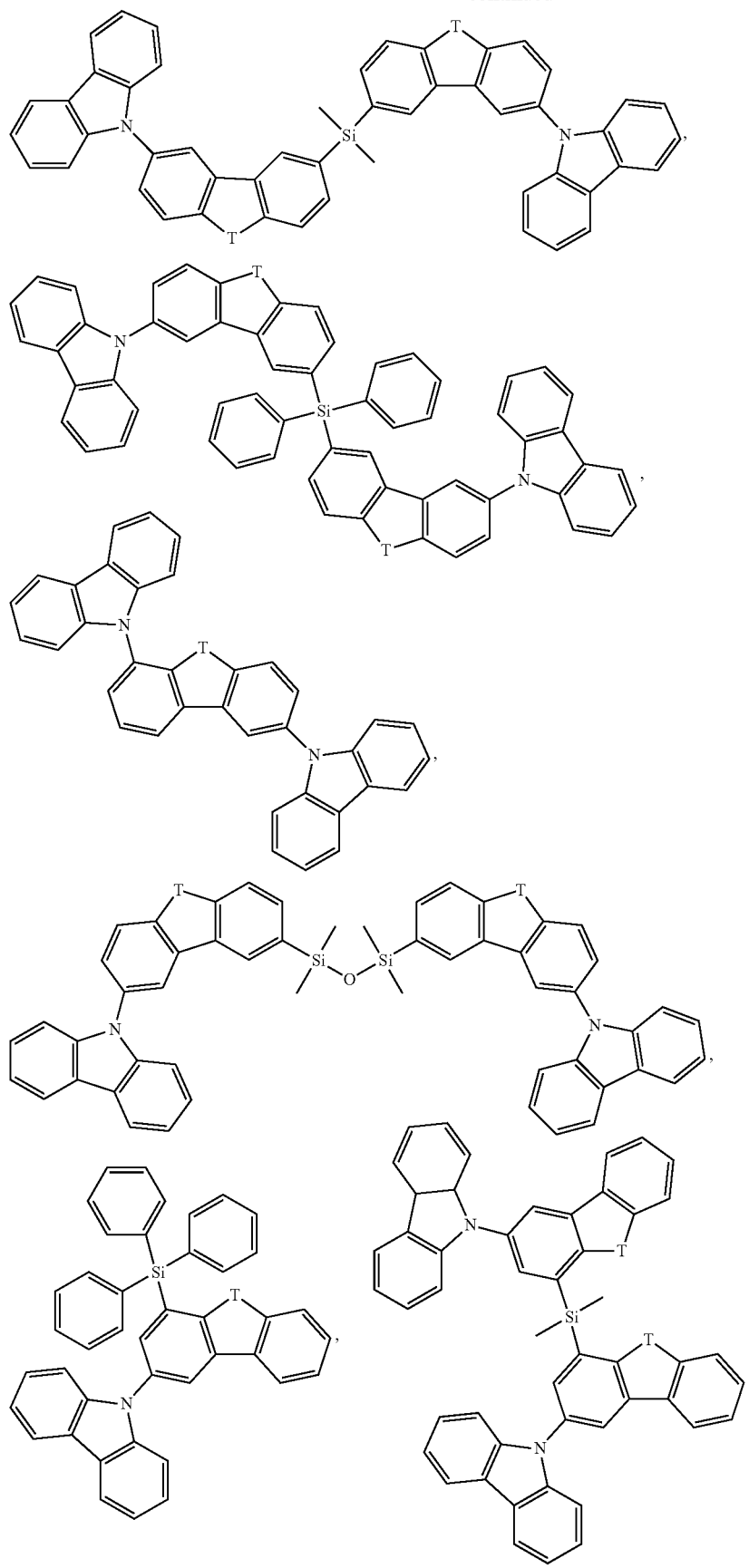

-continued
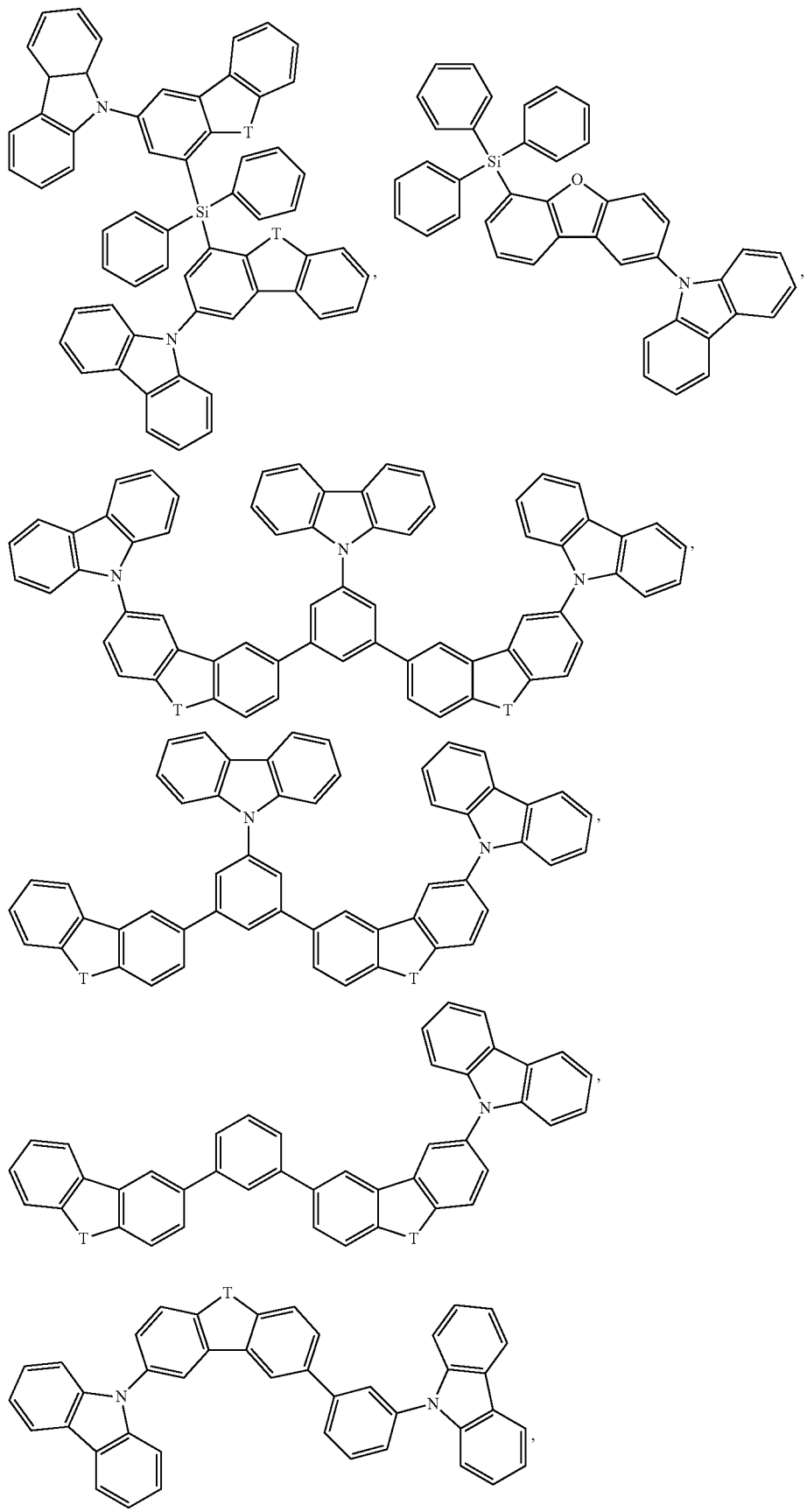

-continued
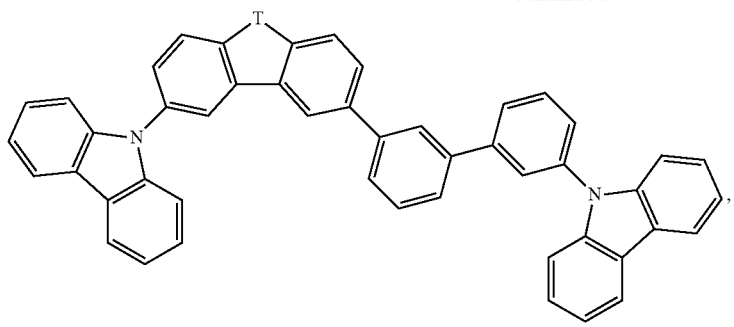
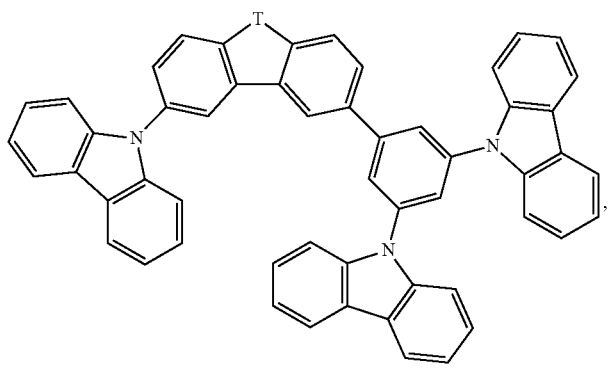
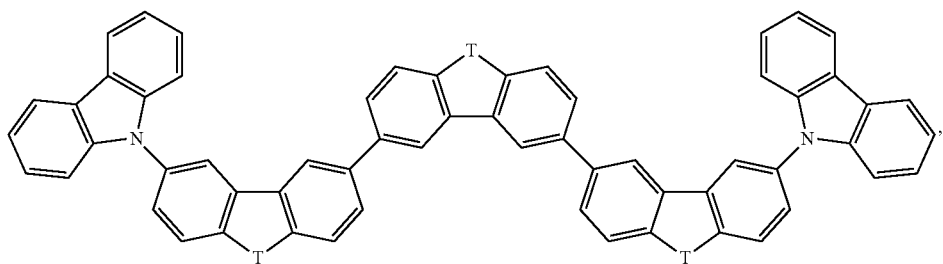
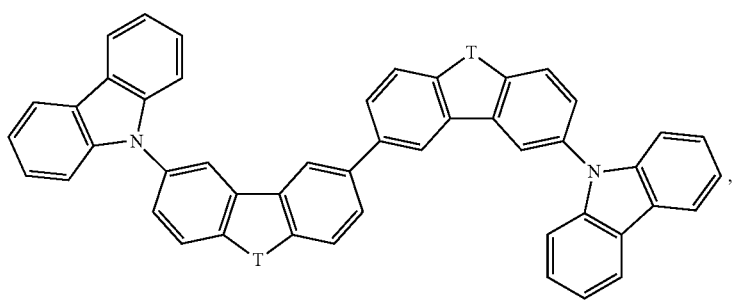
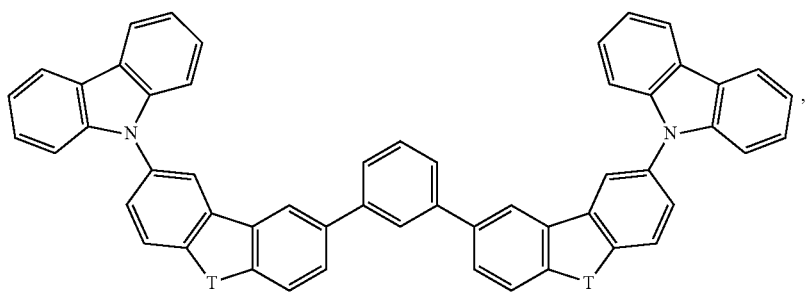

-continued
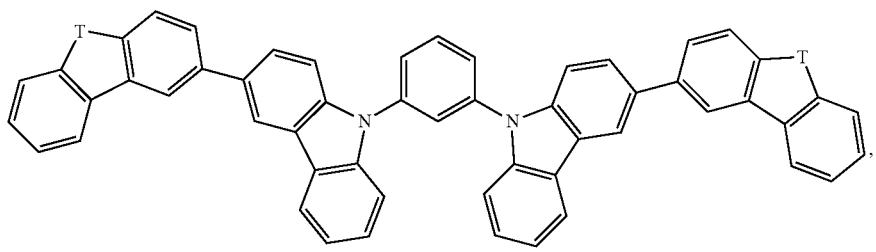
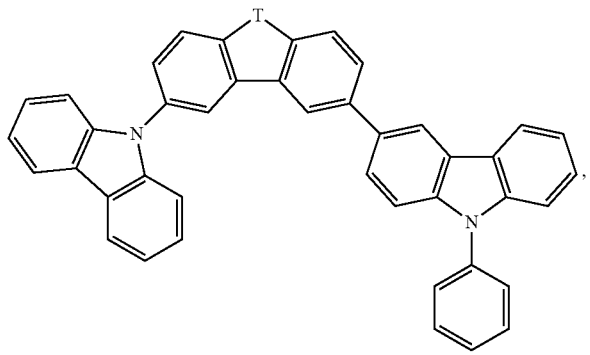
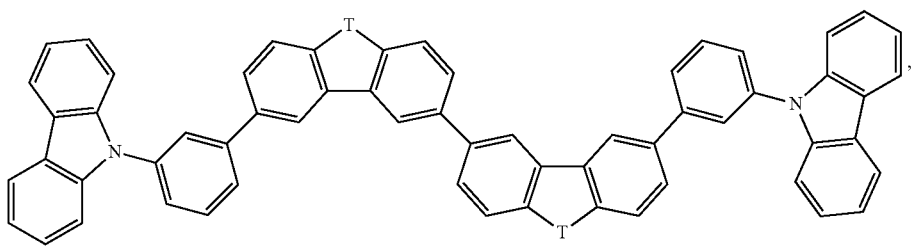
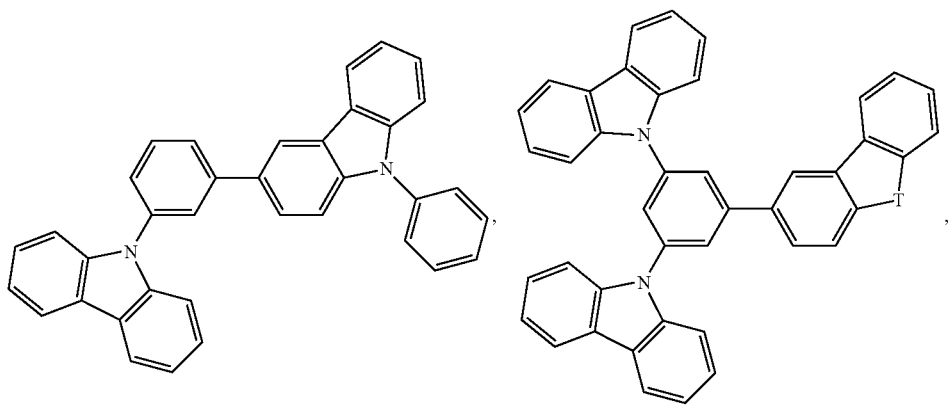
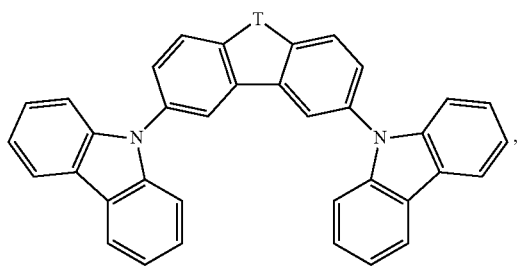

-continued
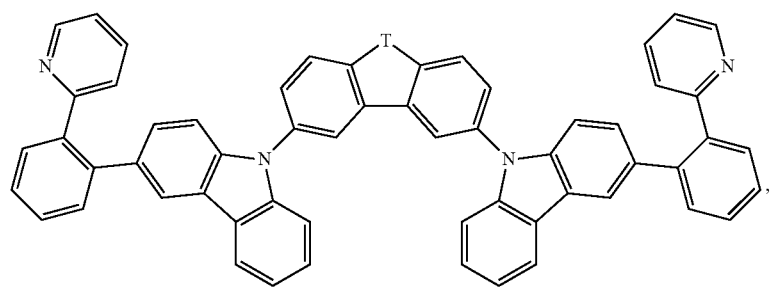
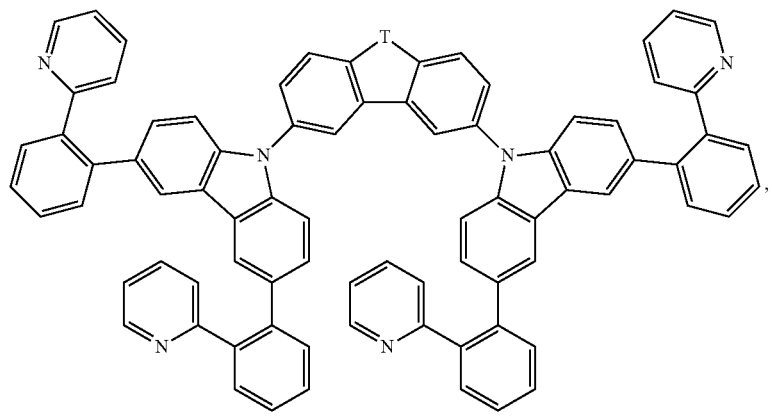
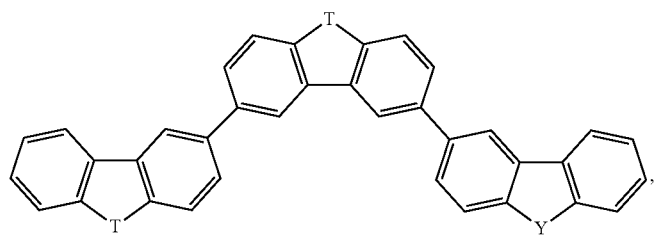
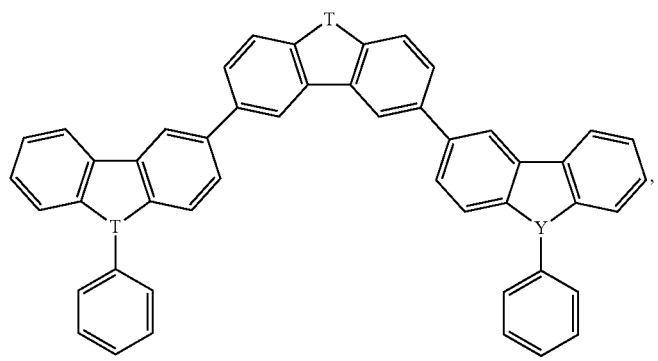
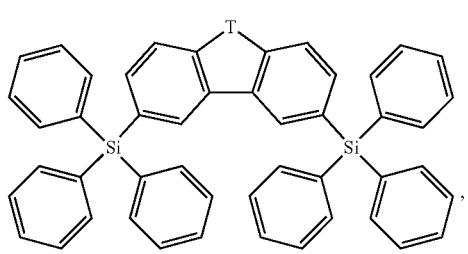
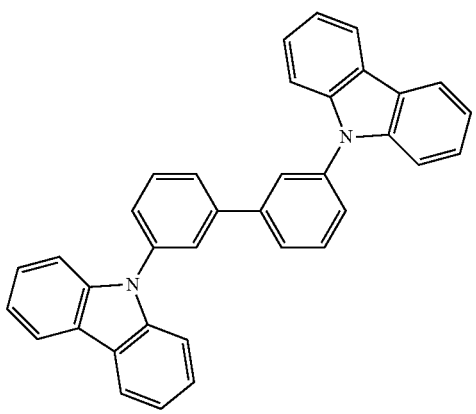

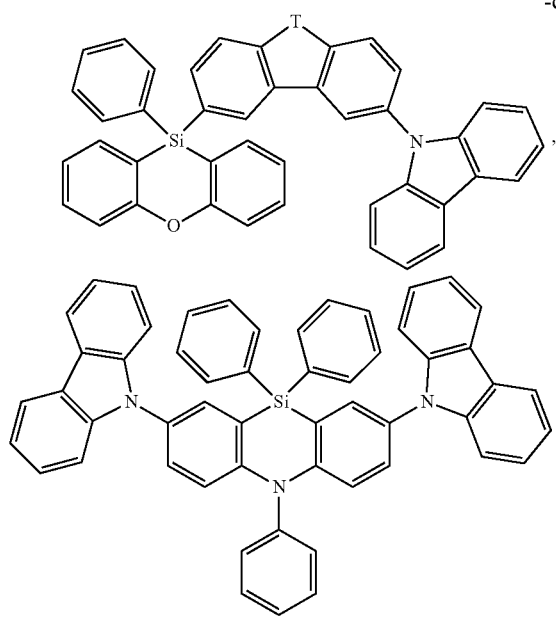
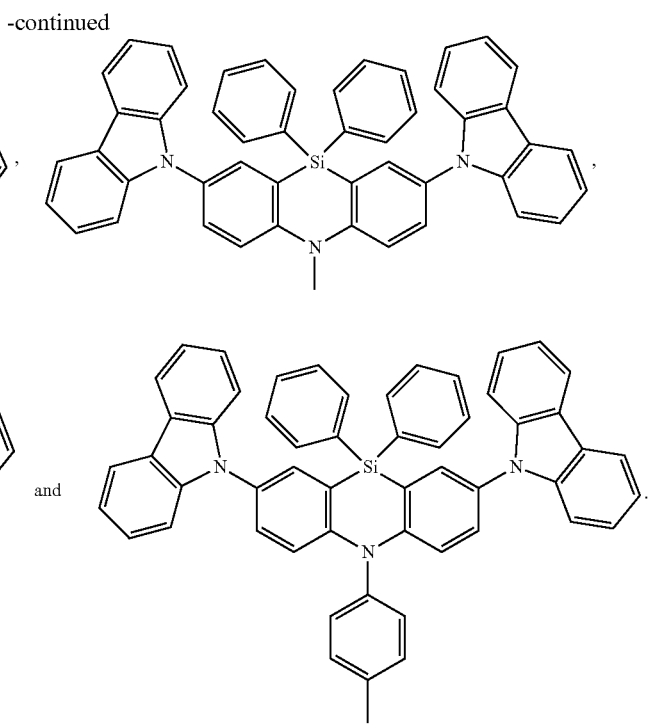

In the above-mentioned compounds T is O, or S, preferably O. If T occurs more than one time in a molecule, all groups T have the same meaning.

In a preferred embodiment, the light-emitting layer (e) comprises the emitter in an amount of 2 to 40% by weight, preferably 5 to 35% by weight, more preferably 5 to 20% by weight and the host compound in an amount of 60 to 98% by weight, preferably 65 to 95% by weight, more preferably 80 to 95% by weight, where the amount of the phosphorescent emitter and the host compound adds up to a total of 100% by weight. The emitter may be one emitter or a combination of two ore more emitters. The host may be one host or a combination of two or more hosts.

Anode (a)

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

Hole Injection Layer (b)

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS. Further suitable hole injection materials are mentioned in US 2013/0181190, especially in table 3, and US 20130119354, especially in table 4.

Hole Transport Layer (c)

Either hole-transporting molecules or polymers may be used as the hole transport material. Suitable hole transport materials for layer (c) of the inventive OLED are disclosed, for example, in Kirk-Othmer Encyclopedia of Chemical Technology, 4th Edition, Vol. 18, pages 837 to 860, 1996, US20070278938, US2008/0106190, US2011/0163302 (triarylamines with (di)benzothiophen/(di)benzofuran; Nan-Xing Hu et al. Synth. Met. 111 (2000) 421 (indolocarbazoles), WO2010/002850 (substituted phenylamine compounds), WO2012/16601 (in particular the hole transport materials mentioned on pages 16 and 17 of WO2012/

16601), US 20130181190, especially in table 3, and US 20130119354, especially in table 4. Combination of different hole transport material may be used. Reference is made, for example, to WO2013/022419, wherein
(HTL1-1)
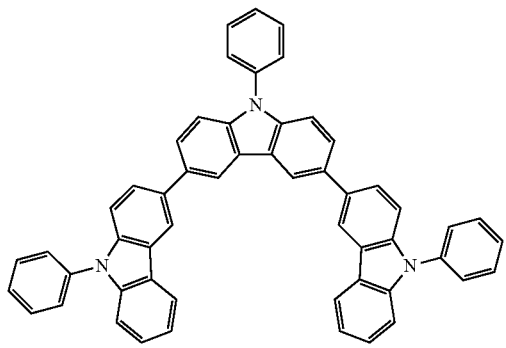
and
(HTL2-1)
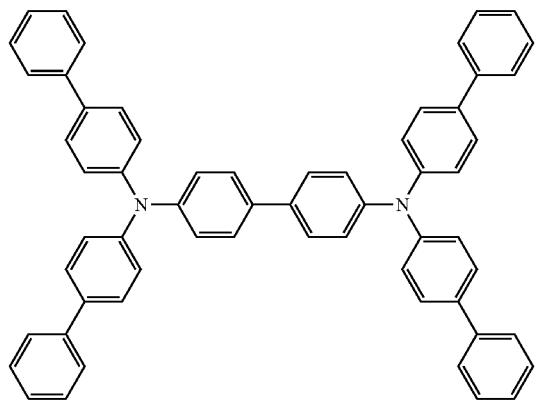 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
constitute the hole transport layer.
Customarily used hole-transporting molecules are selected from the group consisting of
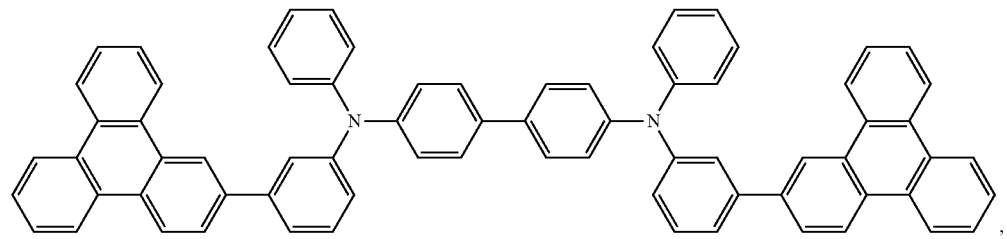
,
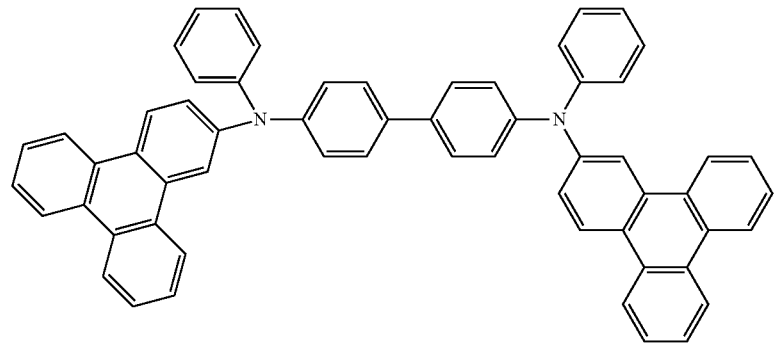
,
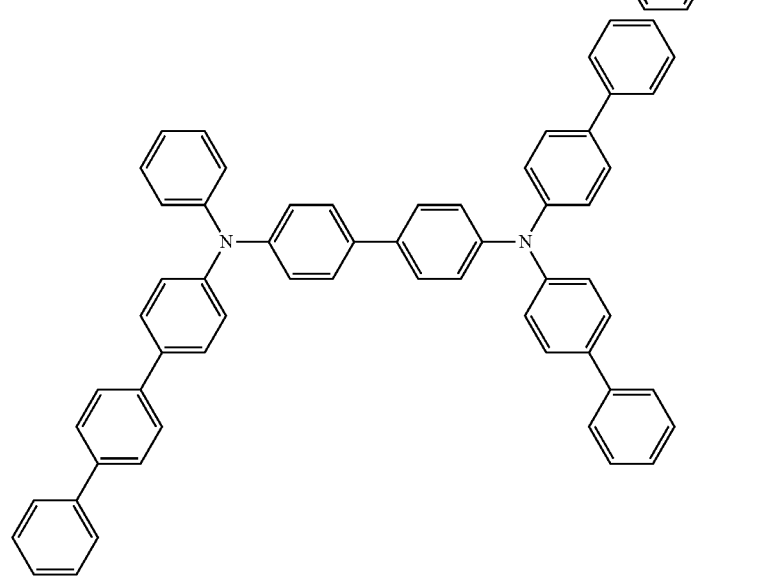

71

(4-phenyl-N-(4-phenylphenyl)-N-[4-[4-(N-[4-(4-phenyl-phenyl)phenyl]anilino)phenyl]phenyl]aniline),

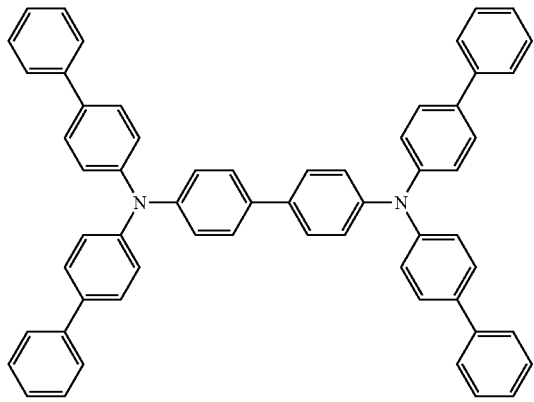

(4-phenyl-N-(4-phenylphenyl)-N-[4-[4-(4-phenyl-N-(4-phenylphenyl)anilino)phenyl]phenyl]aniline),

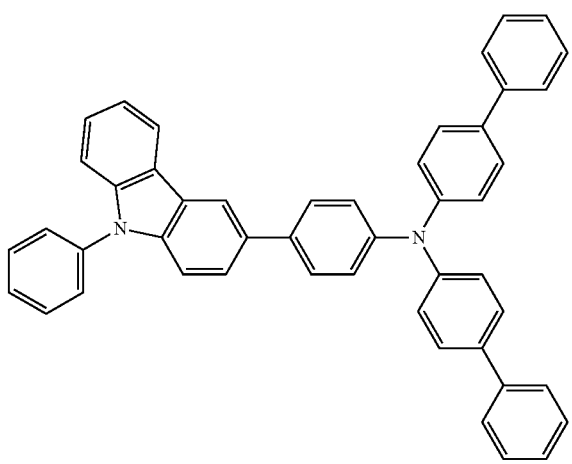 [SMILES: c1ccc(-c2ccc(N(c3ccc(-c4ccccc4)cc3)c3ccc(-c4ccc5c(c4)c4ccccc4n5-c4ccccc4)cc3)cc2)cc1]

(4-phenyl-N-[4-(9-phenylcarbazole-3-yl)phenyl]-N-(4-phenylphenyl)aniline),

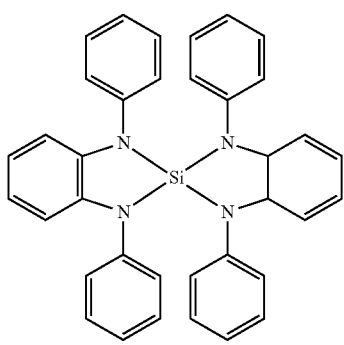 [SMILES: C1=CC2C(C=C1)N(c1ccccc1)[Si]1(N(c3ccccc3)c3ccccc3N1c1ccccc1)N2c1ccccc1]

72

(1,1',3,3'-tetraphenylspiro[1,3,2-benzodiazasilole-2,2'-3a,7a-dihydro-1,3,2-benzodiazasilole]),

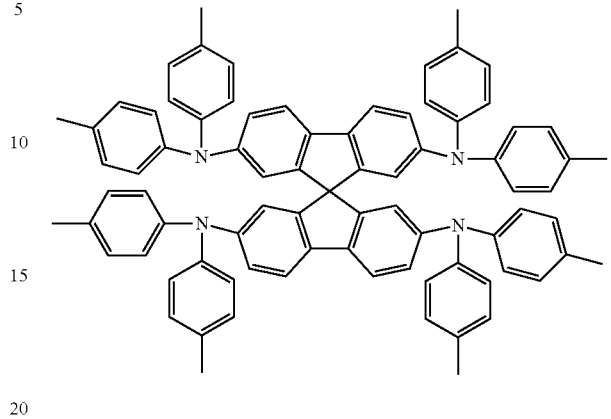

(N2,N2,N2',N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-diphenyl-N,N'-bis(3-methylphenyl)-[1,1-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)$_2$-methylphenyl](4-methylphenyl)methane (MPMP), 1-phenyl-3-[p-(diethylamino)styryl]5-[p-(diethylamino)phenyl]pyrazoline (PPR or DEASP), 1,2-trans-bis(9H-carbazol9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolypamino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

In a preferred embodiment it is possible to use metal carbene complexes as hole transport materials. Suitable carbene complexes are, for example, carbene complexes as described in WO2005/019373A2, WO2006/056418 A2, WO2007/115970, WO2007/115981, WO2008/000727, WO2012/121936A2, US2012/0305894A1, and WO2012/172482A1. One example of a suitable carbene complex is Ir(DPBIC)$_3$ (HTM-1). Another example of a suitable carbene complex is Ir(ABIC)$_3$ (HTM-2). The formulae of (HTM-1) and (HTM-2) are mentioned above.

Further compounds suitable as hole transport material are for example mentioned in WO 2013/112557, e.g. the following compounds 1a to 12a mentioned in WO 2013/112557:

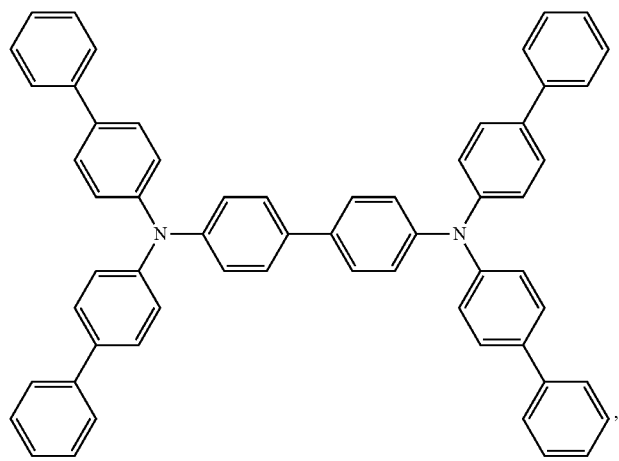
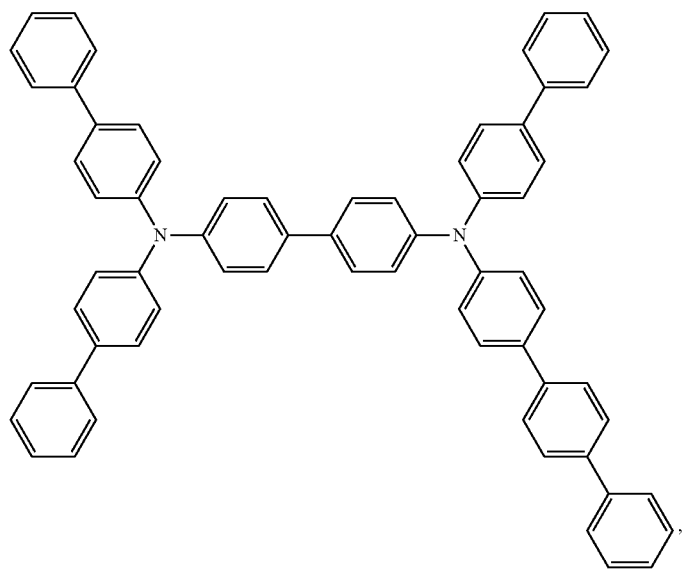
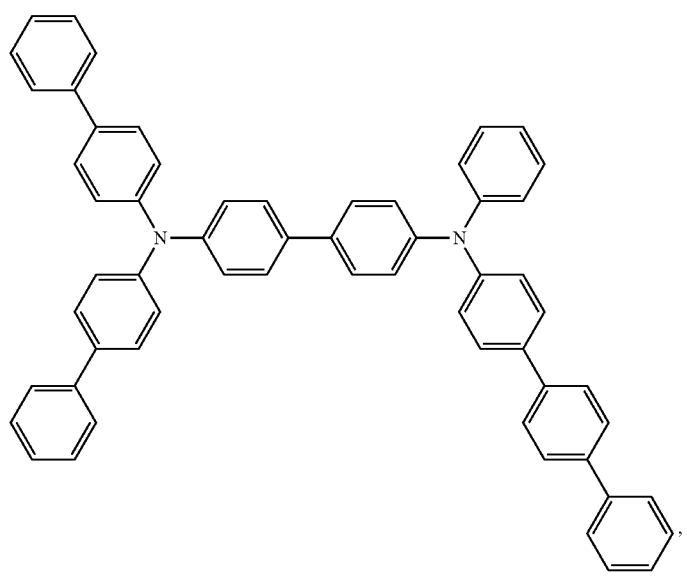

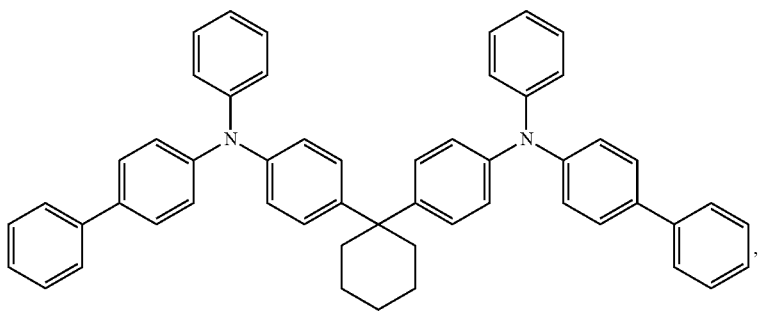
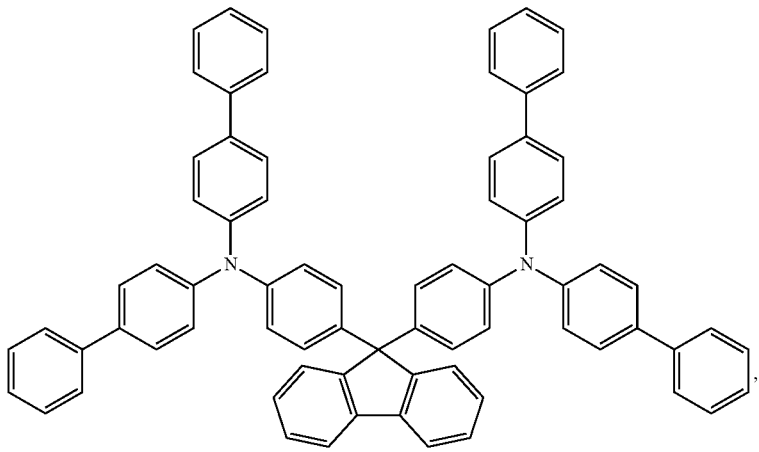
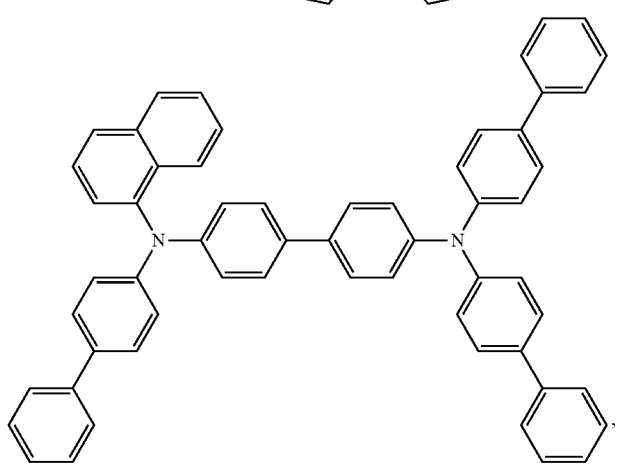
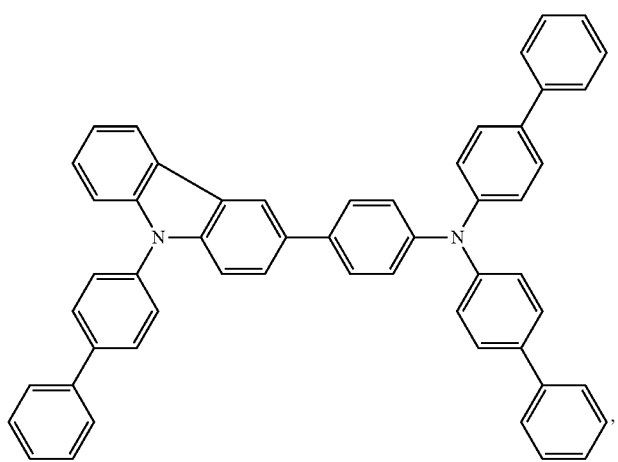

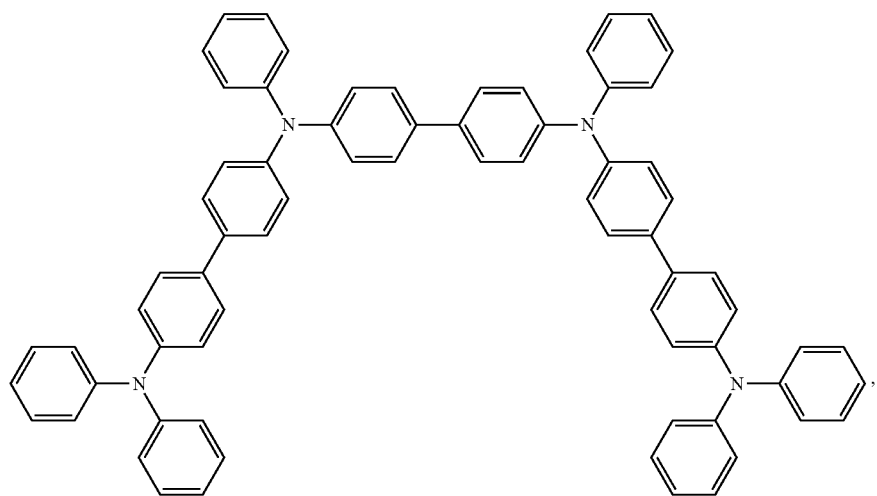
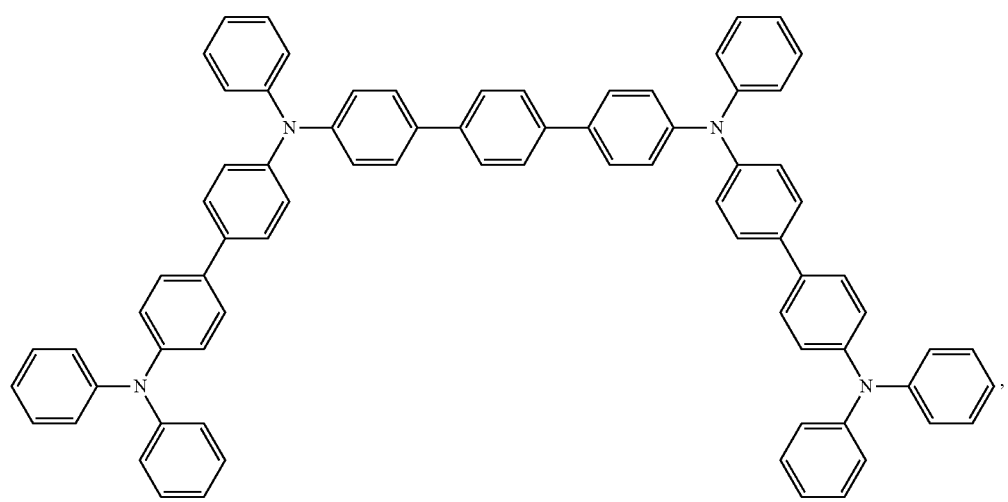
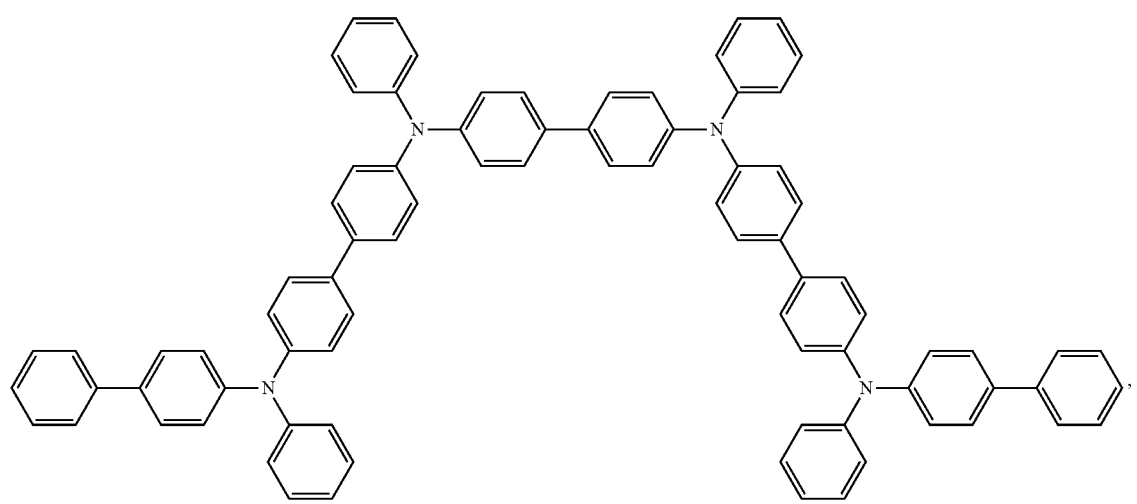

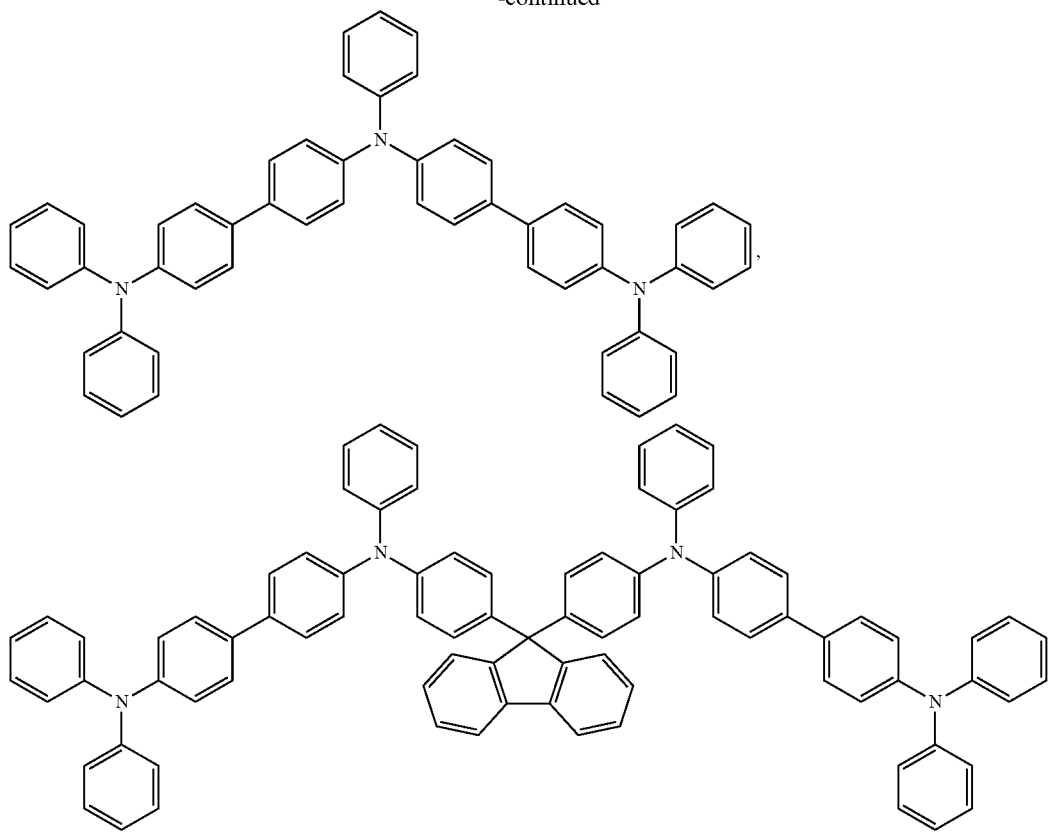

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, 2003, 359 (p-doped organic layers); A. G. Werner, F. Li, K. Harada, M. Pfeiffer, T. Fritz, K. Leo, Appl. Phys. Lett., Vol. 82, No. 25, 2003, 4495 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WO_x$, $ReO_3$ and/or $V_2O_5$, preferably $MoO_3$ and/or $ReO_3$, more preferably $MoO_3$, or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho2,6-quinodimethane, 2-fluoro-7,7,8,8-tetracyanoquino-dimethane, 2,5-difluoro-7,7,8,8etracyanoquinodimethane, di-cyanomethylene-1,3,4,5,7,8-hexafluoro-6Hnaphthalen-2-ylidene)malononitrile ($F_6$-TNAP), $Mo(tfd)_3$ (from Kahn et al., J. Am. Chem. Soc. 2009, 131 (35), 12530-12531), compounds as described in EP1988587, US2008265216, EP2180029, US20100102709, WO2010132236, EP2180029 and quinone compounds as mentioned in EP2401254.

Electron/Exciton Blocking Layer (d)

Blocking layers may be used to reduce the number of charge carriers (electrons or holes) and/or excitons that leave the emissive layer. An electron/exciton blocking layer (d) may be disposed between the emitting layer (e) and the hole transport layer (c), to block electrons from emitting layer (e) in the direction of hole transport layer (c). Blocking layers may also be used to block excitons from diffusing out of the emissive layer. Suitable metal complexes for use as electron/exciton blocker material are, for example, carbene complexes as described in WO2005/019373A2, WO2006/056418 A2, WO2007/115970, WO2007/115981, WO2008/000727, WO2012/121936A2, US2012/0305894A1, and WO2012/172482A1. Explicit reference is made here to the disclosure of the WO applications cited, and these disclosures shall be considered to be incorporated into the content of the present application. One example of a suitable carbene complex is compound HTM-1. Another example of a suitable carbene complex is compound HTM-2. The formulae of (HTM-1) and (HTM-2) are mentioned above.

Also suitable as electron/exciton blocker materials are the compounds mentioned in WO2012/130709; WO2013/050401; WO2014/009317; WO2014/044722; and the non-published European Patent Application EP13191100.0.

Further suitable electron/exciton blocker materials are the compounds of formula (H1) mentioned in WO 2013/112557, as described above.

Especially suitable are the compounds (H1-1), (H1-2), (H1-7) as mentioned above and the compounds (H1-3), (H1-4), (H1-5), (H1-6), (H1-8), (H1-9), (H1-10), (H1-11), (H1-12), (H1-13), (H1-14), (H1-14), (H-16) and (H1-17) as described in WO 2013/112557.

Hole/Exciton Blocking Layer (f)

Blocking layers may be used to reduce the number of charge carriers (electrons or holes) and/or excitons that leave the emissive layer. The hole blocking layer may be disposed between the emitting layer (e) and electron transport layer (g), to block holes from leaving layer (e) in the direction of electron transport layer (g). Blocking layers may also be used to block excitons from diffusing out of the emissive layer. Suitable hole/exciton blocking materials are, in principle, the host compounds mentioned above. The same preferences apply as for the host material.

Suitable hole/exciton blocker materials are therefore for example the materials containing both triphenylene and benzo-fused furans or benzo-fused thiophenes as mentioned above concerning suitable host materials.

Further hole/exciton blocking materials are one or more compounds of the general formula (X)

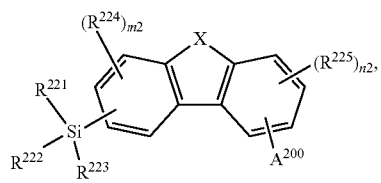

(X)

wherein

X is NR, S, O or PR;

R is aryl, heteroaryl, alkyl, cycloalkyl, or heterocycloalkyl;

$A^{200}$ is $-NR^{206}R^{207}$, $-P(O)R^{208}R^{209}$, $-S(O)_2R^{212}$, $-S(O)R^{213}$, $-SR^{214}$, or $-OR^{215}$;

$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl;

$R^{224}$ and $R^{225}$ are independently of each other alkyl, cycloalkyl, heterocycloalkyl, aryl, heteroaryl, a group $A^{200}$, or a group having donor, or acceptor characteristics;

n2 and m2 are independently of each other 0, 1, 2, or 3;

$R^{206}$ and $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocycloalkyl.

Compounds of formula (X) are described in WO2010079051 (in particular pages on 19 to 26 and in tables on pages 27 to 34, pages 35 to 37 and pages 42 to 43).

Further suitable hole/exciton blocker materials are mentioned in US 20130181190, especially in table 3, and US 20130119354, especially in table 4.

Examples are bathocuprine compounds such as:

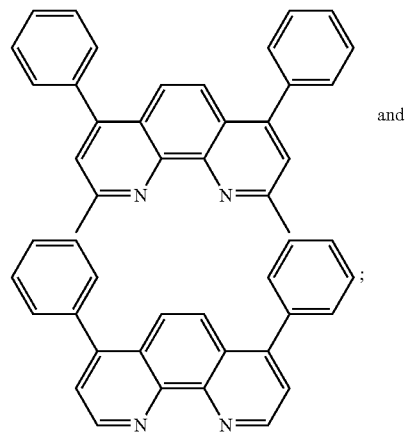

and metal-8-hydroxy-quinolates such as:

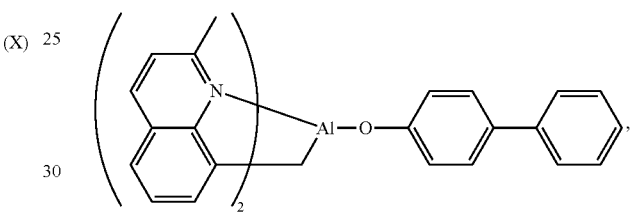

triazoles, oxadiazoles, imidazoles, benzoimidazoles, triphenylene compounds, fluorinated aromatic compounds, phenothiazine-S-oxides, silylated five-membered nitrogen, oxygen, sulfur or phosphorous dibenzoheterocycles, or Azacarbazoles.

Further examples for hole/exciton blocker materials are for example

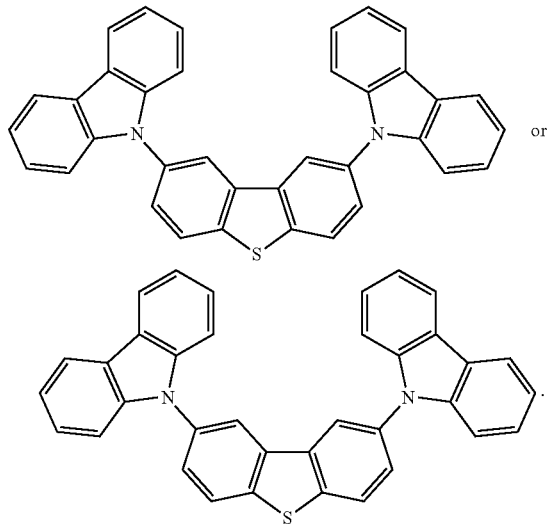

or

Electron Transport Layer (g)

Electron transport layer may include a material capable of transporting electrons. Electron transport layer may be intrinsic (undoped), or doped. Doping may be used to enhance conductivity. Suitable electron-transporting materials for layer (g) of the inventive OLEDs comprise metals chelated with oxinoid compounds, such as tris(8-hydroxyquinolato)aluminum ($Alq_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

4,7-diphenyl-1,10-phenanthroline (Bphen):

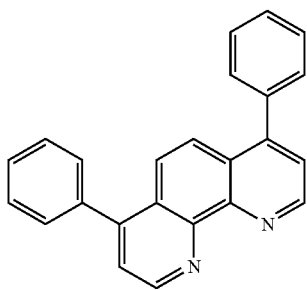 [SMILES: c1ccc(-c2ccnc3c2ccc2c(-c4ccccc4)ccnc23)cc1]

Further suitable are dibenzofuran compounds A-1 to A-36 and B-1 to B-22 described in WO2011/157790 are preferred, wherein dibenzofuran compound

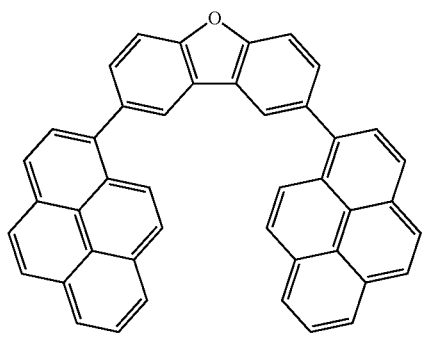 [SMILES: c1cc2ccc3ccc(-c4ccc5oc6ccc(-c7ccc8ccc9cccc%10ccc7c8c9%10)cc6c5c4)c4ccc(c1)c2c34]

(A-10; =ETM-1) is most preferred.

It is likewise possible to use mixtures of at least two materials in the electron-transporting layer, in which case at least one material is electron-conducting. Preferably, in such mixed electron-transporting layers, at least one phenanthroline compound is used, preferably BCP, or at least one pyridine compound according to the formula (VIII) below, preferably a compound of the formula (VIIIa) below. More preferably, in mixed electron-transporting layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII). Reference is made to WO2011/157779.

The electron-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transporting layer. n-Doping is achieved by the addition of reducing materials. These mixtures may, for example, be mixtures of the above-mentioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $R^b{}_2CO_3$, dipotassium phthalate, $W(hpp)_4$ from EP1786050, or with compounds described in EP1837926B1, EP1837927, EP2246862, WO2010132236 and DE102010004453.

In a preferred embodiment, the electron-transporting layer comprises at least one compound of the general formula (VII)

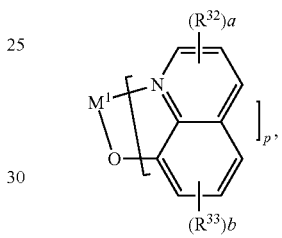

in which $R^{32}$ and $R^{33}$ are each independently F, $C_1$-$C_8$-alkyl, or $C_6$-$C_{14}$-aryl, which is optionally substituted by one or more $C_1$-$C_8$-alkyl groups, or two $R^{32}$ and/or $R^{33}$ substituents together form a fused benzene ring which is optionally substituted by one or more $C_1$-$C_8$-alkyl groups;

a and b are each independently 0, or 1, 2 or 3,

M' is an alkaline metal atom or alkaline earth metal atom, p is 1 when $M^1$ is an alkali metal atom, p is 2 when $M^1$ is an earth alkali metal atom.

A very particularly preferred compound of the formula (VII) is

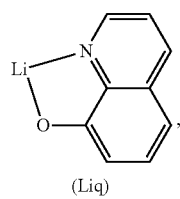

(Liq)

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transporting layer comprises at least one compound of the formula (VIII),

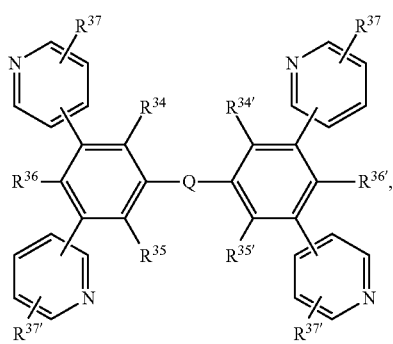
(VIII)

in which $R^{34}$, $R^{35}$, $R^{36}$, $R^{37}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G, Q is an arylene or heteroarylene group, each of which is optionally substituted by G;

D is —CO—; —COO—; —S—; —SO—; —SO$_2$—; —O—; —NR$^{40}$—; —SiR$^{45}$R$^{46}$; —POR$^{47}$—; —CR$^{38}$=CR$^{39}$—; or —C≡C—;

E is —OR$^{44}$; —SR$^{44}$; —NR$^{40}$R$^{41}$; —COR$^{43}$; —COOR$^{42}$; —CONR$^{49}$R$^{41}$; —CN; or F;

G is E, $C_1$-$C_{18}$-alkyl, $C_1$-$C_{18}$-alkyl which is interrupted by D, $C_1$-$C_{18}$-perfluoroalkyl, $C_1$-$C_{18}$-alkoxy, or $C_1$-$C_{18}$-alkoxy which is substituted by E and/or interrupted by D, in which $R^{38}$ and $R^{39}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;

$R^{40}$ and $R^{41}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or $R^{40}$ and $R^{41}$ together form a 6-membered ring;

$R^{42}$ and $R^{43}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{44}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{45}$ and $R^{46}$ are each independently $C_1$-$C_{18}$-alkyl, $C_6$-$C_{18}$-aryl or $C_6$-$C_{18}$-aryl which is substituted by $C_1$-$C_{18}$-alkyl, $R^{47}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa)

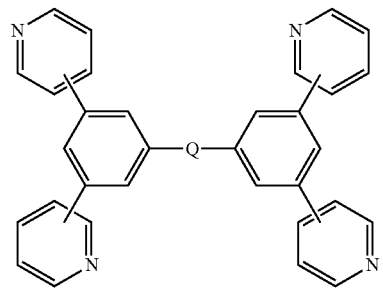
(VIIIa)

in which Q is:

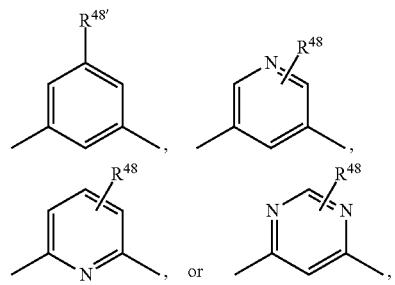

$R^{48}$ is H or $C_1$-$C_{18}$-alkyl and
$R^{48'}$ is H, $C_1$-$C_{18}$-alkyl or

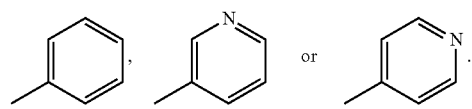

Particular preference is given to a compound of the formula

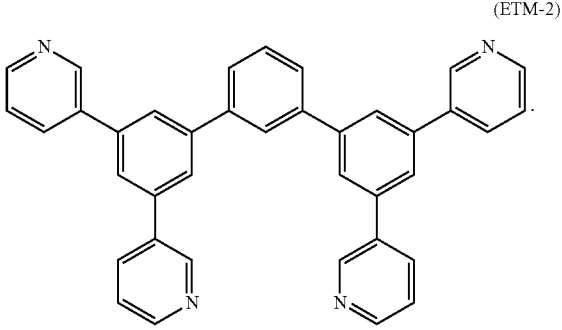 [SMILES: c1cncc(-c2cc(-c3cccnc3)cc(-c3cccc(-c4cc(-c5cccnc5)cc(-c5cccnc5)c4)c3)c2)c1]
(ETM-2)

In a further, very particularly preferred embodiment, the electron-transporting layer comprises a compound Liq and a compound ETM-2.

In a preferred embodiment, the electron-transporting layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008/127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transporting layer. Reference is made to WO2011/157790. Dibenzofuran compounds A-1 to A-36 and B-1 to B-22 described in WO2011/157790 are preferred, wherein dibenzofuran compound

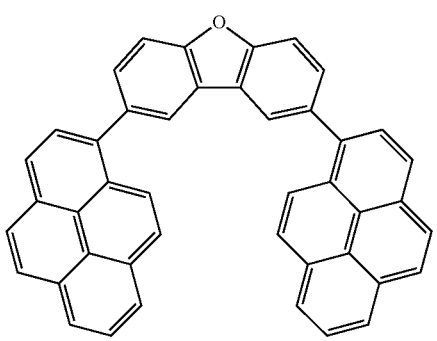

(A-10; = ETM-1)

is most preferred.

In a preferred embodiment, the electron-transporting layer comprises Liq in an amount of 99 to 1% by weight, preferably 75 to 25% by weight, more preferably about 50% by weight, where the amount of Liq and the amount of the dibenzofuran compound(s), especially ETM-1, adds up to a total of 100% by weight.

In a preferred embodiment, the electron-transporting layer comprises at least one phenanthroline derivative and/or pyridine derivative.

In a further preferred embodiment, the electron-transporting layer comprises at least one phenanthroline derivative and/or pyridine derivative and at least one alkali metal hydroxyquinolate complex.

In a further preferred embodiment, the electron-transporting layer comprises at least one of the dibenzofuran compounds A-1 to A-36 and B-1 to B-22 described in WO2011/157790, especially ETM-1.

In a further preferred embodiment, the electron-transporting layer comprises a compound described in WO2012/111462, WO2012/147397, WO2012014621, such as, for example, a compound of formula

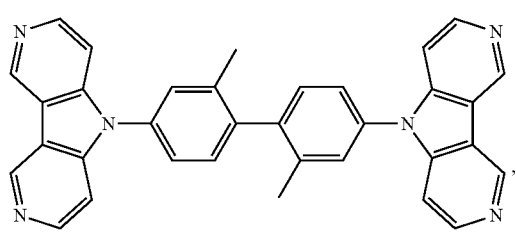

(ETM-3)

US2012/0261654, such as, for example, a compound of formula

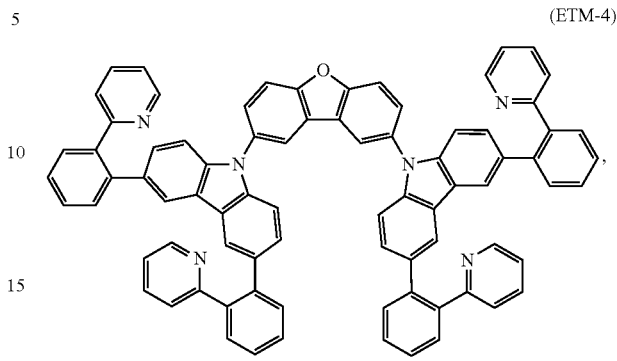

(ETM-4)

and WO2012/115034, such as for example, such as, for example, a compound of formula

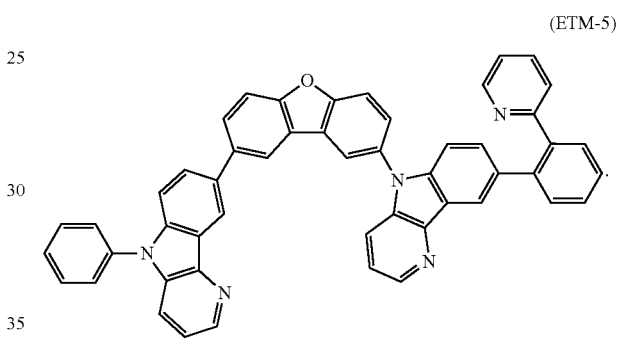

(ETM-5)

Further suitable electron transport materials are mentioned in US 20130181190, especially in table 3, and US 20130119354, especially in table 4.

Electron Injection Layer (h)

The electron injection layer may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (i) as an electron injection layer (h) in order to reduce the operating voltage.

Cathode (i)

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

In general, the different layers, if present, have the following thicknesses:

In general, the different layers in the inventive OLED, if present, have the following thicknesses:

anode (a): 50 to 500 nm, preferably 60 to 200 nm;
hole injection layer (b): 5 to 100 nm, preferably 20 to 80 nm,
hole-transport layer (c): 5 to 120 nm, preferably 10 to 80 nm;

electron/exciton blocking layer (d): 1 to 50 nm, preferably 5 to 10 nm, light-emitting layer (e): 1 to 100 nm, preferably 5 to 60 nm;

hole/exciton blocking layer (f): 1 to 50 nm, preferably 5 to 10 nm, electron-transport layer (g): 5 to 100 nm, preferably 20 to 80 nm;

electron injection layer (h): 1 to 50 nm, preferably 2 to 10 nm;

cathode (i): 20 to 1000 nm, preferably 30 to 500 nm.

The inventive OLED can be produced by methods known to those skilled in the art. In general, the OLED is produced by successive vapor deposition of the individual layers onto a suitable substrate. Suitable substrates are, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

It is possible that the layers of the OLED are all produced by the same coating method. Furthermore, it is likewise possible to conduct two or more different coating methods to produce the layers of the OLED.

The inventive OLEDs can be used in all devices in which electroluminescence is useful. Suitable devices are preferably selected from stationary and mobile visual display units and illumination units. Further suitable devices are devices such as keyboards; items of clothing; furniture; and wallpaper. The present invention therefore also relates to a device selected from the group consisting of stationary visual display units; mobile visual display units; illumination units; keyboards; items of clothing; furniture; and wallpaper comprising an inventive OLED or an inventive light-emitting layer.

Stationary visual display units are, for example, visual display units of computers, televisions, visual display units in printers, kitchen appliances and advertising panels, illuminations and information panels. Mobile visual display units are, for example, visual display units in smartphones, tablet computers, cellphones, laptops, digital cameras, mp-3 players, vehicles, and destination displays on buses and trains.

The inventive Pt- and Pd-carbene complexes can additionally be used in OLEDs with inverse structure. In these inverse OLEDs, the inventive complexes are in turn preferably used in the light-emitting layer. The structure of inverse OLEDs and the materials typically used therein are known to those skilled in the art.

The present invention further provides a white OLED comprising at least one inventive Pt- or Pd-carbene complex. In a preferred embodiment, the inventive Pt- or Pd-carbene complex is used as emitter material in the white OLED. Preferred embodiments of the inventive Pt- and Pd-carbene complexes have been specified above. Suitable structures of white OLEDs and suitable components are known by a person skilled in the art.

In order to obtain white light, the OLED must generate light which colors the entire visible range of the spectrum. However, organic emitters normally emit only in a limited portion of the visible spectrum i.e. are colored. White light can be generated by the combination of different emitters. Typically, red, green and blue emitters are combined. However, the prior art also discloses other methods for formation of white OLEDs, for example the triplet harvesting approach. Suitable structures for white OLEDs or methods for formation of white OLEDs are known to those skilled in the art.

In one embodiment of a white OLED, several dyes are layered one on top of another in the light-emitting layer of an OLED and hence combined (layered device). This can be achieved by mixing all dyes or by direct series connection of different-colored layers. The expression "layered OLED" and suitable embodiments are known to those skilled in the art.

In a further embodiment of a white OLED, several different-colored OLEDs are stacked one on top of another (stacked device). For the stacking of two OLEDs, what is called a charge generation layer (CG layer) is used. This CG layer may be formed, for example, from one electrically n-doped and one electrically p-doped transport layer. The expression "stacked OLED" and suitable embodiments are known to those skilled in the art.

In further embodiments of this "stacked device concept", it is also possible to stack only two OLEDs or to stack more than three OLEDs.

In a further embodiment of white OLEDs, the two concepts mentioned for white light generation can also be combined. For example, a single-color OLED (for example blue) can be stacked with a multicolor layered OLED (for example red-green). Further combinations of the two concepts are conceivable and known to those skilled in the art.

The inventive Pt- or Pd-carbene complex can be used in any of the layers mentioned above in white OLEDs. In a preferred embodiment, it is used in one or more or all light-emitting layer(s) of the OLED(s), in which case the structure of the invention metal carbene complex is varied as a function of the use of the complex. Suitable and preferred components for the further layers of the light OLED(s) or materials suitable as matrix material in the light-emitting layer(s) and preferred matrix materials are likewise specified above.

The examples which follow, more particularly the methods, materials, conditions, process parameters, apparatus and the like detailed in the examples, are intended to support the present invention, but not to restrict the scope of the present invention.

In a further embodiment, the present invention relates to the use of the complex of formula (I) or (II) according to the present invention as emitter material. Preferred complexes of formula (I) or (II) according to the present invention are mentioned above.

EXAMPLES

All experiments are carried out in protective gas atmosphere. The percentages and ratios mentioned in the examples below—unless stated otherwise—are % by weight and weight ratios.

I. Synthesis Examples

I Carbene Precursor Synthesis

The synthesis of suitable carbene ligand precursors is well documented in literature. Procedures can be found e.g. in Enders et al. (Helvetica Chimica Acta 1996, 79, 61-83), Bielawski et al. (Inorg. Chem. 2009, 48, 6924-6933), U.S. provisional application 61/496,646, and WO2005019373.

II Complex Synthesis

II.1 Synthesis of Complex (Iaa)

A mixture of 1-(dibenzo[b,d]-3-methyl-1H-imidazolium iodide (301 mg, 0.8 mmol) and silver(I) oxide (94 mg, 0.4 mmol) in dry DMF (20 mL) is stirred under argon in the dark at 50° C. for 3 h. Dichloro(1,5-cyclooctadiene)platinum(II) (299 mg, 0.8 mmol) is added at RT and the mixture is stirred at RT for 17 h and then at 130° C. for another 24 h. After cooling to RT, N,N-diphenylformamidine (661 mg, 3.2 mmol) and potassium tert-butanolate (360 mg, 3.2 mmol) are added, and the resulting mixture is stirred at RT for 48 h and another 6 h at 100° C. The vola-tiles are removed under reduced pressure. The residue is taken up in water, and the solid is filtered off and purified by column chromatography (ethyl acetate/isohexane 5:2) The isolated product is washed with isohexane and dried under vacuum. Yield: 112 mg (0.09 mmol, 22%). $^1$H-NMR (CDCl$_3$, 300 MHz): δ=8.50 (s, 2H), 7.89 (d, 2H), 7.58 (dd, 6H), 7.54-7.29 (m, 14H), 7.29-7.22 (m, 4H), 7.08-6.99 (m, 6H), 6.87-6.79 (m, 2H), 5.86 (d, 2H), 2.30 (s, 6H) ppm. $^{13}$C-NMR (CDCl$_3$, 75 MHz): δ=160.6, 156.9, 155.5, 152.9, 151.6, 142.7, 132.2, 130.4, 130.0, 128.6, 128.1, 126.0, 124.9, 124.1, 123.1, 122.8, 122.1, 121.1, 120.1, 119.6, 116.8, 115.7, 111.4, 35.3 ppm. M.p.=251-252° C.

Photoluminescence (2% in PMMA matrix): $\lambda_{max}$=561 nm, CIE: (0.44; 0.55); QY=82%, $\tau_0$=1.8 ρs. Neat film: $\lambda_{max}$=589 nm, CIE: (0.55; 0.47).

In FIG. 1a, the crystal structure of complex (Iaa) ist shown.

II.2 Synthesis of Complex (Iab)

A mixture of 1,3-diphenyl-1H-benzimidazolium tetrafluoroborate (573 mg, 1.6 mmol) and silver(I) oxide (185 mg, 0.8 mmol) in dry DMF (40 mL) is stirred under argon in the dark at 60° C. for 20 h. Dichloro(1,5-cyclooctadiene)platinum(II) (599 mg, 1.6 mmol) is added at RT and the mixture is stirred at RT for 48 h and then at 130° C. for another 24 h. After cooling to RT, N,N-diphenylformami-dine (1.26 g, 6.4 mmol) and potassium tert-butanolate (718 mg, 6.4 mmol) are added, and the resulting mixture is stirred at RT for 48 h and another 20 h at 100° C. The vola-tiles are removed under reduced pressure. The residue is taken up in water, and the solid is filtered off and purified by column chromatography (dichloromethane/isohexane 1:1) The isolated product is dried under vacuum. Yield: 299 mg (0.2 mmol, 28%). $^1$H-NMR (DMSO-d$_6$, 600 MHz): δ=7.90 (d, 2H), 7.67 (t, 2H), 7.62 (d, 2H), 7.54 (d, 4H), 7.49 (s, 2H), 7.45 (d, 2H), 7.35-7.25 (m, 6H), 7.22 (t, 2H), 7.13 (d, 4H), 7.09 (t, 4H), 6.95 (t, 4H), 6.87-6.76 (m, 6H), 6.73 (t, 2H), 6.66 (d, 2H), 6.22 (t, 2H), 5.63 (t, 2H) ppm. $^{13}$C-NMR (DMSO-d$_6$, 151 MHz): δ=157, 134.8, 130.1, 129.1, 128.8, 128.4, 127.7, 127.4, 126.6, 124.0, 123.2, 122.9, 122.4, 121.9, 121.8, 121.5, 121.4, 121.14, 121.10, 111.4, 111.3, 110.9 ppm.

Photoluminescence (2% in PMMA matrix): $\lambda_{max}$=596 nm, CIE: (0.56; 0.43); QY=82%, $\tau_0$=2.1 ρs. Neat film: $\lambda_{max}$=618 nm, CIE: (0.60; 0.38).

Figure 1B:
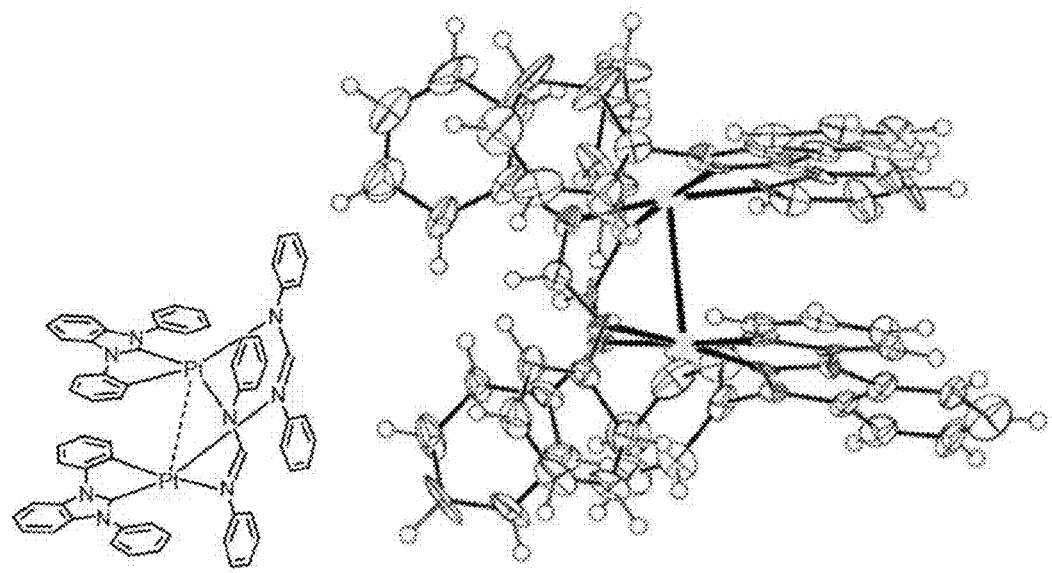

In FIG. 1b, the crystal structure of complex (Iab) ist shown.

III Application Examples

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer AJ20-1000 from Plexcore is spun on from solution.

Thereafter, a mixture of complex (emitter) Iaa (10% by wt.) and compound

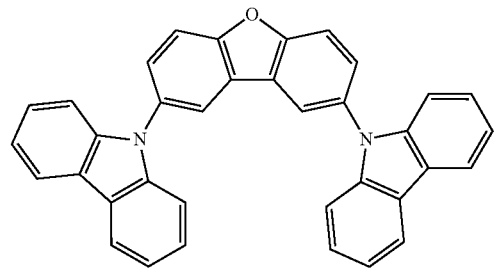

(Host-1)

or compound

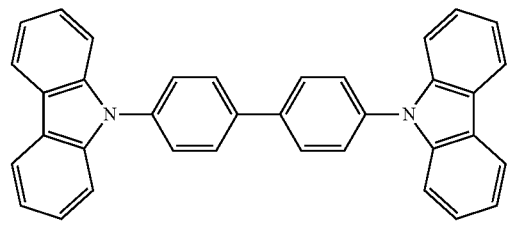

(CBP, Host-2)

(90% by wt.) is applied by spin coating with a thickness of 40 nm, the latter compounds functioning as matrix materials.

Subsequently, the optional HBL (hole blocking layer) (5 nm layer thickness) and the ETL (electron transport layer) are applied by vapor deposition. As an electron incjetion layer, KF is applied by vapor deposition with a thickness of 4 nm and finally a 100 nm-thick Al electrode. All components are adhesive-bonded to a glass lid in an inert nitrogen atmosphere.

| Example | Host | HBL | ETL | $\gamma_{max}$ | CIE(x;y) |
|---|---|---|---|---|---|
| Device 1 | Host-2 | | BPhen (40 nm) | 568 nm | 0.46;0.53 |
| Device 2 | Host-1 | Host-1 | ETM-1: Liq (1:1, 35 nm) | 566 nm | 0.45;0.54 |

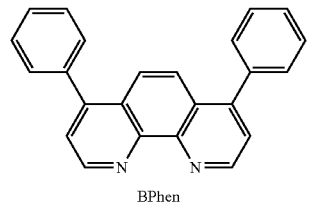 [SMILES: c1ccc(-c2ccnc3c2ccc2c(-c4ccccc4)ccnc23)cc1]

BPhen

Figure 2:
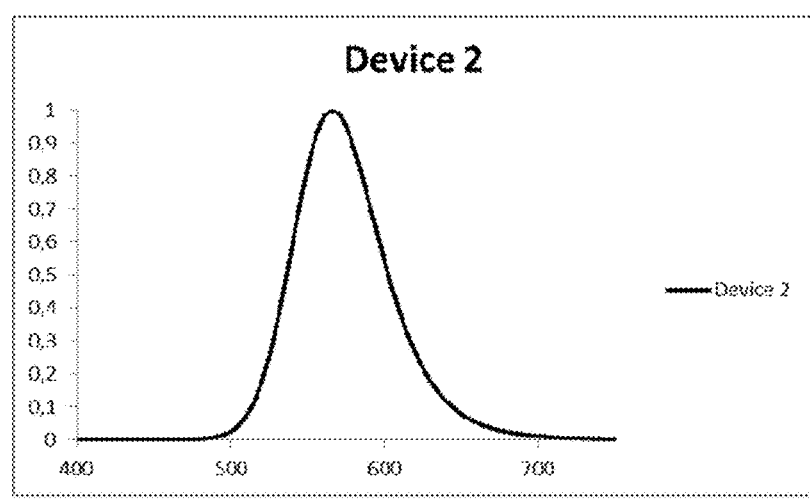

In FIG. 2, the EL (electroluminescence) spectrum of device 2 is shown (y-axis: intensity in arbitrary units; x-axis: wavelength in nm).

The invention claimed is:

1. A complex of the general formula (I) or (II)

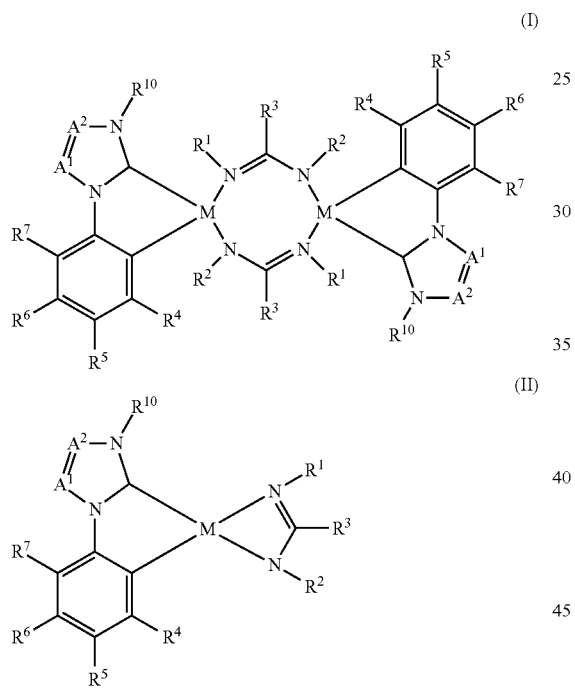

wherein M, $A^1$, $A^2$, $R^1$, $R^2$, $R^3$, $R^4$, $R^5$, $R^6$, $R^7$ and $R^{10}$ are each defined as follows:

M is Pt or Pd, $A^1$ is N or $CR^8$, $A^2$ is N or $CR^9$, $R^1$ and $R^2$ are independently of each other a $C_1$-$C_{18}$alkyl group, which can optionally be substituted by at least one substituent E; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a $C_1$-$C_{18}$haloalkyl group; or CN;

$R^3$ is hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —O—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom; a $C_1$-$C_{18}$haloalkyl group; or CN;

or $R^1$ and $R^3$ or $R^2$ and $R^3$ together form a group of formula

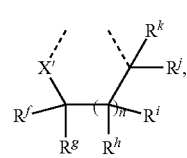

wherein X' is present in the position of $R^3$ and is selected from O, S, $NR^{75}$ and $CR^{73}R^{74}$;

$R^f$, $R^g$, $R^h$, $R^i$, $R^j$ and $R^k$ are independently of each other H, a $C_1$-$C_5$alkyl group, a fluoro$C_1$-$C_4$alkyl group, or a $C_3$-$C_6$cycloalkyl group;

n is 0 or 1;

wherein the group of formula (III) comprises 0, 1 or 2 double bonds; in the case that 1 or 2 double bonds are present in the group of formula (III), the carbon atoms connected with the double bonds are each substituted by only one residue $R^f$, $R^j$ and/or—in the case that n is 1—$R^h$;

$R^5$ and $R^6$ are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —$NR^{65}$—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom; a $C_1$-$C_{18}$haloalkyl group; CN; or $SiR^{80}R^{81}R^{82}$;

or $R^5$ and $R^6$ together form a group of formula

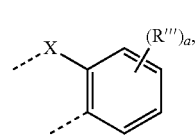

wherein X is O, S, NR$^{75}$ or CR$^{73}$R$^{74}$; R''' is C$_1$-C$_8$alkyl and a is 0, 1 or 2;

R$^4$ and R$^7$
are independently of each other hydrogen; a C$_1$-C$_{18}$alkyl group, which can optionally be substituted by at least one substituent E and/or interrupted by D; a C$_3$-C$_{12}$cycloalkyl group, which can optionally be substituted by at least one substituent E; a heterocycloalkyl group comprising 3 to 6 ring atoms, interrupted by at least one of O, S and NR$^{65}$ and/or substituted by at least one substituent E; a C$_6$-C$_{14}$aryl group, which can optionally be substituted by at least one substituent G; a heteroaryl group comprising 5 to 11 ring atoms, which can optionally be substituted by at least one substituent G, interrupted by at least one of O, S, N and NR$^{65}$ a halogen atom; a C$_1$-C$_{18}$haloalkyl group; CN; or SiR$^{80}$R$^{81}$R$^{82}$;

or

R$^6$ and R$^7$ together form a group of formula

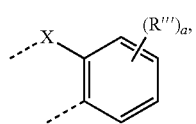

(IV)

wherein X is O, S, NR$^{75}$ or CR$^{73}$R$^{74}$; R''' is C$_1$-C$_8$alkyl and a is 0, 1 or 2;

R$^8$ and R$^9$
are independently of each other hydrogen; a C$_1$-C$_{18}$alkyl group, which can optionally be substituted by at least one substituent E and/or interrupted by D; a C$_3$-C$_{12}$cycloalkyl group, which can optionally be substituted by at least one substituent E; a heterocycloalkyl group comprising 3 to 6 ring atoms, interrupted by at least one of O, S and NR$^{65}$ and/or substituted by at least one substituent E; a C$_6$-C$_{14}$aryl group, which can optionally be substituted by at least one substituent G; a —O—C$_6$-C$_{14}$aryl group, which can optionally be substituted by at least one substituent G; a heteroaryl group comprising 5 to 11 ring atoms, which can optionally be substituted by at least one substituent G, interrupted by at least one of O, S, N and NR$^{65}$; a halogen atom; a C$_1$-C$_{18}$haloalkyl group; or CN;

or

R$^8$ and R$^9$ together form a group of formula

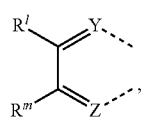

(V)

wherein Y is N or CR$^n$; Z is N or CR$^o$;

R$^l$, R$^m$, R$^n$ and R$^o$ are independently of each other H, a C$_1$-C$_5$alkyl group, a fluoroC$_1$-C$_4$alkyl group, or a C$_3$-C$_6$cycloalkyl group;

R$^{10}$
is a C$_1$-C$_{18}$alkyl group, which can optionally be substituted by at least one substituent E; a C$_3$-C$_{12}$cycloalkyl group, which can optionally be substituted by at least one substituent E; a heterocycloalkyl group comprising 3 to 6 ring atoms, interrupted by at least one of O, S and NR$^{65}$ and/or substituted by at least one substituent E; a C$_6$-C$_{14}$aryl group, which can optionally be substituted by at least one substituent G; a heteroaryl group comprising 5 to 11 ring atoms, which can optionally be substituted by at least one substituent G, interrupted by at least one of O, S, N and NR$^{65}$;

D is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C;

E is —OR$^{69}$, —SR$^{69}$, —NR$^{65}$R$^{66}$, —COR$^{68}$, —COOR$^{67}$, —CONR$^{65}$R$^{66}$, —CN, halogen, or a C$_1$-C$_{18}$alkyl group, which can optionally be substituted by at least one substituent E and/or interrupted by D;

G is E; or an unsubstituted C$_6$-C$_{14}$aryl group; a C$_6$-C$_{14}$aryl group, which is substituted by F, C$_1$-C$_{18}$alkyl, or C$_1$-C$_{18}$alkyl, which is substituted by F and/or interrupted by O; an unsubstituted heteroaryl group comprising 5 to 11 ring atoms, interrupted by at least one of O, S, N and NR$^{65}$; or a heteroaryl group comprising 5 to 11 ring atoms, interrupted by at least one of O, S, N and NR$^{65}$, which is substituted by F, unsubstituted C$_1$-C$_{18}$alkyl, SiR$^{80}$R$^{81}$R$^{82}$, or C$_1$-C$_{18}$alkyl which is substituted by F and/or interrupted by O;

R$^{63}$ and R$^{64}$ are independently of each other H; unsubstituted C$_6$-C$_{18}$aryl; C$_6$-C$_{18}$aryl which is substituted by C$_1$-C$_{18}$alkyl, or C$_1$-C$_{18}$alkoxy; unsubstituted C$_1$-C$_{18}$alkyl; or C$_1$-C$_{18}$alkyl which is interrupted by —O—;

R$^{65}$ and R$^{66}$ are independently of each other H, an unsubstituted C$_6$-C$_{18}$aryl group; a C$_6$-C$_{18}$aryl group which is substituted by C$_1$-C$_{18}$alkyl, or C$_1$-C$_{18}$alkoxy; an unsubstituted C$_1$-C$_{18}$alkyl group; or a C$_1$-C$_{18}$alkyl group, which is interrupted by —O—; or R$^{65}$ and R$^{66}$ together form a five or six membered ring;

R$^{67}$ is H, an unsubstituted C$_6$-C$_{18}$aryl group; a C$_6$-C$_{18}$aryl group, which is substituted by C$_1$-C$_{18}$alkyl, or C$_1$-C$_{18}$alkoxy; an unsubstituted C$_1$-C$_{18}$alkyl group; or a C$_1$-C$_{18}$alkyl group, which is interrupted by —O—;

R$^{68}$ is H; an unsubstituted C$_6$-C$_{18}$aryl group; a C$_6$-C$_{18}$aryl group, which is substituted by C$_1$-C$_{18}$alkyl, or C$_1$-C$_{18}$alkoxy; an unsubstituted C$_1$-C$_{18}$alkyl group; or a C$_1$-C$_{18}$alkyl group, which is interrupted by —O—;

R$^{69}$ is H, an unsubstituted C$_6$-C$_{18}$aryl; a C$_6$-C$_{18}$aryl, which is substituted by C$_1$-C$_{18}$alkyl, or C$_1$-C$_{18}$alkoxy; an unsubstituted C$_1$-C$_{18}$alkyl group; or a C$_1$-C$_{18}$alkyl group, which is interrupted by —O—;

R$^{70}$ and R$^{71}$ are independently of each other an unsubstituted C$_1$-C$_{18}$alkyl group; an unsubstituted C$_6$-C$_{18}$aryl group; or a C$_6$-C$_{18}$aryl group, which is substituted by C$_1$-C$_{18}$alkyl;

R$^{72}$ is an unsubstituted C$_1$-C$_{18}$alkyl group; an unsubstituted C$_6$-C$_{18}$aryl group, or a C$_6$-C$_{18}$aryl group, which is substituted by C$_1$-C$_{18}$alkyl;

R$^{73}$ and R$^{74}$ are independently of each other H; unsubstituted C$_6$-C$_{18}$aryl; C$_6$-C$_{18}$aryl which is substituted by C$_1$-C$_{18}$alkyl, or C$_1$-C$_{18}$alkoxy; unsubstituted C$_1$-C$_{18}$alkyl; or C$_1$-C$_{18}$alkyl which is interrupted by —O;

R$^{75}$ is a C$_6$-C$_{18}$aryl group; a C$_6$-C$_{18}$aryl which is substituted by C$_1$-C$_{18}$alkyl, or C$_1$-C$_{18}$alkoxy; a C$_1$-C$_{18}$alkyl group; or a C$_1$-C$_{18}$alkyl group, which is interrupted by —O—;

R$^{80}$, R$^{81}$ and R$^{82}$ are independently of each other a C$_1$-C$_{25}$alkyl group, which can optionally be interrupted by O; a C$_6$-C$_{14}$aryl group, which can optionally be substituted by C$_1$-C$_{18}$alkyl; or a heteroaryl group comprising 5 to 11 ring atoms, which can optionally be substituted by $C_1$-$C_{18}$alkyl.

2. The complex according to claim 1, wherein M, $A^1$ and $A^2$, are each defined as follows:
M is Pt;
$A^1$ is $CR^8$;
$A^2$ is $CR^9$.

3. The complex according to claim 1, wherein:
$R^8$ and $R^9$
are independently of each other hydrogen; a $C_1$-$C_{12}$alkyl group, which can optionally be substituted by E and/or interrupted by D; or a phenyl group, which can optionally be substituted by at least one substituent G; or
$R^8$ and $R^9$ together form a group of formula

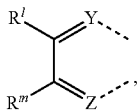
(V)

wherein Y is N or $CR^n$; Z is N or $CR^o$;
$R^l$, $R^m$, $R^n$ and $R^o$ are independently of each other H, a $C_1$-$C_5$alkyl group, $C_3$-$C_6$cycloalkyl group.

4. The complex according to claim 1, wherein:
$R^1$ and $R^2$
are independently of each other a $C_1$-$C_{12}$alkyl group, which can optionally be substituted by at least one substituent E; a $C_3$-$C_6$cycloalkyl group, which can optionally be substituted by at least one substituent E; a $C_6$-$C_{14}$aryl group, which can optionally be substituted by one or two substituents G; a heteroaryl group comprising 5 to 11 ring atoms, which can optionally be substituted by one or two substituents G, interrupted by at least one of O, S, N and $NR^{65}$; a $C_1$-$C_{18}$haloalkyl group; or CN;
$R^3$
is hydrogen; a $C_1$-$C_{12}$alkyl group, which can optionally be substituted by at least one substituent E and/or interrupted by D; a $C_3$-$C_6$cycloalkyl group, which can optionally be substituted by at least one substituent E; a $C_6$-$C_{14}$aryl group, which can optionally be substituted by one or two substituents G; a —O—$C_6$-$C_{14}$aryl group, which can optionally be substituted by one or two substituents G; a heteroaryl group comprising 5 to 11 ring atoms, which can optionally be substituted by one or two substituents G, interrupted by at least one of O, S, N and $NR^{65}$; a halogen atom; a $C_1$-$C_{18}$haloalkyl group; or CN;
or
$R^1$ and $R^3$ or $R^2$ and $R^3$ together form a group of formula

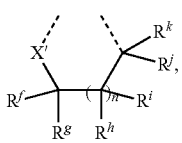
(III)

wherein X' is present in the position of $R^3$ and is selected from O and S;
n is 0 or 1;

$R^f$, $R^g$, $R^h$, $R^i$, $R^j$ and $R^k$ are independently of each other H, a $C_1$-$C_5$alkyl group, $C_3$-$C_6$cycloalkyl group;
wherein the group of formula (III) comprises 0 or 1 double bonds.

5. The complex according to claim 1, wherein $R^5$ and $R^6$
are independently of each other hydrogen; a $C_1$-$C_{12}$alkyl group, which can optionally be substituted by E and/or interrupted by D; a $C_3$-$C_{12}$cycloalkyl group, which can optionally be substituted by E; a $C_6$-$C_{10}$aryl group, which can optionally be substituted by at least one substituent G; or
$R^5$ and $R^6$ together form a group of formula

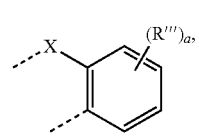
(IV)

wherein X is O or S; R''' is $C_1$-$C_8$alkyl and a is 0, 1 or 2;
$R^4$ and $R^7$
are independently of each other hydrogen; or a $C_1$-$C_{12}$alkyl group, which can optionally be substituted by E and/or interrupted by D, preferably a $CH_2$—$C_1$-$C_7$alkyl group, which can optionally be substituted by E and/or interrupted by D;
or
$R^6$ and $R^7$ together form a group of formula

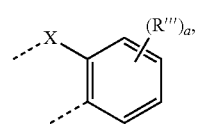
(IV)

wherein X is O or S; R''' is $C_1$-$C_8$alkyl and a is 0, 1 or 2.

6. The complex according to claim 1, wherein
$R^{10}$
is a $C_1$-$C_{12}$alkyl group, which can optionally be substituted by E; a $C_3$-$C_{12}$cycloalkyl group, which can optionally be substituted by E;
or
a group of formula

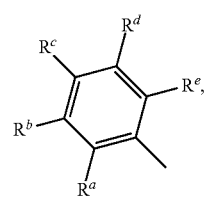
(VI)

wherein $R^a$ and $R^e$ are independently of each other hydrogen H, a $C_1$-$C_5$alkyl group, a fluoro$C_1$-$C_4$alkyl group, or a $C_3$-$C_6$cycloalkyl group;
$R^c$, $R^b$ and $R^d$ are independently of each other hydrogen; a $C_1$-$C_{18}$alkyl group, which can optionally be substituted by E and/or interrupted by D; a $C_3$-$C_{12}$cycloalkyl group, which can optionally be substituted by G; a $C_6$-$C_{14}$aryl group, which can optionally be substituted by G; or a heteroaryl group comprising 3 to 30 ring atoms, which can optionally be substituted by G; $C_1$-$C_8$haloalkyl; or $SiR^{80}R^{81}R^{82}$;

or $R^c$ and $R^b$, or $R^a$ and $R^b$ together form a group of formula

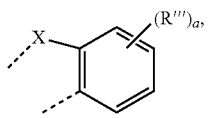

(IV)

wherein X is O, S, $NR^{75}$ or $CR^{73}R^{74}$; R''' is $C_1$-$C_8$alkyl and a is 0, 1 or 2.

7. The complex according to claim 1, wherein

D is —O—, —S— or —$NR^{65}$—;

E is $C_1$-$C_8$alkyl, $C_1$-$C_8$alkoxy, CN, halogen, or $C_1$-$C_8$haloalkyl;

G is a $C_1$-$C_5$alkyl group, or a group of formula

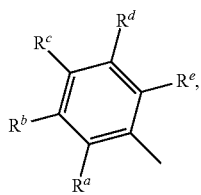

(VI)

$R^a$ and $R^e$ are independently of each other H, a $C_1$-$C_5$alkyl group, a fluoro$C_1$-$C_4$alkyl group, or a $C_3$-$C_6$cycloalkyl group;

$R^c$, $R^b$ and $R^d$ are independently of each other hydrogen; a $C_1$-$C_{18}$alkyl group, which can optionally be substituted by E and/or interrupted by D; a $C_3$-$C_{12}$cycloalkyl group, which can optionally be substituted by G; a heterocycloalkyl radical comprising 3 to 10 ring atoms which is interrupted by at least one of O, S and $NR^{65}$ and/or substituted by E; a $C_6$-$C_{24}$aryl group, which can optionally be substituted by G; or a heteroaryl group comprising 3 to 30 ring atoms, which is interrupted by at least one of O, S and $NR^{65}$ and which can optionally be substituted by G; a halogen atom; $C_1$-$C_8$haloalkyl; CN; or $SiR^{80}R^{81}R^{82}$;

or $R^c$ and $R^b$, or $R^a$ and $R^b$ together form a group of formula

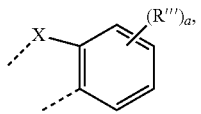

(IV)

wherein X is O, S, $NR^{75}$ or $CR^{73}R^{74}$; R''' is $C_1$-$C_8$alkyl and a is 0, 1 or 2;

$R^{65}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{69}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{73}$ and $R^{74}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{75}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{80}$, $R^{81}$ and $R^{82}$ are independently of each other a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

8. The complex according to claim 1, selected from structures (Ia) and (IIa):

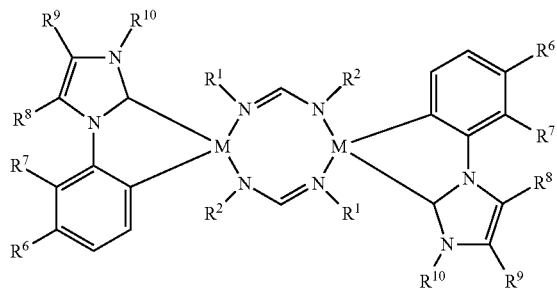

(Ia)

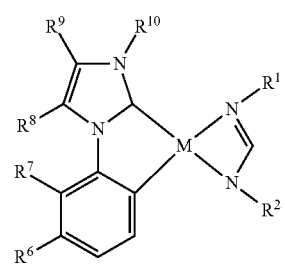

(IIa)

wherein

M is Pt or Pd, $R^1$ and $R^2$ are independently of each other a $C_1$-$C_5$alkyl group; a phenyl group, which can optionally be substituted by one or two substituents G; a heteroaryl group comprising 5 to 6 ring atoms, which can optionally be substituted by one or two substituents G, interrupted by at least one of O, S, N and $NR^{65}$; or CN;

$R^6$ is hydrogen; a $C_1$-$C_5$alkyl group, which can optionally be substituted by at least one substituent E; a $C_3$-$C_6$cycloalkyl group, which can optionally be substituted by at least one substituent E; or either $R^5$ or $R^6$ is a phenyl group, which can optionally be substituted by one or two groups G;

$R^7$ is hydrogen; or a $C_1$-$C_5$alkyl group, which can optionally be substituted by E and/or interrupted by D, or $R^6$ and $R^7$ together form a group of formula

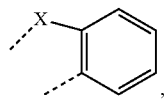
(IV')

wherein X is O or S;

$R^8$ and $R^9$ are hydrogen; methyl; ethyl; an unsubstituted phenyl group; or a phenyl group, which is substituted by one or two $C_1$-$C_8$alkyl groups; or $R^8$ and $R^9$ together form a group of formula

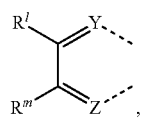
(V)

wherein Y is N or $CR^n$; Z is N or $CR^o$;

$R^l$, $R^m$, $R^n$ and $R^o$ are independently of each other H, or a $C_1$-$C_5$alkyl group;

$R^{10}$ is a $C_1$-$C_5$alkyl group, which can optionally be substituted by E; a $C_3$-$C_6$cycloalkyl group, which can optionally be substituted by E;

or a group of formula R

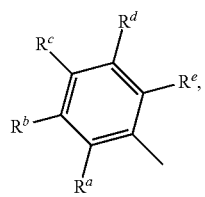

wherein $R^a$ and $R^e$ are independently of each other H, a $C_1$-$C_5$alkyl group, $C_3$-$C_6$cycloalkyl group;

$R^c$, $R^b$ and $R^d$ are independently of each other H, a $C_1$-$C_5$alkyl group, $C_3$-$C_6$cycloalkyl group;

or $R^c$ and $R^b$, or $R^a$ and $R^b$ together form a group of formula

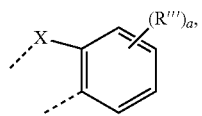

wherein X is O or S; $R'''$ is $C_1$-$C_8$alkyl and a is 0, 1 or 2;

D is —S— or —O—;

E is —$OR^{69}$, $CF_3$, $C_1$-$C_8$alkyl or F;

G is —$OR^{69}$, $CF_3$ or $C_1$-$C_8$alkyl;

$R^{65}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—;

$R^{69}$ is a phenyl group, which can optionally be substituted by one or two $C_1$-$C_8$alkyl groups; an unsubstituted $C_1$-$C_{18}$alkyl group; or a $C_1$-$C_{18}$alkyl group, which is interrupted by —O—.

9. The complex according to claim 8, selected from the following structures:

(Iaa), (Iab), (Iac), (Iad), (Iae), (Iaf), (Iag), (Iah), (Iai), (Iaj), (IIaa), (IIab), (IIac), (IIad), (IIae), (IIaf), (IIag), (IIah), (IIai) and (IIaj); wherein M is Pt or Pd:

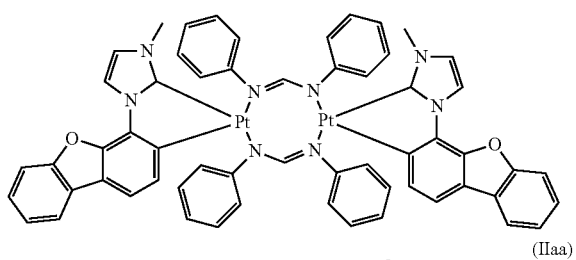
(Iaa)

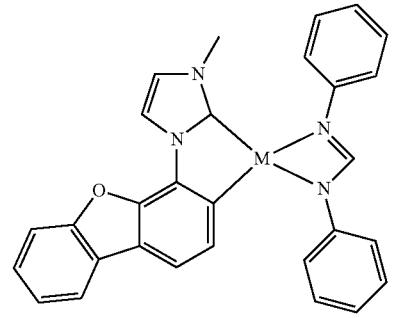
(Iab)

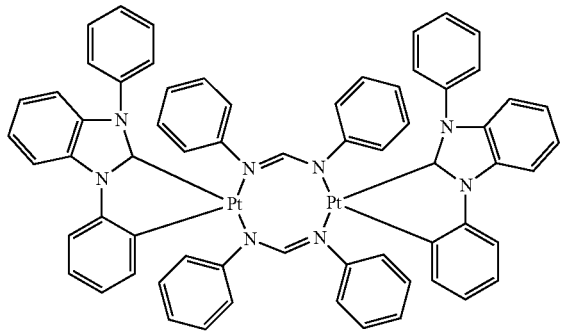
(IIaa)

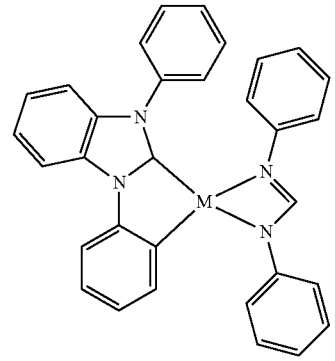
(IIab)

(Iac)
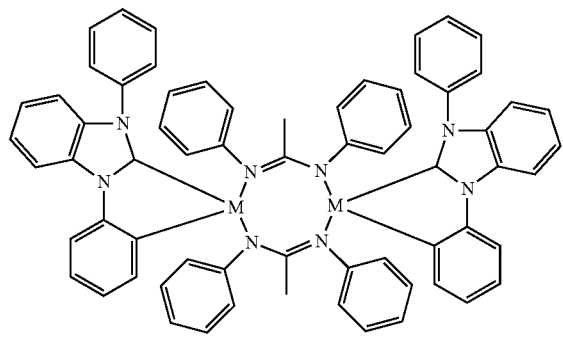
(Iae)
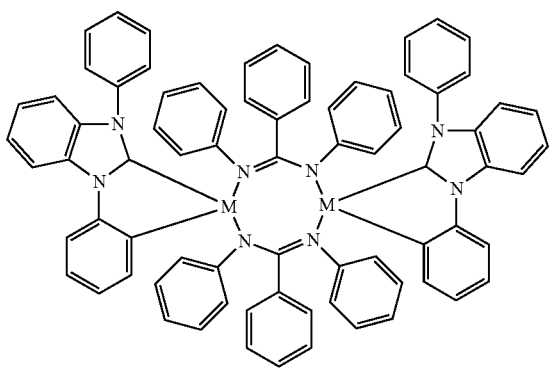
(IIac)
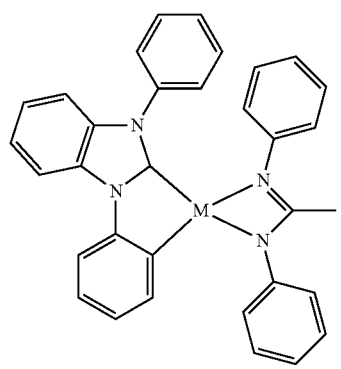
(IIae)
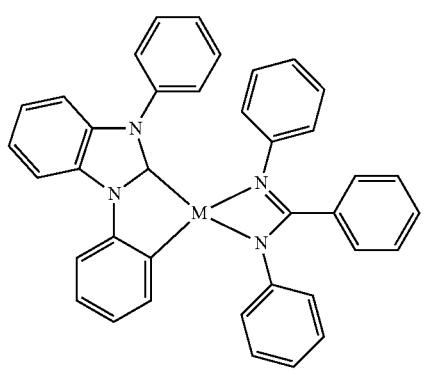
(Iad)
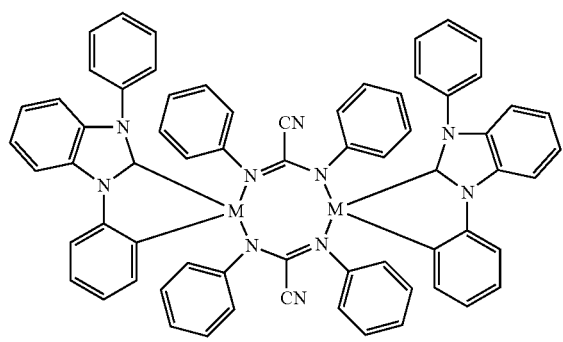
(Iaf)
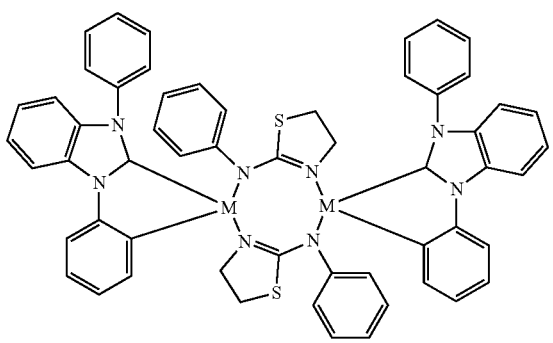
(IIad)
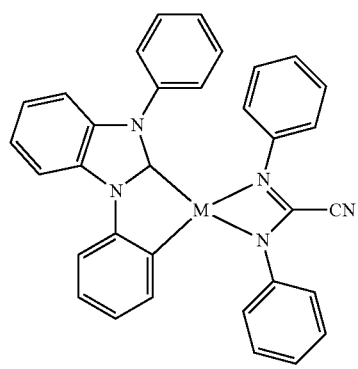
(IIaf)
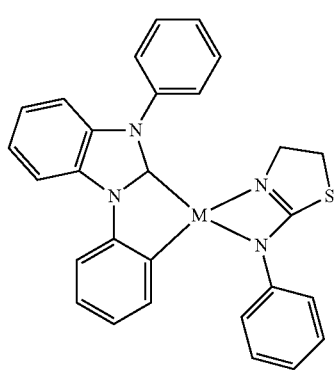

(Iag)
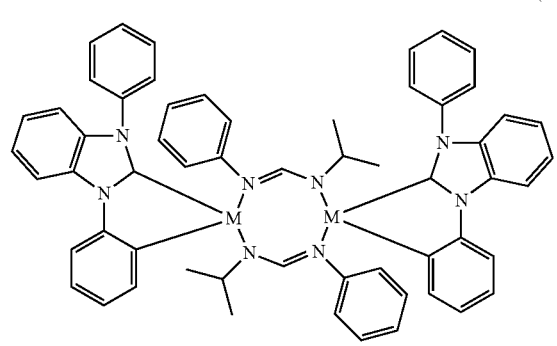
(IIag)
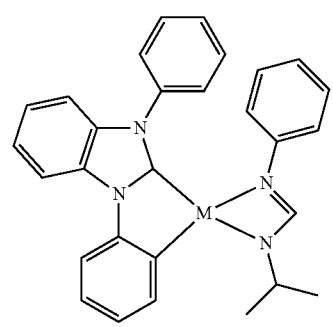
(Iah)
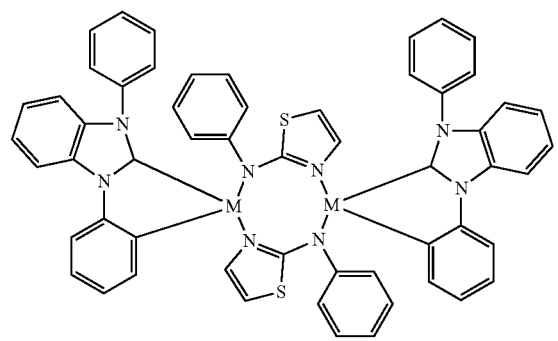
(IIah)
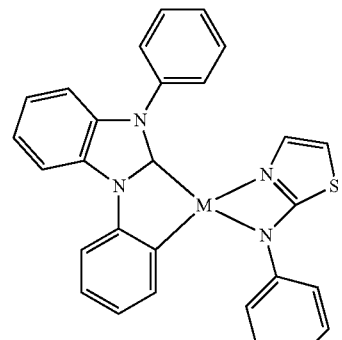
(Iai)
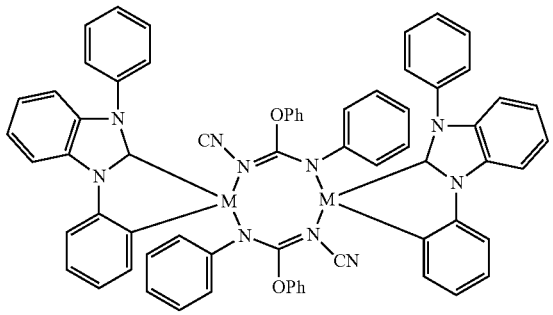
(IIai)
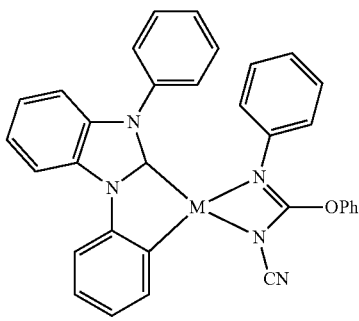
(Iaj)
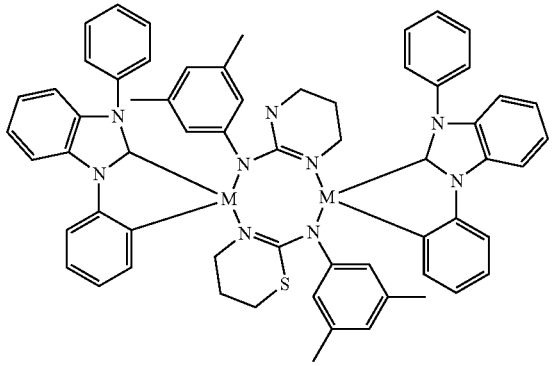
(IIaj)
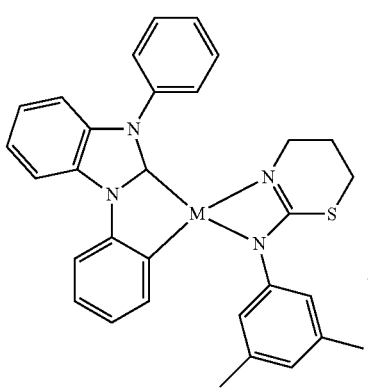
10. A process for preparing a complex according to claim 1, comprising the steps (i) contacting an imidazolium salt of formula (IV)

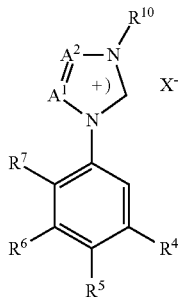

(IV)

wherein $A^1$ is N or $CR^8$,
$A^2$ is N or $CR^9$,
$R^5$ and $R^6$
are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —$NR^{65}$—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom; a $C_1$-$C_{18}$haloalkyl group; CN; or $SiR^{80}R^{81}R^{82}$;
or $R^5$ and $R^6$ together form a group of formula

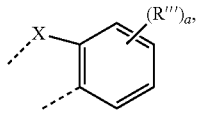

(IV)

wherein X is O, S, $NR^{75}$ or $CR^{73}R^{74}$; R''' is $C_1$-$C_8$alkyl and a is 0, 1 or 2;

$R^4$ and $R^7$ are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$ a halogen atom; a $C_1$-$C_{18}$haloalkyl group; CN; or $SiR^{80}R^{81}R^{82}$;
or $R^6$ and $R^7$ together form a group of formula

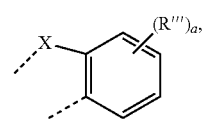

(IV)

wherein X is O, S, $NR^{75}$ or $CR^{73}R^{74}$; R''' is $C_1$-$C_8$alkyl and a is 0, 1 or 2;

$R^8$ and $R^9$ are independently of each other hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —O—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom; a $C_1$-$C_{18}$haloalkyl group; or CN;
or $R^8$ and $R^9$ together form a group of formula

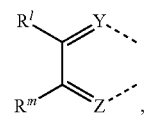

(V)

wherein Y is N or $CR^n$; Z is N or $CR^o$;

$R^l$, $R^m$, $R^n$ and $R^o$ are independently of each other H, a $C_1$-$C_5$alkyl group, a fluoro$C_1$-$C_4$alkyl group, or a $C_3$-$C_6$cycloalkyl group;

$R^{10}$
is a $C_1$-$C_{18}$alkyl group, which can optionally be substituted by at least one substituent E; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$;

D is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—;

E is —$OR^{69}$, —$SR^{69}$, —$NR^{65}R^{66}$, —$COR^{68}$, —$COOR^{67}$, —$CONR^{65}R^{66}$, —CN, halogen, or a $C_1$-$C_{18}$alkyl group, which can optionally be substituted by at least one substituent E and/or interrupted by D;

G is E; or an unsubstituted $C_6$-$C_{14}$aryl group; a $C_6$-$C_{14}$aryl group, which is substituted by F, $C_1$-$C_{18}$alkyl, or $C_1$-$C_{18}$alkyl, which is substituted by F and/or interrupted by O; an unsubstituted heteroaryl group comprising 5 to 11 ring atoms, interrupted by at least one of O, S, N and $NR^{65}$; or a heteroaryl group comprising 5 to 11 ring atoms, interrupted by at least one of O, S, N and $NR^{65}$, which is substituted by F, unsubstituted $C_1$-$C_{18}$alkyl, $SiR^{80}R^{81}R^{82}$, or $C_1$-$C_{18}$alkyl which is substituted by F and/or interrupted by O;

$R^{63}$ and $R^{64}$ are independently of each other H; unsubstituted $C_6$-$C_{18}$aryl; $C_6$-$C_{18}$aryl which is substituted by $C_1$-$C_{18}$alkyl, or $C_1$-$C_{18}$alkoxy; unsubstituted $C_1$-$C_{18}$alkyl; or $C_1$-$C_{18}$alkyl which is interrupted by —O—;

$R^{65}$ and $R^{66}$ are independently of each other H, an unsubstituted $C_6$-$C_{18}$aryl group; a $C_6$-$C_{18}$aryl group which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—; or $R^{65}$ and $R^{66}$ together form a five or six membered ring;

$R^{67}$ is H, an unsubstituted $C_6$-$C_{18}$aryl group; a $C_6$-$C_{18}$aryl group, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—;

$R^{68}$ is H; an unsubstituted $C_6$-$C_{18}$aryl group; a $C_6$-$C_{18}$aryl group, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—;

$R^{69}$ is H, an unsubstituted $C_6$-$C_{18}$aryl; a $C_6$-$C_{18}$aryl, which is substituted by $C_1$-$C_{18}$alkyl, or $C_1$-$C_{18}$alkoxy; an unsubstituted $C_1$-$C_{18}$alkyl group; or a $C_1$-$C_{18}$alkyl group, which is interrupted by —O—;

$R^{70}$ and $R^{71}$ are independently of each other an unsubstituted $C_1$-$C_{18}$alkyl group; an unsubstituted $C_6$-$C_{18}$aryl group; or a $C_6$-$C_{18}$aryl group, which is substituted by $C_1$-$C_{18}$alkyl;

$R^{72}$ is an unsubstituted $C_1$-$C_{18}$alkyl group; an unsubstituted $C_6$-$C_{18}$aryl group, or a $C_6$-$C_{18}$aryl group, which is substituted by $C_1$-$C_{18}$alkyl;

$R^{73}$ and $R^{74}$ are independently of each other H; unsubstituted $C_6$-$C_{18}$aryl; $C_6$-$C_{18}$aryl which is substituted by $C_1$-$C_{18}$alkyl, or $C_1$-$C_{18}$alkoxy; unsubstituted $C_1$-$C_{18}$alkyl; or $C_1$-$C_{18}$alkyl which is interrupted by —O—;

$R^{75}$ is a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{80}$, $R^{81}$ and $R^{82}$ are independently of each other a $C_1$-$C_{25}$alkyl group, which can optionally be interrupted by O; a $C_6$-$C_{14}$aryl group, which can optionally be substituted by $C_1$-$C_{18}$alkyl; or a heteroaryl group comprising 5 to 11 ring atoms, which can optionally be substituted by $C_1$-$C_{18}$alkyl; and $X^-$ is halide, $BF_4^-$, $PF_6^-$, $SbF_6^-$, $ClO_4^-$, with a Pt salt or a Pd salt, and mixtures thereof, in the presence of a Ag or Cu(I) salt;

(ii) contacting the product obtained in step (i) with a compound of formula (VII)

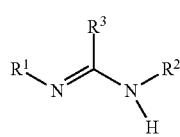

(VII)

wherein $R^1$ and $R^2$ are independently of each other a $C_1$-$C_{18}$alkyl group, which can optionally be substituted by at least one substituent E; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a $C_1$-$C_{18}$haloalkyl group; or CN;

$R^3$ is hydrogen; a $C_1$-$C_{18}$alkyl group, which can optionally be substituted by at least one substituent E and/or interrupted by D; a $C_3$-$C_{12}$cycloalkyl group, which can optionally be substituted by at least one substituent E; a heterocycloalkyl group comprising 3 to 6 ring atoms, interrupted by at least one of O, S and $NR^{65}$ and/or substituted by at least one substituent E; a $C_6$-$C_{14}$aryl group, which can optionally be substituted by at least one substituent G; a —O—$C_6$-$C_{14}$aryl group, which can optionally be substituted by at least one substituent G; a heteroaryl group comprising 5 to 11 ring atoms, which can optionally be substituted by at least one substituent G, interrupted by at least one of O, S, N and $NR^{65}$; a halogen atom; a $C_1$-$C_{18}$haloalkyl group; or CN;

or $R^1$ and $R^3$ or $R^2$ and $R^3$ together form a group of formula

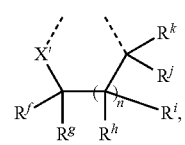

(III)

wherein X' is present in the position of $R^3$ and is selected from O, S, $NR^{75}$ and $CR^{73}R^{74}$;

$R^f$, $R^g$, $R^h$, $R^i$, $R^j$ and $R^k$ are independently of each other H, a $C_1$-$C_5$alkyl group, a fluoro$C_1$-$C_4$alkyl group, or a $C_3$-$C_6$cycloalkyl group;

n is 0 or 1;

wherein the group of formula (III) comprises 0, 1 or 2 double bonds;

in the case that 1 or 2 double bonds are present in the group of formula (III), the carbon atoms connected with the double bonds are each substituted by only one residue $R^f$, $R^j$ and/or—in the case that n is 1—$R^h$;

in the presence of a base.

11. An organic light emitting diode comprising a complex of formula (I) or (II) according to claim 1.

12. A light-emitting layer comprising a complex of formula (I) or (II) according to claim 1.

13. A light emitting layer according to claim 12 comprising the complex of formula (I) or (II) as emitter material together with at least one host material.

14. An organic light emitting diode comprising a light emitting layer according to claim 12.

15. A device selected from the group consisting of stationary visual display units such as visual display units of computers, televisions, visual display units in printers, kitchen appliances, advertising panels, illuminations, information panels; mobile visual display units such as visual display units in smartphones, tablet computers, cellphones, laptops, digital cameras, MP3 players, vehicles and destination displays on and in buses and trains: illumination units; keyboards; items of clothing; furniture; and wallpaper, comprising the organic light emitting device according to claim 11.

16. An emitter material comprising the complex of formula (I) or (II) according to claim 1.

\* \* \* \* \*